United States Patent [19]

König et al.

[11] 4,016,282

[45] Apr. 5, 1977

[54] UREIDOACETAMIDO-PENICILLINS

[75] Inventors: Hans-Bodo König; Wilfried Schröck, both of Wuppertal-Elberfeld; Hans Disselnkötter, Cologne; Karl Georg Metzer, Wuppertal-Elberfeld, all of Germany

[73] Assignee: Bayer Aktiengesellschaft, Germany

[22] Filed: Apr. 16, 1975

[21] Appl. No.: 568,384

Related U.S. Application Data

[62] Division of Ser. No. 425,966, Dec. 19, 1973, Pat. No. 3,959,258, which is a division of Ser. Nos. 145,809, May 21, 1971, abandoned, and Ser. No. 145,877, May 21, 1971, abandoned.

[30] Foreign Application Priority Data

May 25, 1970 Germany .......................... 2025414
May 25, 1970 Germany .......................... 2025415

[52] U.S. Cl. .............................................. 424/271
[51] Int. Cl.² ........................................ A61K 31/43

[58] Field of Search ..................................... 424/271

[56] References Cited

UNITED STATES PATENTS

| 3,479,339 | 11/1969 | Holdrege ........................ 260/239.1 |
| 3,483,188 | 12/1969 | McGregor ........................ 424/271 |

FOREIGN PATENTS OR APPLICATIONS 734,455   1969   Belgium ............................ 260/239.1

*Primary Examiner*—Norman A. Drezin

[57] ABSTRACT

6-(α-3-Acyl-ureidoacetamido)-penicillanic acids and pharmaceutically acceptable non-toxic salts thereof in which the hydrogen atom of the nitrogen atom present in the 3-position is substituted, are effective against Gram-positive and Gram-negative infections, particularly *Klebsiella aerobacter* infections.

31 Claims, No Drawings

UREIDOACETAMIDO-PENICILLINS

CROSS-REFERENCE

This is a divisional of our copending application Ser. No. 425,966 filed Dec. 19, 1973, now U.S. Pat. No. 3,959,258 issued May 25, 1976, which in turn is a division of applications Ser. Nos. 145,809 and 145,877 filed May 21, 1971, now abandoned.

The present invention relates to new penicillins which are useful as anti-bacterial agents for humans, poultry and animals, and foodstuff additives in animal fodder. They are particularly useful in the treatment of illnesses due to infection by Gram-positive and Gram-negative bacteria, and especially by Klebsiella bacteria such as *Klebsiella aerobacter*.

Anti-bacterial agents, such as ampicillin (U.S. Pat. No. 2,985,648) have proved very effective in the therapy of infections by Gram-positive and Gram-negative bacteria. However, they are not capable of effectively combating Klebsiella infections. Carbenicillin (U.S. Pat. Nos. 3,142,673 and 3,282,926) is only effective in man in the case of infections by *Klebsiella* bacteria if it is administered in continuing high doses, such as are only achieved by infusion.

6-($\alpha$-3-Acylureidoacetamido)-penicillanic acids are described in Netherlands Patents Nos. 69,01646 and 69,08909 and in U.S. Pat. Nos. 3,479,339, 3,483,188 and 3,481,922 and German Offenlegungsschrift 1,959,920 but all 3-acylureido acetamidopenicillanic acids described and claimed in these Patents possess, in contrast to those of the present invention, a hydrogen atom on the nitrogen atom present in the 3-position in the acylureido group. The presence of this hydrogen atom and the absence of another substituent at this position of the acylureido group in part necessarily results from the different way of synthesising these penicillins.

More particularly, the present invention is concerned with penicillins of the formula:

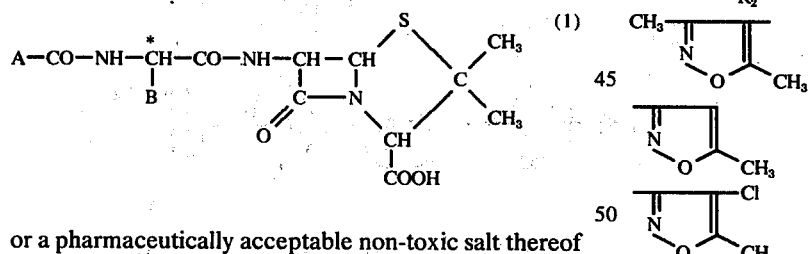

or a pharmaceutically acceptable non-toxic salt thereof wherein

A is a group of the formula:

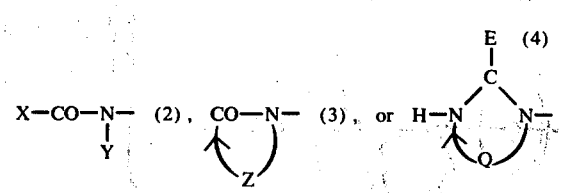

wherein

X is hydrogen, alkyl, preferably lower alkyl, alkenyl, preferably lower alkenyl, cycloalkyl or cycloalkenyl with up to 10 carbon atoms, arylvinyl, especially phenylvinyl, mono-, di-, or tri-halo(lower alkyl), (lower alkyl)amino, di(loweralkyl)amino, monoarylamino, aryl especially phenyl (lower alkyl)amino, aryloxy especially phenoxy, alkoxy or aralkoxy with up to 8 carbon atoms, cycloalkoxy with up to 7 carbon atoms, or a group of the formula:

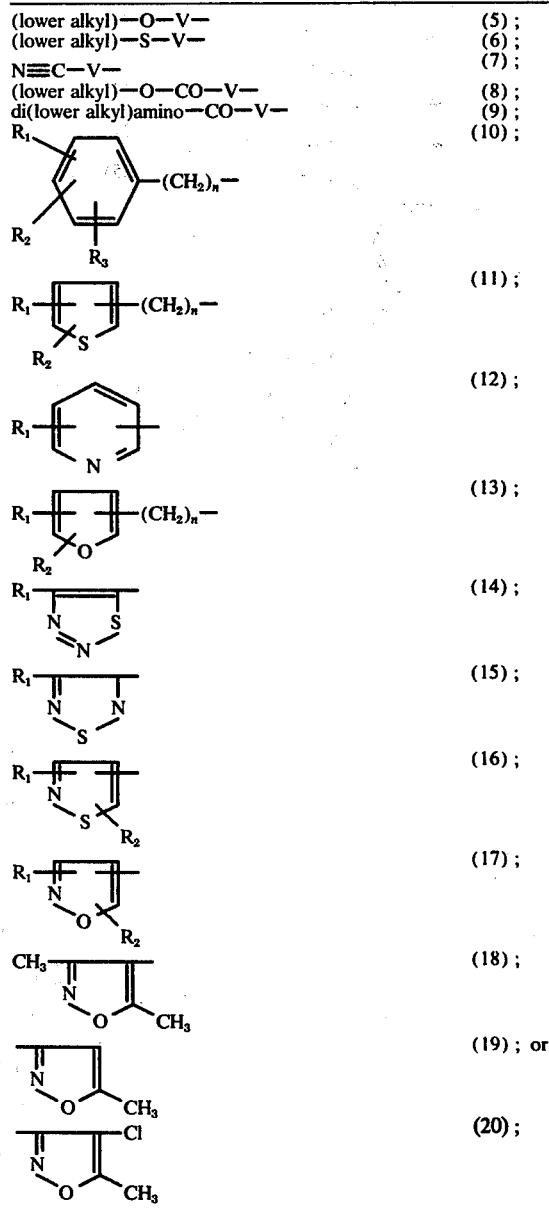

wherein

V is a bivalent organic radical with 1 to 3 carbon atoms;

$n$ is 0, 1 or 2;

$R_1$, $R_2$ and $R_3$ are the same or different and are each hydrogen, chlorine, bromine, iodine, fluorine, nitro, cyano, di(lower alkyl)amino, di(lower alkyl)aminocarbonyl, lower alkanoylamino, lower alkoxycarbonyl, lower alkanoyloxy, lower alkyl, lower alkoxy, sulphamyl or trifluoromethyl;

Y is alkyl, especially lower alkyl, alkenyl, especially lower alkenyl such as vinyl and propenyl, cycloalkyl or cycloalkenyl with up to 10 carbon atoms, mono-, di-, or tri-halo(lower alkyl), aryl especially phenyl, a heterocyclic group, or aralkyl with up to 8 carbon atoms;

—Z— is a divalent group of the formula:—

 (21);

 (22);

 (23);

 (24);

(25);

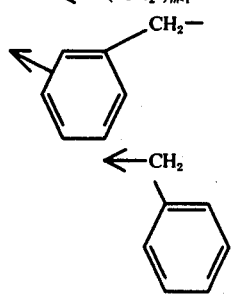 (26); or

 (27);

wherein
m is 3, 4 or 5 and the arrow ←— means that the two free valencies of the group Z are not arbitrarily joined to the N and C atoms of the group

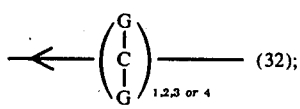 (3)

but are oriented as indicated by the arrow;
Q is a divalent group, and in particular a group of the formula:

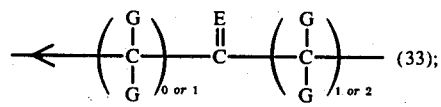 (32);

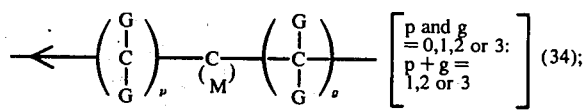 (33);

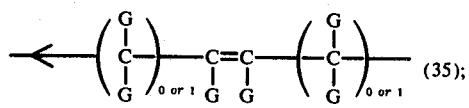 $\begin{bmatrix} p \text{ and } g \\ = 0,1,2 \text{ or } 3: \\ p+g = \\ 1,2 \text{ or } 3 \end{bmatrix}$ (34);

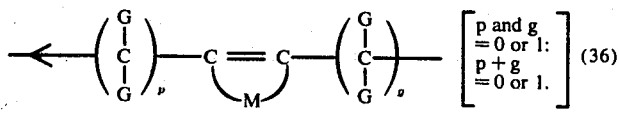 (35);

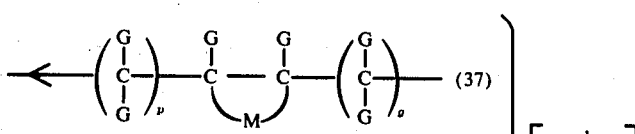 $\begin{bmatrix} p \text{ and } g \\ = 0 \text{ or } 1: \\ p+g \\ = 0 \text{ or } 1. \end{bmatrix}$ (36)

(37)

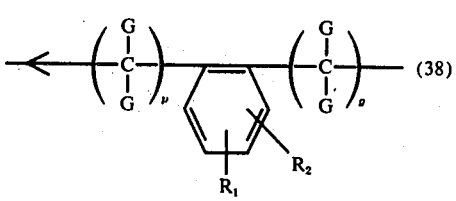 (38)

$\begin{bmatrix} p \text{ and } g \\ = 0 \text{ or } 1: \\ p+g \\ = 0 \text{ or } 1 \end{bmatrix}$

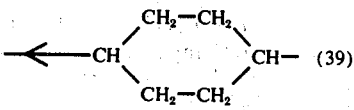 (39)

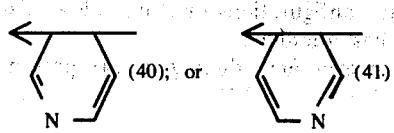

E is oxygen or sulphur;
G is hydrogen or lower alkyl;
$R_1$ and $R_2$ are as above defined;
the arrow in the divalent group ←Q— means that the two free valencies of the group Q are not arbitrarily joined to the two nitrogen atoms of the group

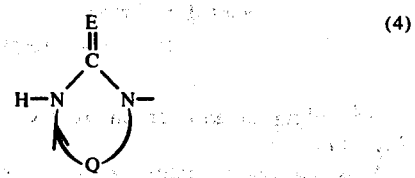

but are oriented as indicated by the arrow:
M is a group of the formula:

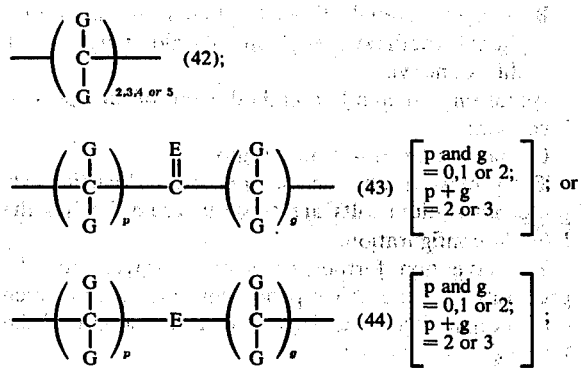

wherein
E and G are as above defined;
B is a group of the formula:

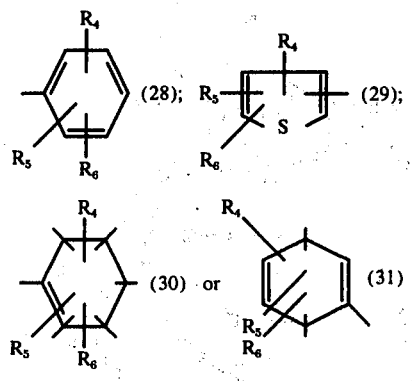

wherein
$R_4$, $R_5$ and $R_6$ are the same or different, and are each hydrogen, halogen, lower alkyl, lower alkoxy, lower alkylthio, lower alkylthionyl, lower alkylsulphonyl, nitro, di(lower alkyl)amino, lower alkanoylamino, hydroxy, or lower alkanoyloxy and which, as regards the chirality center C*, can have either of the two possible R- and S- stereomeric configurations.

The invention covers not only pure R- and S-stereoisomers, but also mixtures of these isomers in any proportions.

The salts to which the invention more particularly relates are the non-toxic pharmaceutically tolerated salts, which include salts of the acid carboxyl group.

The above mentioned pharmaceutically acceptable non-toxic tolerated salts include salts of the acid carboxyl group, such as sodium, potassium, magnesium, calcium, aluminium and ammonium salts, and non-toxic substituted ammonium salts with amines such as di- and tri-lower alkylamines, procaine, dibenzylamine, N,N'-dibenzylethylenediamine, H-benzyl-β-phenylethylamine, N-methylmorpholine and N-ethylmorpholine, 1-ephenamine, dehydroabietylamine, N,N'-bis-dehydroabietylethylenediamine, N-lower alkylpiperidine and other amines which have been used for forming salts of penicillins.

The term "lower alkyl" is to be understood, in the present invention, as meaning both a straight-chain and a branched alkyl group with up to 6 carbon atoms. In conjunction with other groups, such as in "di-lower alkylamino," the term "-lower alkyl-" only relates to the alkyl part of the particular group.

The phrase "the compound of the present invention" includes the pharmaceutically acceptable non-toxic salts of the penicillins of the present invention.

According to one embodiment of the present invention A is:

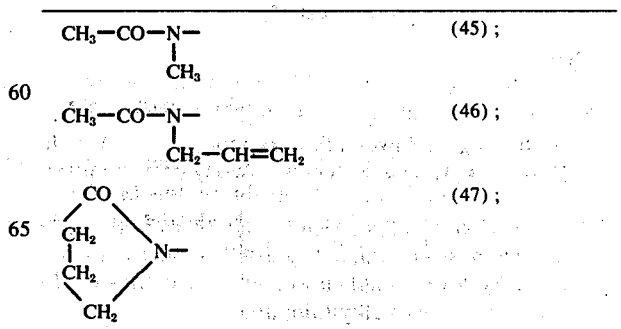

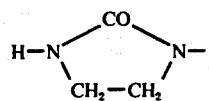 (48);

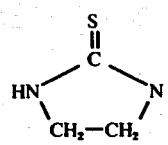 (49);

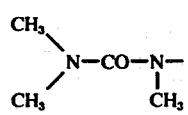 (50);

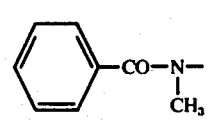 (51);

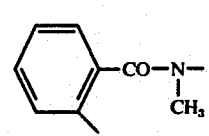 (52);

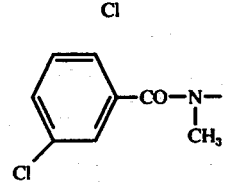 (53);

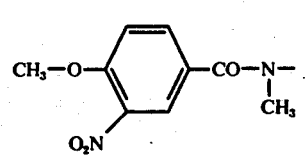 (54); or

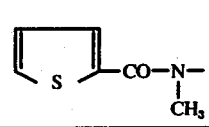 (55); and

B is phenyl.

These stereoisomers in which the chirality center C* is in the R-configuration, i.e. (D—)—, are preferred.

According to another embodiment of the present invention:
B is p-methylthiophenyl, p-methylphenyl, p-methoxyphenyl, p-chlorophenyl or thienyl-(2).

According to another embodiment of the present invention:

$$A \text{ is } X-CO-N(-Y)-$$

wherein
X is hydrogen, lower alkyl, mono-, di- or tri-halo (lower alkyl), lower alkoxy, allyloxy or cyclohexyloxy;
Y is lower alkyl, allyl or mono-halo(lower alkyl);
B is cyclohexenyl, thienyl, phenyl or phenyl substituted by lower alkyl, lower alkoxy, mono- or di-halogen or lower alkylthio; and
C* can have either of the two possible R- and S-stereoisomeric configurations or it can be a mixture of such diastereomers.

According to another embodiment of the present invention:

$$A \text{ is } CH_3-C(=N-)-N(-CH_3)$$

According to another embodiment of the present invention:

$$A \text{ is } CH_3-CO-N(-C_2-CH=CH_2)-$$

According to another embodiment of the present invention:
X is hydrogen, methyl, ethyl, propyl, chloroethyl, chloropropyl, trichloropropyl, tri-fluoropropyl, methoxy, ethoxy, propoxy, hetoxy, allyloxy or cyclohexyloxy;
Y is methyl, ethyl, propyl, chloroethyl or allyl; and
B is cyclohexenyl, thienyl, phenyl, tolyl, chlorophenyl, methoxyphenyl, methylthiophenyl, or dichlorophenyl.

According to another embodiment of the present invention:
C* has the D(—)— configuration.

The preferred salt is the sodium salt and particularly preferred sodium salts are those wherein C* has the D(—)— configuration.

The invention further provides a process for the preparation of the above penicillins and salts in which 6-aminopenicillanic acid (52) or a compound of the formula (53) or (54):

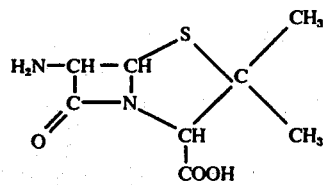 (52)

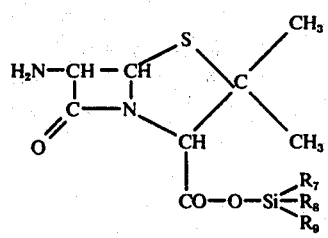 (53) or

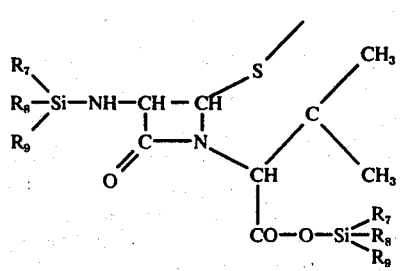 (54)

in which $R_7$, $R_8$ and $R_9$ are the same or different alkyl having up to 6 carbon atoms; is reacted at a temperature of $-30°$ to $+50°$ C with a carboxylic acid of the formula:

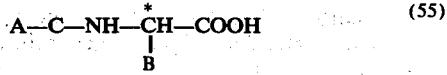 (55)

modified at the carboxyl group, wherein

A, B and C* are as above defined.

This reaction is, when 6-aminopenicillanic acid is used, carried out in an anhydrous or aqueous solvent, in the presence of a base. If a compound of the formula (53) or (54) is used, the reaction is carried out in an anhydrous solvent, free of hydroxyl groups, with or without the addition of a base.

The carboxyl group of the carboxylic acids of the formula (55) may be modified by either i. reacting such a carboxylic acid with about one molar equivalent of a compound of the formula (56), (50), (51), or (52):

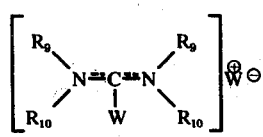 (57)

 (58)

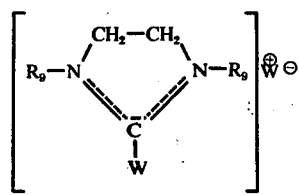 (59)

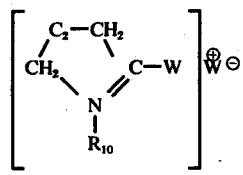 (60)

wherein $R_9$ is as above defined;

$R_{10}$ is the same as $R_9$ and in addition may be phenyl;

$R_{11}$ is a divalent organic radical $-(CH_2)_4-$, $-(CH_2)_5-$ or $-(CH_2)_2O-(CH_2)_2-$; and W is halogen;

in an anhydrous, inert organic solvent in the presence of about one molar equivalent of a base at a temperature of about $-60°$ C to $+30°$ C; or ii. by converting a carboxylic acid of the formula (55) into the corresponding carboxylic acid derivative of the formula (60):

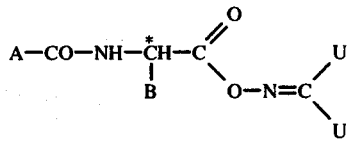 (60)

wherein

A, B and C* are as above defined and each U is —CN or —COO-lower alkyl.

The carboxylic acid derivatives of the formula (60) may be prepared by reacting a compound of the formula (61):

 (61)

wherein

U is as above defined, in an anhydrous, inert organic solvent, in the presence of at least one molar equivalent of a tertiary organic base, at a temperature of from $-25°$ C to $+25°$ C, with one molar equivalent of thionyl chloride, to obtain an intermediate product, with one molar equivalent of base hydrochloride being formed. The intermediate product is then reacted, without isolation and in the presence of a further molar equivalent of a base, with a molar equivalent of the carboxylic acid of the formula (55) at a temperature of about $-25°$ C to $+25°$ C, to give the modified carboxylic acid of the formula (60).

In carrying out the process of the invention using 6-amino-penicillanic acid, the modified carboxylic acid of formula (55) preferably in the form of a solution in an anhydrous, inert organic solvent, is brought together with a solution of 6-aminopenicillanic acid in water or in an aqueous or anhydrous organic solvent, in the presence of a base. Suitable solvents for the carboxylic acids modified at the carboxyl group are, for example, acetone, tetrahydrofurane, dioxane, dimethylformamide, dimethylsulphoxide and hexamethylphosphoric acid triamide for an aqeuous reaction medium, and preferably methylene chloride and chloroform for an anhydrous reaction medium.

The 6-aminopenicillanic acid is preferably employed in the reaction according to the invention as a solution of its salt with a base, in water or in a mixture of water and a water-miscible solvent, or in an anhydrous organic solvent. Suitable solvents for the 6-aminopenicillanic acid or its salt, apart from water, are preferably acetone, tetrahydrofurane, dioxane, acetonitrile, dimethylformamide, dimethylsulphoxide, hexamethylphosphoric acid triamide and isopropanol for an aqueous reaction medium and, in addition to the solvents mentioned, preferably methylene chloride and chloroform for an anhydrous reaction medium. In order to convert the 6-aminopenicillanic acid into the salt of a base, the salt being dissolved in a solvent, inorganic bases such as sodium carbonate, sodium hydroxide, sodium bicarbonate, the corresponding potassium and calcium compounds, magnesium oxide or magnesium carbonate or buffer mixtures can for example be used as bases suitable for the purpose in the case of an aqueous or water-containing reaction mixture, whilst triethylamine, pyridine, diethylamine, N-ethylpiperidine or N-ethylmorpholine can preferably be used in the case of an anhydrous reaction medium.

The reaction, according to the invention, of the carboxylic acids of the formula (55), modified at the carboxyl group, with the silylated 6-aminopenicillanic acids of the formulae (53) and (54) is carried out in inert organic solvents which are free of hydroxyl groups, for example in carbon tetrachloride, methylene chloride, chloroform, tetrahydrofurane, benzene, diethyl ether and toluene.

The reaction, according to the invention, of the carboxylic acids of the formula (55), in the form which is modified at the carboxyl group, with the 6-aminopenicillanic acid, in an aqueous or water-containing medium, can be carried out at a pH of, preferably, 6.5 to 8.0, or also at a pH of about 3.

As in the case of most chemical reactions, higher or lower temperatures than those indicated in the Examples can be used. However, if the values indicated in the Examples are substantially exceeded, side-reactions will occur to an increasing extent, and these reduce the yield or disadvantageously affect the purity of the products. On the other hand, excessively lowered reaction temperatures reduce the speed of reaction so much that reductions in yield can occur. Reaction temperatures of −20° C to +30° C are therefore preferred in the reaction according to the invention, of the carboxylic acids of the formula (55), modified at the carboxyl group, with the 6-aminopenicillanic acid or the silylated 6-aminopenicillanic acids of the formulae (53) and (54). Only in cases where the carboxylic acids modified at the carboxyl group are insufficiently stable, or there is the danger that racemisation may occur at an optically active centre located near the carboxyl group, can it be advisable preferably to carry out the process at reaction temperatures below −20°. In the reaction, according to the invention, of the carboxylic acids of the formula (55), modified at the carboxyl group, with the 6-aminopenicillanic acid or the compounds of the formulae (53) and (54), the reactants can be reacted in equimolar amounts. It may however be advisable to use one of the two reactants in excess in order to facilitate the purification of the desired penicillin, or its preparation in a pure form, and to increase the yield. Thus it is, for example, possible to employ the 6-aminopenicillanic acid or the compounds of the formulae (53) and (54) in an excess of 0.1 to about 0.4 mol equivalent and thereby to achieve better utilisation of the carboxylic acids of the general formula (55). When working up the reaction mixture and isolating the penicillin, 6-aminopenicillanic acid which may be present can be easily removed because of its good solubility in aqueous mineral acids. Any carboxylic acid [see formula (55)] which may be present can, on the other hand, only be separated with much greater difficulty from the penicillin formed.

The amount of bases added in the reaction, according to the invention, of the carboxylic acids of the formula (55), modified at the carboxyl group, with 6-aminopenicillanic acid or the compounds of the formulae (53) and (54) is for example determined by the desired maintenance of a particular pH. Where a pH measurement and adjustment is not carried out, or is not possible or sensible because of the absence of sufficient water in the diluent, about 0.5 to 2.0 mol equivalents of base are added in the case where the compounds of the formula (53) or (54) are used, and about 1.5 to 2.5 mol equivalents of base are added in the case where 6-aminopenicillanic acid and an anhydrous reaction medium are used.

The working up of the reaction batches for the manufacture of the penicillins according to the invention, and of their salts, in all cases takes place in the manner generally known for penicillins.

The carboxylic acids of the formula (55) can be modified at the carboxyl group, according to the invention, by reacting them with about one molar equivalent of a compound of one of the formulae (56), (57) (58) or (59) in an anhydrous, inert organic solvent in the presence of about one molar equivalent of a base, preferably a tertiary organic base, at a temperature of about −60° C to +30° C, preferably −30° C to +5° C, most preferably −20° C to +5° C. The forms of the carboxylic acids, modified at the carboxylic group, which are thereby produced are preferably not isolated, but used, together with the solvent in which they are present, for the reaction with the 6-aminopenicillanic acid or the compounds of the formulae (53) or (54). If the reaction mixture for the reaction with the aminopenicillanic acid contains water, organic solvents which are miscible with water, for example acetone, tetrahydrofurane, dioxane, dimethylformamide, dimethylsulphoxide or hexamethylphosphoric acid triamide, are preferentially used as solvents for the reaction of the carboxylic acids (55) with the compounds (56), (57), (58) or (59). If the reaction mixture for the reaction with 6-aminopenicillanic acid does not contain any water, or if the reaction mixture for the reaction with compounds of the formulae (53) or (54) is concerned, solvents such as, preferably, methylene chloride or chloroform are also used, in addition to the solvents mentioned.

According to the invention it is also possible to modify the carboxylic acids of formula (55) at the carboxyl group by conversion into the derivatives of the formula:

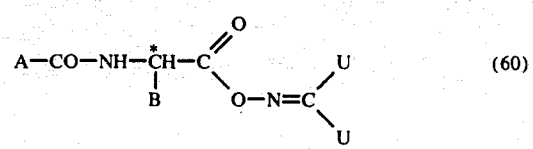

wherein

A, B, C* and U are as above defined.

This is expediently done by first converting a compound of the formula (61):

wherein

U is as above defined, in an anhydrous, inert organic solvent, for example acetone, tetrahydrofurane, methylene chloride, dioxane, chloroform or dimethylformamide, in the presence of at least, and preferably, one mole equivalent of a tertiary base, preferably triethylamine, at temperatures of about −25° C to +25° C, preferably −10° C, into an intermediate product by means of one mol equivalent of thionyl chloride, with one mol equivalent of base hydrochloride being formed. This intermediate product, the constitution of which is unknown, is not isolated, but is reacted in the presence of a further molar equivalent of an organic base, also preferably triethylamine, with one molar equivalent of the carboxylic acid of formula (55) at a temperature of about −25° C to +25° C, preferably −10° C to +10° C. After the base hydrochloride has been removed by filtration, the appropriate compound of the formula (60) can be isolated by evaporating off the solvent and can optionally be purified by recrystallisation from inert solvents or, if the substance is not crystalline, by brief washing of a solution, for example in ether or benzene, with an aqueous bicarbonate solution at as low a temperature as possible.

The 6-aminopenicillanic acid used as starting material in the process of the invention can be obtained by known methods, for instance by fission of penicillin-G, either by microbiological or by chemical means (compare Netherlands Patent No. 67/13809).

The carboxylic acids of formula (55) can be obtained from the amino-acids of the formula:

wherein
B is as above defined, by reaction with a compound of the formula:

wherein
A and W are as above defined.

The compounds of the formula (63) in which W is halogen, can be obtained by processes described in German Pat. No. 1,256,747, in German Pat. No. 1,259,871, in U.S. Pat. Nos. 3,275,618 and 3,337,621, and in Japanese Pat. No. 434,247.

Furthermore, some of the compounds of formula (63) in which W is halogen can be obtained from the corresponding amide by metallization at the amide nitrogen atom with methyl, lithium, followed by reaction with phosgene.

The compounds of formula (63) in which W is halogen and A is

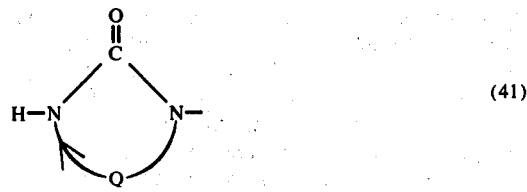

can be obtained from the cyclic ureas of formula:

wherein
Q is as above defined, and phosgene.
The reaction is illustrated in the examples.

The production of the reagents of the formulae (56), (57) and (59) is described in the literature [see J. Med. Chem. 9, (1966), p980; Ber. 96, (1963) p2681; Tetrahedron 17, (1962), p114]. The reagent of formula (58) can be obtained from N,N'dimethylethylene diamine after converting it into the N,N'-bis-trimethylsilyl compound, reacting this with phosgene to give the corresponding cyclic urea, and reacting the latter with phosgene.

The penicillins according to the invention can also be obtained from the carboxylic acids of the formula (55) and 6-aminopenicillanic acid, or the silylated 6-aminopenicillanic acids [see formulae (53) and (54)] by the known methods of peptide chemistry (see E. Schroder and K. Lubke, "The Peptides", Methods of Peptide Synthesis, Vol. I, pages 76–128). This method of production is however inferior to that of the present invention.

On attempting to obtain some of the penicillins according to the invention via the acid chlorides, prepared in the usual manner from the acids (formula (55)) and thionyl chloride, and 6-aminopenicillanic acid, we obtained a mixture of several penicillin, amongst which the desired penicillin, [identified by a preparation via a different, unambiguous route (from ampicillin and the corresponding acid chloride A—CO—Cl; compare formula (55) was either not present at all or only present in very small amounts. This was deduced from a comparision of the "in vitro" bacterial spectra and of the thin layer chromatogram. In an experiment to obtain the penicillins according to the invention via the mixed anhydrides, prepared in the usual manner from the acids by means of chloroformic acid ethyl ester, and aminopenicillanic acid, it was only possible to isolate ethoxycarbonylpenicillin in a yield of 20%.

The penicillins of the present invention can also be produced by reacting a compound of the formula:

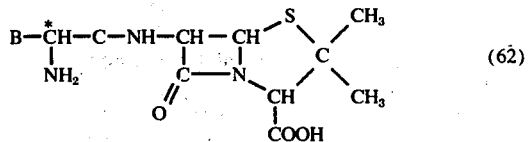

wherein
B and C* are as above defined,
or a condensation product of such a compound with a carbonyl compound, preferably acetone [U.S. Pat. No. 3,198,804], the said condensation product being of the formula:

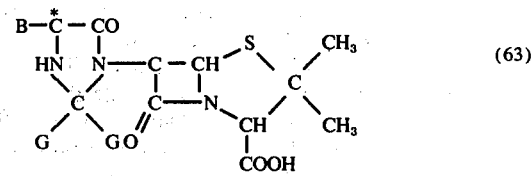

wherein
B and C* are as above defined, (in the preferred case when the carbonyl compound is acetone, G is methyl),
or a compound of the formula:

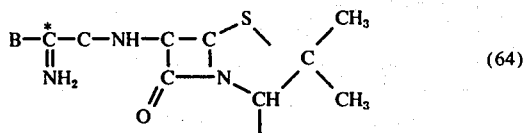

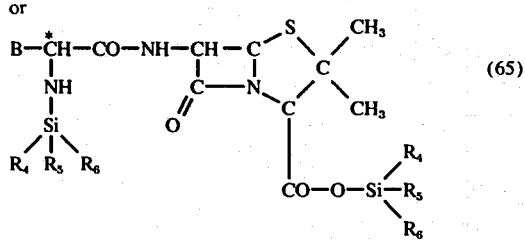

wherein
B is as above defined; and
$R_4$, $R_5$ and $R_6$ are alkyl with up to 6 carbon atoms, at a temperature of −20° C to +50° C with a compound of the formula:

or

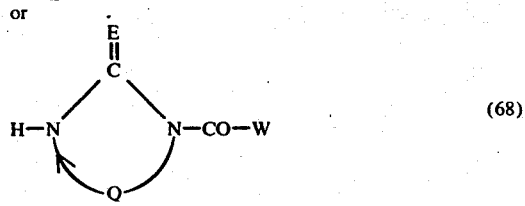

wherein
X, Y, Z, E and Q are as above defined; and
W is halogen or an azide group;
in a solvent and in the presence of a base when a compound of formula (62) or (63) is used, and in an anhydrous solvent free of hydroxyl groups with or without the presence of a base when a compound of formula (64) or (65) is used.

If a compound of the formulae (62) or (63) is used as the starting material for the synthesis of a penicillin according to the invention, and is reacted with a compound of the formulae (66), (67) or (68), the reactions can for example be carried out in a mixture of water and one or more organic solvents miscible with water, such as acetone, tetrahydrofurane, dioxane, acetonitrile, dimethylformamide, dimethylsulphoxide or isopropanol. At the same time, the pH of the reaction mixture is for example kept between 6.5 and 8.0 by adding a base or by the use of a buffer solution. The reaction according to the invention can however also be carried out in a different pH range, for example between 4.5 and 9.0 or at pH 2.0–3.0. It is furthermore possible to carry out the reaction in a solvent immiscible with water, for example chloroform or methylene chloride, with the addition of, preferably, triethylamine, diethylamine or Nethylpiperidine. Furthermore, the reaction can be carried out in a mixture of water and a solvent which is immiscible with water such as, for example, ether, chloroform, methylene chloride, carbon disulphide, isobutyl methyl ketone, acetic acid ethyl ester or benzene, in which case it is desirable to stir the mixture vigorously and to maintain the pH value between 4.5 and 9.0 or, for example, 2.0 and 3.0, by adding bases or by the use of a buffer solution.

If a compound of the formula (64) or (65) is used as the starting material for the synthesis, and this substance is reacted with a compound of the formula (66), (67) or (68), the process must be carried out in a solvent which is anhydrous and free of hydroxyl groups. Such solvents are for example methylene chloride, chloroform, benzene, tetrahydrofurane, acetone and dimethylformamide. In this case, the addition of a base is not necessary, but in individual cases the yield and purity of the products can be improved thereby. Admittedly, the converse effect is also possible. The base which is optionally added must either be a tertiary amine, such as pyridine or triethylamine, or a secondary amine which is difficult to acylate as a result of steric hindrance, such as dicyclohexylamine. The number of usable bases is hence almost unlimited.

As in most chemical reactions, higher or lower temperatures than those indicated in the Examples can be used. If, however, the values given in the Examples are significantly exceeded, side-reactions, which reduce the yield or unfavourably influence the purity of the products, will increasingly occur. On the other hand, excessively lowered reaction temperatures so greatly reduce the reaction speed that reductions in yield can occur. Reaction temperatures in the range of −20° C to +50° C are therefore preferred, and a temperature of about 0° C to +20° C is particularly preferred.

The reactants can be reacted with one another in equimolar amounts. It can however be desirable to use one of the two reactants in excess, in order to facilitate the purification, or preparation in a pure form, of the desired penicillin, and to increase the yield. For example, the compounds of the formulae (62) or (63) can be employed in an excess of 0.1 to 0.3 mol equivalents, and less decomposition of the reactants of the formulae (66), (67) or (68) in the aqueous solvent mixture can thereby be achieved. The excess of the reactants of the formulae (62) or (63) can be easily removed when working up the reaction mixture, because of their good solubility in aqueous mineral acid. On the other hand, however, the reactants of the formulae (66), (67) and (68) can also advantageously be employed in an excess of, for example, 0.1 to 1.0 mol equivalents. As a result of this, the reactants, for example of the formulae (62) or (63), are better utilized, and the decomposition of the reactants of the formulae (66), (67) or (68) which takes place as a side-reaction in aqueous solvents, is compensated. Since the compounds of the formulae (66), (67) or (68) which are added in excess rapidly change, in water, into neutral amides, ureas or thioureas which can easily be removed, the purity of the penicillins is thereby hardly impaired.

The amount of the base added is determined inter alia by the desired maintenance of a particular pH. Where a pH measurement and adjustment is not carried out, or is impossible or pointless because of the absence of sufficient amounts of water in the diluent, 2 mol equivalents of base are preferably added in the case where a compound of the formulae (62) or (63) is used, and either no base at all or, preferably 1 mol equivalent of base is added in the case where a compound of the formulae (64) or (65) is used.

The working up of the reaction batches for the manufacture of the penicillins according to the invention, and of their salts, can be throughout carried out in the manner generally known for penicillins.

The compounds of the formula (62) used as the starting material in the present invention can, as regards the configuration at the asymmetrical center in the side chain (: C*), be in the D(—)- = R-form or L(+)- = S-form. They are described in German Patent Specification No. 1,156,078, in United States Patent Nos. 3,342,677, 3,157,640, 2,985,648 and 3,140,282, in South African Patent No. 68/0290 and (an anhydrous form) in United States Patent No. 3,144,445. All crystal forms and configurations of the compounds of the formula (62) are suitable for use as the starting material for the reaction according to the invention. The compounds of the formulae (63), (64) or (65) used as the starting material in the present invention, can, as regards the configuration at the asymmetrical center in the side chain (: C*), also occur in the D(—)- = R-form or L(+)- = S-form. The configuration of the asymmetrical centers of the 6-aminopenicillanic acid nucleus in the compounds of the formulae (62), (63), (64) and (65) should be identical with the corresponding asymmetrical centers of the 6-aminopenicillanic acid, which has, for example, been obtained from penicillin-G by fermentative processes.

The production of the compounds of the formulae (64) and (65), used as the starting material, is described in Netherlands Patent No. 68/18057.

The compounds of the formulae (66) and (67) used as starting materials in the above process can be produced if W is halogen, according to processes which are described in German Pat. No. 1,250,747, in German Patent No. 1,259,871, in U.S. Nos. 3,275,618 and 3,337,621, and in Japanese Pat. No.

Furthermore compounds of the formulae (66) and (67) have been prepared, if W is halogen, from the corresponding amides after metallization with methyllithium and subsequent reaction with phosgene. Such preparations are described in more detail in the examples.

The production of the compounds of the formula (68), to be used as the starting material, — where W is halogen — is illustrated in Examples No. 144B and 147 B/C. It can also be carried out in the same manner as described in the examples.

The sales of the penicillines of the present invention can be obtained in a manner per se known, for example by reacting the free acid with a suitable base.

The chemotherapeutic activity of the new penicillins was tested in vivo and in vitro. The in vitro inhibition values (MIC = minimum inhibition concentration (see Tables 1 and 2) were determined in a liquid medium in the test tube series dilution test, with readings being taken after 24 hours' incubation at 37° C. The MIC is indicated by the non-turbid test tube in the dilution series. A complete medium of the following composition was used as the nutrient medium:

| Lab Lemco (OXOID) | 10 g |
| Peptone (DIFCO) | 10 g |
| NaCl | 3 g |
| D-(+)-Dextrose (MERCK) | 10 g |
| Buffer pH 7.4 | 1000 ml. |

The spectrum of action encompasses both Gram-negative and Gram-positive bacteria. The particular advantage of the penicillins according to the invention is that they are effective both in vitro (see Tables 1 and 2) and in animal experiments against ampicillin-resistant and carbenicillin-resistant *Klebsiella* bacteria and against ampicillin-resistant *Proteus* bacteria. Furthermore, ampicillin-resistant varieties of *Pseudomonas* are attacked in vitro and in vivo. The concentrations required for destruction of the bacteria are reached in the serum after parenteral administration.

The effect, which is generally excellent, is achieved both on a single administration and on repeated administration. The penicillins according to the invention are stable to acid. Some of the new penicillins are very well tolerated, which is made particularly clear through the extremely high dose which in these cases is tolerated, without complication, on intravenous administration into the vein of the tail.

Table 1

(MIC in units/ml) Bacterial strains

| Penicillin No.* | E. Coli T4 | A 261 | C 165 | Proteus vulg. 183/58 | 1017 | 3400 | Klebsiella K 10 | 63 | Psdm. aerug. Bonn | Walter | Staph. aureus 1777 E | 133 | Streptoc. faec. ATCC 9790 |
|---|---|---|---|---|---|---|---|---|---|---|---|---|---|
| 1 | 25 | >400 | 100 | 100 | 400 | 200 | 50 | 50 | 400 | 200 | | 1.6 | 200 |
| 2 | 3.1 | 400 | 12.5 | 12.5 | 100 | 25 | 50 | 50 | 100 | 100 | | ~0.8 | 200 |
| 4 | 0.8–4 | 100–500 | 4–20 | 4–20 | 4–20 | 4–20 | 20–100 | 20–100 | 20–100 | 20–100 | | >0.8 | 100–500 |
| 5 | | 100–500 | 4–20 | | | 20–100 | | 20–100 | | 20–100 | | >0.8 | 100–500 |
| 7 | 100–500 | >500 | 100–500 | 100–500 | ~500 | 100–500 | >500 | >500 | 100–100 | >500 | 100–500 | 0.8–4 | 100–500 |
| 8 | >500 | >500 | >500 | >500 | >500 | >500 | >500 | >500 | >500 | 100–500 | 4–20 | >500 | |
| 9 | 20–100 | >500 | 100–500 | 100–500 | >500 | >500 | >500 | >500 | >500 | >500 | | 0.8–4 | ~500 |
| 10 B | 12.5 | >400 | 50 | 50 | 200 | 200 | 50 | 50 | 200 | 200 | 400 | 1.6 | 100 |
| 11 C | 6.3 | >400 | 50 | 12.5 | 100 | 100 | 50 | 100 | 400 | 200 | 400 | 1.6 | 200 |
| 12 | 6.3 | >400 | 50 | 12.5 | 100 | 100 | 50 | 100 | 400 | 200 | 400 | 1.6 | 200 |
| 14 | 4–20 | >500 | 20–100 | 20–100 | 100–500 | ~100 | 20–100 | 20–100 | 100–500 | 100–500 | | 0.8–4 | 100–500 |
| 15 | 20–100 | >500 | 100–500 | 100–500 | >500 | >500 | >500 | >500 | >500 | >500 | | 0.8–4 | >500 |
| 17 | 4–20 | >500 | 20–500 | 20–100 | >500 | 100–500 | 20–100 | 20–100 | 100–500 | 100–500 | | >0.8 | 20–100 |
| 18 | 4–20 | >500 | 20–100 | 20–100 | 100–500 | 100–500 | 20–100 | 20–100 | 100–500 | 100–500 | | 0.8–4 | ~100 |
| 20 | | >500 | 20– | | | 100– | | 20–100 | | 100– | | >0.8 | 20–100 |

Table 1-continued (MIC in units/ml)
Bacterial strains

| Penicillin No.* | E. Coli 14 | A 261 | C 165 | 183/58 | Proteus vulg. 1017 | 3400 | Klebsiella K 10 | 63 | Psdm. aerug. Bonn | Walter | Staph. aureus 1777 E | 133 | Streptoc. faec. ATCC 9790 |
|---|---|---|---|---|---|---|---|---|---|---|---|---|---|
| 21 | | >500 | 100 20–100 | | | 500 20–100 | | 20–100 | | 500 100–500 | | >0.8 | 100–500 |
| 22 | | >500 | 4–20 | | | 4–20 | | 20–100 | | 20–100 | | <0.8 | ~20 |
| 23 | | >500 | 100–500 | | | >500 | | >500 | | >500 | | 0.8–4 | 100–500 |
| 24 | 6.3 | >400 | 25 | 25 | 100 | 50 | 50 | 100 | 100 | 100 | | ~1.6 | 200 |
| 27 | 100 | >400 | 200 | 200 | >400 | >400 | >400 | >400 | >400 | >400 | >400 | 6.3 | >400 |
| 28 | 100 | >400 | 200 | 400 | >400 | >400 | >400 | >400 | >400 | >400 | >400 | 12.5 | >400 |
| 29 | 3.1 | >400 | 6.3 | 3.1 | 12.5 | 12.5 | 200 | 100 | 25 | 50 | 200 | <0.8 | 100 |
| 30 | 4–20 | >500 | 20–100 | 20–100 | 100–500 | 100–500 | 100–500 | 100–500 | 100–500 | 100–500 | | 0.8–4 | 20–100 |
| 31 | 20–100 | >500 | 100–500 | 20–100 | 100–500 | 100–500 | 100– | 100–500 | approx.500 | 100–500 | | 0.8–4 | >500 |
| 32 | approx. 20 | >500 | 20–100 | 20–100 | approx.100 | 100–500 | 100–500 | approx.100 | 100–500 | 100–500 | | approx. 0.8 | 100–500 |
| 33 | | 100–500 | 4–20 | | 4–20 | | | 4–20 | | 4–20 | | <0.8 | 20–100 |
| 35 | approx. 4 | 100–500 | 20–100 | 4–20 | 20–100 | 20–100 | 20–100 | 20–100 | 4–20 | approx. 20 | | <0.8 | 20–100 |
| 36 | | >500 | 100–500 | | >500 | | | >500 | | >500 | | 4–20 | 100–500 |
| 37 | >0.8 | >500 | 0.8–4 | 0.8–4 | 4–20 | 4–20 | 20–100 | 4–20 | 4–20 | 4–20 | | <0.8 | 20–100 |
| 38 | 0.8–4 | >500 | 4–20 | 4–20 | 20–100 | 20–100 | 20–100 | 20–100 | 20–100 | 20–100 | | <0.8 | 100–500 |
| 44 | 6.25 | 400 | 25 | 25 | 50 | 25 | 50 | 50 | 50 | 50 | | 1.6 | 100 |
| 45 | 6,25 | >400 | 25 | 6,25 | 100 | 100 | 100 | 100 | 25 | 12,5 | 400 | <0,78 | 50 |
| 46 | 6,25 | >400 | 50 | 12,5 | 25 | 50 | 100 | 50 | 25 | 25 | 200 | 1,56 | 50 |
| 47 | 3,12 | >400 | 25 | 6,25 | 50 | 100 | 100 | 50 | 12,5 | 12,5 | 200 | <0,78 | 50 |
| 48 A | 3,12 | >400 | 12,5 | 6,25 | 25 | 50 | 100 | 50 | 25 | 12,5 | 200 | <0,78 | 25 |
| 51 | 3,12 | 400 | 12,5 | 12,5 | 25 | 25 | 100 | 50 | 12,5 | 12,5 | 400 | <0,78 | 25 |
| 52 | 3,12 | >400 | 12,5 | 6,25 | — | — | 100 | — | 12,5 | 12,5 | 200 | <0,78 | — |
| 53 | 3,12 | 400 | 6,25 | 12,5 | 6,25 | 12,5 | 50 | 25 | 6,25 | 12,5 | 200 | <0,78 | 12,5 |
| 54 | 6,25 | >400 | 25 | 6,25 | 200 | 100 | 100 | 100 | 12,5 | 25 | 200 | <0,78 | 50 |
| 55 | 6,25 | >400 | 25 | 12,5 | 100 | 100 | 100 | 100 | 12,5 | 25 | 200 | <0,78 | 50 |

*The numbers in this column are the numbers of the Examples in which the penicillin and its production are described.

Table 2

MIC in units/ml

Bacterial Strains

| Penicillin No: | E. coli 14 | A 261 | C 165 | 183/58 | Prot. vulg. 1017 | 3400 | Klebsiella K 10 | 63 | Pseudomonas aerug. Bonn | Walter | Staph. faec. aureus 1777E | 133 | Strep. ATCC 9790 |
|---|---|---|---|---|---|---|---|---|---|---|---|---|---|
| Amplicillin | ~0.8 | >400 | 6.25 | 200 | 400 | >400 | 100–200 | 100–200 | 200 | 200 | 200 | <1.0 | 12.5 |
| 59 | 1.56 | >400 | 6.25 | 3.12 | 6.25 | 12.5 | 25 | 50 | 12.5 | 25 | 100 | <0.78 | 100 |
| 60 | 6.25 | >400 | 25 | 12.5 | 25 | 50 | 100 | 50 | 25 | 50 | 50 | <0.78 | 100 |
| 61 | 3.12 | >400 | 6.25 | 6.25 | 25 | 25 | 100 | 50 | 12.5 | 25 | 200 | <0.78 | 50 |
| 62 | 1.56 | 400 | 6.25 | 3.12 | 6.25 | 6.25 | 100 | 100 | 12.5 | 25 | 400 | <0.78 | 100 |
| 63 | <0.78 | 400 | 1.56 | <0.78 | 1.56 | 3.12 | 50 | 50 | 6.25 | 12.5 | 200 | <0.78 | 50 |
| 64 | 3.12 | >400 | 25 | 25 | 25 | 100 | 100 | 100 | 25 | 50 | 50 | 1.56 | 100 |
| 65 | <0.78 | 400 | 3.12 | 1.56 | 3.12 | 6.25 | 12.5 | 12.5 | 12.5 | 12.5 | 50 | <0.78 | 50 |
| 66 | 3.12 | >400 | 12.5 | 50 | 50 | 100 | 50 | 50 | 6.25 | 12.5 | 50 | <0.78 | 25 |
| 67 | 1.56 | 400 | 6.25 | 1.56 | 6.25 | 6.25 | 100 | 100 | 25 | 50 | 400 | <0.78 | 100 |
| 68 | 3.12 | >400 | 12.5 | 6.25 | 12.5 | 25 | 50 | 25 | 12.5 | 12.5 | 50 | <0.78 | 50 |
| 69 | 1.56 | 400 | 6.25 | 3.12 | 12.5 | 25 | 50 | 25 | 12.5 | 100 | | <0.78 | 100 |
| 70 | 3.12 | 200 | 6.25 | 3.12 | 12.5 | 12.5 | 25 | 12.5 | 12.5 | 100 | | <0.78 | 100 |
| 71 | >400 | >400 | >400 | >400 | >400 | >400 | >400 | >400 | >400 | >400 | | 200 | >400 |
| 72 | 6.25 | 400 | 25 | 12.5 | 50 | 200 | 100 | 50 | 50 | 400 | | <0.78 | 100 |
| 73 | 3.12 | 200–400 | 6.25 | 1.56 | 6.25 | 12.5 | 25–50 | 12.5–25 | 12.5 | ~50 | | 0.78 | 50–100 |
| 74 | 100 | >400 | >400 | >400 | >400 | >400 | >400 | >400 | >400 | >400 | | 25 | >400 |
| 75 | <0.8 | 100<500 | 0.8<4 | 0.8<4 | 4<20 | 0.8<4 | 20<100 | 4<20 | 4<20 | 4<20 | | 0.8 | 20<100 |
| 76 | 0.8<4 | 100<500 | 4<20 | ~4 | 4<20 | 20<100 | 20<100 | 20<100 | 4<20 | 20<100 | | <0.8 | 20<100 |
| 83 | 3.12 | 400 | 6.25 | 6.25 | 25 | 6.25 | 25 | 50 | 50 | 100 | | <0.78 | 100 |
| 86 | 12.5 | >400 | 25 | 50 | 50 | 50 | 100 | 50 | 25 | 50 | <0.78 | 100 | |
| 87 | 4<20 | 100<500 | 20 | 20 | 20 | 20<100 | 20<100 | 20<100 | 4<20 | 20<100 | | <0.8 | 20<100 |
| 88 | 1.56 | 400 | 6.25 | 3.12 | 12.5 | 6.25 | 50 | 25 | 25 | 50 | | <0.78 | 50 |
| 89 | 1.56 | 400 | 6.25 | 1.56 | 3.12 | 12.5 | 25 | 12.5 | 25 | 50 | | <0.78 | 100 |
| 90 | 6.25 | 400 | 12.5 | 12.5 | 25 | 50 | 25 | 25 | 25 | 50 | 50 | <0.8 | 100 |
| 91 | | 100<500 | 0.8<4 | | 0.8<4 | | | 4<20 | | 4<20 | | <0.8 | 20<100 |
| 92 B | | >500 | 4<20 | | 20<100 | | | 20<100 | | 20<100 | | <0.8 | 20<100 |

Table 2-continued

MIC in units/ml

| Penicillin No: | E. coli 14 | A 261 | C 165 | 183/58 | Prot. vulg. 1017 | 3400 | Klebsiella K 10 63 | Pseudomonas aerug. Bonn | Walter | Staph. faec. aureus 1777E | 133 | Strep. ATCC 9790 |
|---|---|---|---|---|---|---|---|---|---|---|---|---|
| 93 B |  | >500 | 4<20 |  | 20 |  | 20 | 20 <100 |  | 20 <100 | <0.8 | 20 <100 |
| 94 | 12.5 | >400 | 50 | 100 | 100 | 50 | 200 | 200 | 100 | 100 |  | 3.12 | 200 |
| 96 | 6.25 | >400 | 12.5 | 25 | 50 | 50 | 200 | 200 | 25 | 25 | 400 | 1.56 | 25 |
| 97 | 6.25 | >400 | 25 | 6.25 | 25 | 25 | 400 | 50 | 25 | 50 |  |  |  |
| 98 | 3.12 | >400 | 6.25 | 6.25 | 12.5 | 25 | 400 | 400 | 12.5 | 25 | 200 | <0.78 | 100 |
| 99 B |  | >500 | 20–100 |  | approx. 500 |  |  | >500 |  | 100–500 |  | <0.8 | 100–500 |
| 101 B |  | >500 | 20–100 |  | 100–500 |  |  | 100–500 |  | 100–500 |  | <0.8 | approx. 20 |
| 102 |  | >500 | 4<20 |  | 4<20 |  |  | 20 <100 |  | 4<20 |  | <0.8 | 4<20 |
| 103 |  | >500 | 4–20 |  | 100–500 |  | 100–500 | 100–500 |  |  |  | <0.8 | 20–100 |
| 105 B |  | >500 | 4–20 |  | >500 |  |  | 100–500 |  | >500 |  | <0.8 | 20–100 |
| 107 | <0.8 | 20 <100 | <0.8 | <0.8 | 0.8–4 | 0.8–4 | ~4 | 4–20 | 0.8–4 | 0.8–4 | 20–100 | <0.8 | 4–20 |
| 108 |  | >500 | 4–20 |  | 20–100 |  |  | 100–500 | 0.8–4 | 20–100 |  | <0.8 | ~20 |
| 109 |  | >500 | 4–20 |  | 20–100 |  |  | 100–500 |  | 50–100 |  | 0.8 | 4–20 |
| 110 | 0.8–4 | 100–500 | 4–20 | 4–20 | 4–20 | 4–20 | 4–20 | 4–20 | 20–100 | 20–100 | 20–100 | 0.8 | 4–20 |
| 111 | <0.8 | 20–100 | 0.8–4 | <0.8 | 0.8–4 | 0.8–4 | 4–20 | 4–20 | 4–20 | 4–20 | 4–20 | 0.8 | 4–20 |
| 112 | <0.8 | 20–100 | 0.8–4 | <0.8 | 0.8–4 | 0.8–4 | 4–20 | 4–20 | 4–20 | 4–20 | 20–100 | 0.8 | 4–20 |
| 113 |  |  | 0.8–4 |  | 4–20 |  |  | 100–500 |  | 4–20 | 100–500 | 0.8 |  |
| 114 |  |  | 4–20 |  | 20–100 |  |  | 100–500 |  | 4–20 | 100–500 | 0.8 |  |
| 115 |  |  | 20–100 |  | 20–100 |  |  | 100–500 |  | 20–100 | 100–500 | 0.8 |  |
| 116 |  |  | 4–20 |  | 4–20 |  |  | 20–100 |  | approx. 20 | 100–500 | 0.8 |  |
| 117 | <0.78 | 50 | 1.56 | 1.56 | 3.12 | 3.12 | 6.25 | 12.5 | 12.5 | 12.5 | 12.5 | 0.8 | 50 |
| 118 | 12.5 | >400 | 50 | 200 | 100 | 200 | 100 | 200 | 200 | 200 | 100 | 1.6 | 50 |
| 119 | 25 | >400 | 200 | 400 | >400 | >400 | 400 | >400 | >400 | >400 | 200 | 1.6 | 100 |
| 121 | 6 | >400 | 50 | 100 | 100 | 200 | 25 | 100 | 100 | 100 | 100 | <0.8 | 100 |
| 122 | 12.5 | >400 | 50 | 200 | 100 | 400 | 50 | 100 | 200 | 400 | 400 | 1.6 | 100 |
| 123 | 3.12 | >400 | 25 | 12.5 | 50 | 100 | 50 | 100 | 50 | 100 | 25 | <0.8 | 200 |
| 124 | 3.12 | >400 | 12.5 | 25 | 50 | 50 | 50 | 50 | 50 | 100 | 25 | <0.78 | 200 |
| 125 | 3.12 | >400 | 25 | 50 | 50 | 100 | 200 | 100 | 50 | 100 | 50 | 3.12 | 200 |
| 126 | 12.5 | >400 | 50 | 50 | 100 | 100 | 100 | 200 | 100 | 200 | 100 | 1.56 | 200 |
| 127 | 0.78 | 50 | 3.12 | 1.56 | 3.12 | 6.25 | 12.5 | 12.5 | 12.5 | 25 | 12.5 | <0.78 | 25 |
| 128 | 0.78 | 50 | 1.56 | <0.78 | 1.56 | 6.25 | 6.25 | 6.25 | 6.25 | 12.5 | 12.5 | <0.78 | 50 |
| 129 | 0.78 | 50 | 1.56 | 1.56 | 3.12 | 6.25 | 6.25 | 6.25 | 12.5 | 12.5 | 6.25 | <0.78 | 50 |
| 130 | 12.5 | >400 | 100 | 100 | 200 | >400 | 25 | 50 | 200 | 200 |  | <0.8 | 50 |
| 131 | 0.8 | 20–100 | <0.8 | <0.8 | 0.8–4 | 0.8–4 | 0.8–4 | 4–20 | 0.8–4 | 0.8–4 | 20–100 | <0.8 | 4–20 |
| 132 | 0.8 | >400 | 0.8–4 | <0.8 | 4–20 | 0.8–4 | 4–20 | 20–100 | 4–20 | 4–20 | 20–100 | <0.8 | 4–20 |
| 134 | 3.1 | >400 | 25 | 25 | 12.5 | 50 | 50 | 200 | 100 | 50 | 200 | 3.1 | 100 |
| 135 | 12.5 | 400 | 50 | 25 | 25 | 100 | 100 | 400 | 400 | 100 | 100 | <0.8 | 200 |
| 138 | 6.25 | 200 | 25 | 12.5 | 25 | 100 | 50 | 50 | 25 | 100 | 12.5 | <0.8 | 50 |
| 140 | 0.8 | 50 | 3.1 | 1.6 | 3.1 | 6.25 | 12.5 | 25 | 12.5 | 12.5 |  | <0.8 | 12.5 |
| 141 | 0.8 | 50 | 3.1 | 1.6 | 3.1 | 3.1 | 6.25 | 12.5 | 12.5 | 6.25 |  |  |  |
| 142 | 0.8 | 50 | 3.1 | 1.6 | 3.1 | 12.5 | 12.5 | 25 | 25 | 12.5 |  | <0.8 | 25 |
| 143 | 12.5 | >400 | 50 | 50 | 200 | 400 | 50 | 100 | 200 | 200 |  | <0.8 | 100 |
| 144 | 1.56 | 400 | 6.25 | 50 | 12 | 25 | 50 | 50 | 6.25 | 12.5 | 200 | <0.8 | 25 |
| 147A | 12.5 | >400 | 50 | 100 | 50 | 200 | 200 | 100 | 25 | 200 | 100 | <0.8 | 50 |

The activity spectrum includes both Gram-negative and Gram-positive bacteria. The particular advantage of the penicillins according to the invention is that they are effective both in vitro (Tables 1 and 2) and in animal experiments (Table 3) against ampicillin-resistant and carbenicillin-resistant *Klebsiella* bacteria and against ampicillinresistant *Proteus* bacteria. Furthermore, they act on ampicillin-resistant *Pseudomonas* varieties in vitro and in vivo. The concentrations required for destroying the bacteria are reached in the serum after parenteral administration (Table 4). Table 5 shows the decrease in the number of ampicillin-resistant *Proteus* bacteria present in the blood after intraperitoneal infection and subcutaneous administration of 50,000 units/kg of penicillin. The excellent effect of some of the new penicillins against Gram-positive bacteria is shown in Table 3. The excellent effect is achieved both on a single administration and also on multiple administration. The resorption of the new penicillins often takes place very rapidly after subcutaneous administration (Table 4), and the peak values are often reached within 10 minutes. Elimination is equally rapid in both these cases. The substances according to the invention are stable to acid; as examples, penicillins No. 59, No. 66 and No. 83 may be quoted, which remain microbiologically active at pH 1 for over one hour. Table 6 shows that the new penicillins are excellently tolerated, which is shown particularly clearly by the extremely high dose which is tolerated without complications on intravenous administration into the vein of the tail. Penicillin No. 66 may here be very particularly quoted as an example.

The experiments on animals (see Table 3) were carried out with white mice of the CF1 strain. The infection took place intraperitoneally with the particular bacterium indicated.

Table 3

Number of surviving mice in % after intraperitoneal infection and subcutaneous therapy, 30 minutes and 90 minutes after infection

| Penicillin No:- | Dose 2 × 3000 units/mouse E.coli C 165 (Ampicillin-sensitive) | | | | 2 × 200 units/mouse Staph. aureus 133 (Ampicillin-sensitive) | | | | 4 × 3000 units/mouse Psdm. aerug. Walter (Ampicillin-resistant) | | | | 2 × 3000 units/mouse Klebsiella 63 (Ampicillin- and Carbenicillin-resistant) | | | | 2 × 3000 units/mouse Proteus vulg. (Ampicillin-resistant) | | | |
|---|---|---|---|---|---|---|---|---|---|---|---|---|---|---|---|---|---|---|---|---|
| | 1 day | 2 days | 3 days | 5 days | 1 day | 2 days | 3 days | 5 days | 1 day | 2 days | 3 days | 5 days | 1 day | 2 days | 3 days | 5 days | 1 day | 2 days | 3 days | 5 days |
| 59 | 70 | 60 | 60 | 60 | 90 | 70 | 70 | 70 | | | | | 100 | 90 | 30 | | 100 | 100 | 100 | 100 |
| 90 | 100 | 90 | 90 | 90 | | | | | | | | | 90 | 70 | 0 | | 100 | 80 | 80 | 80 |
| 62 | 80 | 70 | | | | | | | | | | | 100 | 100 | 40 | | 70 | 50 | 50 | 50 |
| 63 | 80 | 60 | 60 | 60 | | | | | | | | | 100 | 100 | 30 | | 80 | 70 | 70 | 70 |
| 65 | 90 | 60 | 60 | 60 | 90 | 80 | 70 | 70 | | | | | 100 | 100 | 10 | | 100 | 100 | 100 | 100 |
| 73 | 70 | 50 | 40 | 40 | 80 | 70 | 50 | 40 | 50 | 30 | 10 | | 100 | 80 | 0 | | 100 | 100 | 100 | 100 |
| 66 | 100 | 60 | 50 | 50 | 100 | 90 | 70 | 70 | 30 | | | | 90 | 90 | 0 | | 100 | 100 | 100 | 100 |
| 67 | 80 | 50 | 40 | 40 | | | | | 50 | | | | 100 | 80 | 10 | | 100 | 100 | 100 | 90 |
| 83 | 90 | 60 | 60 | 60 | 80 | 70 | 70 | 70 | 70 | 20 | | | 100 | 100 | 60 | | 100 | 100 | 100 | 100 |
| 94 | 50 | 30 | 30 | 30 | | | | | | | | | 80 | 30 | | | 100 | 100 | 100 | 100 |
| 75 | 90 | 80 | 80 | 80 | | | | | | | | | 100 | 100 | 100 | 20 | 60 | 10 | | |
| Ampicillin | 100 | 100 | 100 | 100 | 100 | 100 | 100 | 100 | | | | | 0 | 0 | 0 | 0 | 0 | 0 | 0 | 0 |
| Carbenicillin | | | | | | | | | | | | | 0 | 0 | 0 | 0 | 100 | 100 | 100 | 100 |

Number of surviving mice in % (after intraperitoneal infection and subcutaneous therapy) after the indicated number of days.

| Bacterial Strains | Penicillin | Dose* | 1st | 2nd | 3rd | 5th day |
|---|---|---|---|---|---|---|
| E.coli C 165 | No:-144 | A | 80 | 80 | 80 | 80 |
| E.coli C 165 | Carbenicillin | A | 70 | 50 | 50 | 50 |
| Prot.vulg. 1017 I | No:-144 | A | 70 | 50 | 50 | 50 |
| | Carbenicillin | A | 50 | 50 | 50 | 50 |
| | Ampicillin | A | 0 | 0 | 0 | 0 |
| | No:-147 | B | 100 | 100 | 100 | 100 |
| Klebsiella 63 | No:-144 | B | 70 | 30 | 0 | |
| | Carbenicillin | B | 0 | | | |
| | Ampicillin | B | 0 | | | |
| | Cephalothin | B | 0 | | | |
| | No:-147 | C | 100 | 100 | 40 | 10 |
| Pseudm.aer. Walter | No:-144 | D | 100 | 20 | 20 | 20 |
| | Carbenicillin | D | 80 | 20 | 20 | 20 |
| | Ampicillin | D | 0 | | | |
| | Cephalothin | D | 0 | | | |
| Pseudomon. aer. F 41 | No:-144 | E | 100 | | | |
| | Carbenicillin | E | 0 | | | |
| Pseudomon. aer. F 41 | No:-144 | F | 100 | | | |
| | Carbenicillin | F | 20 | | | |
| Pseudomon. aer. F 41 | No:-144 | G | 100 | | | |
| | Carbenicillin | G | 70 | | | |
| Pseudomon. aer. F 41 | No:-144 | H | 100 | | | |
| | Carbenicillin | H | 70 | | | |
| Klebsiella 63 | No:-144 | A | 30 | | | |
| | Carbenicillin | A | 0 | | | |
| Klebsiella 63 | No:-144 | B | 100 | | | |
| | Carbenicillin | B | 0 | | | |
| Klebsiella 63 | No:-144 | C | 100 | | | |
| | Carbenicillin | C | 0 | | | |

*Dose A = 37,500 units/kg, 30 and 90 minutes after infection
Dose B = 75,000 units/kg, 30 and 90 minutes after infection
Dose C = 150,000 units/kg, 30 and 90 minutes after infection
Dose D = 150,000 units/kg, 0.5, 2, 4 and 6 hours after infection
Dose E = 50,000 units/kg, 30 minutes before and 2, 4 and 6 hours after infection
Dose F = 75,000 units/kg, 30 minutes before and 2, 4 and 6 hours after infection
Dose G = 150,000 units/kg, 30 minutes before and 2, 4 and 6 hours after infection
Dose H = 200,00 units/kg, 30 minutes before and 2, 4 and 6 hours after infection.

Table 4

Serum level after subcutaneous ("s.c.") administration to white mice, in units/ml of serum, measured from the microbiological activity against *Proteus vulgaris* 1017 (ampicillin-resistant).

| Penicillin No:- | Dose (s.c.) | Concentration in the serum; number of minutes after administration of the dose | | | | |
|---|---|---|---|---|---|---|
| | | 10 mins. | 15 mins. | 20 mins. | 30 mins. | 60 mins. |
| 59 | 150,000 units | | 25 units | | 20 units | <2 units |
| 64 | 50,000 units | 50 units | | 10 units | | |
| 64 | 150,000 units | | 42 units | | 26 units | <10 units |

Table 5

Reduction in number of bacteria/ml of blood after subcutaneous administration of Penicillin No. 83
Infection took place intraperitoneally with *Proteus vulgaris* 1017, 8 × 10$^5$/mouse; ampicillin-resistant.

| | Number of bacteria after infection, measured after infection: | | | | | |
|---|---|---|---|---|---|---|
| | 30 mins. | 60 mins. | 90 mins. | 120 mins. | 150 mins. | 180 mins. |
| Control | 3 × 10$^4$ | 2 × 10$^4$ | 2 × 10$^4$ | — | 7 × 10$^4$ | 5 × 10$^4$ |
| Administration of: 1 × 50,000 units/kg subcutaneously, 30 minutes after infection | 9 × 10$^3$ | 7 × 10$^3$ | 2 × 10$^3$ | 1 × 10$^3$ | 3 × 10$^3$ | 8 × 10$^3$ |
| Administration of: 1 × 50,000 units/kg subcutaneously, after 30 minutes, and a further 50,000 units/kg after 90 minutes. | 2 × 10$^4$ | 8 × 10$^3$ | approx. 5 × 10$^3$ | 2 × 10$^2$ | <10$^1$ | <10$^1$ |

The Table shows that a dose of 50,000 units/kg, administered subcutaneously, already drastically reduces the numer of bacteria in the blood; additionally, it shows that the double subcutaneous administration of 50,000 units/kg causes elimination of the bacteria.

Table 6

| Penicillin No. | Acute toxicity (LD$_{50}$) in white mice after intravenous injection into the vein of the tail, in mg/kg |
|---|---|
| 66 | >4000 |
| 60 | 1500 |
| 86 | >3000 |
| 83 | >1200 |
| 94 | 4000 |
| 75 | 1500 |
| Carbenicillin | 2700 |
| Dicycloxacillin | 900 |

The comparison shows that the new penicillins are clearly superior to the commercially available products dicycloxacillin and carbenicillin on intravenous injection of a single dose.

The invention further relates to the pharmaceutical use of the new penicillins and their pharmaceutically acceptable salts.

Accordingly, the present invention provides an antibiotic pharmaceutical composition containing as an active ingredient at least one of the penicillins of the formula (1), or a pharmaceutically acceptable non-toxic salt thereof in combination with a pharmaceutically acceptable solid or liquid diluent or carrier as hereinafter defined.

In the present specification the expression "pharmaceutically acceptable diluent or carrier" means a non-toxic substance that when mixed with the active ingredient or ingredients renders it suitable for administration. The expression preferably excludes water and low-molecular weight organic solvents commonly used in chemical synthesis, except in the presence of other pharmaceutically necessary ingredients such as salts in correct quantities to render the composition isotonic, buffers, surfactants, coloring and flavoring agents, and preservatives. Examples of suitable liquid diluents and carriers are vegetable oils, polyols, buffered aqueous solutions, isotonic saline aqueous solutions, syrups and lotion bases. Examples of suitable solid diluents and carriers are starches, cellulose and its derivatives, sugars, stearates and stearic acid, talc, certain types of alumina, and ointment bases. Examples of pharmaceutical compositions according to the invention are ointments, pastes, creams, sprays, lotions, aqueous suspensions, elixirs, syrups, drops, granules and powders, either free-flowing or compressed into tablets.

The penicillins and pharmaceutically acceptable salts of the present invention may be administered perorally.

One group of preferred pharmaceutical compositions of the invention are therefore those adapted for oral administration. The diluents and carriers used are preferably therefore those that adapt the active ingredient or ingredients for oral administration. Examples of such diluents and carriers are solid vehicles, excipients and lubricants such as glucose, lactose and sucrose, corn and potato starch, sodium carboxymethyl cellulose, ethyl cellulose and cellulose acetate, powdered gum tragacanth, gelatin, alginic acid, agar, stearic acid, sodium calcium and magnesium stearates, sodium lauryl sulphate, polyvinylpyrollidone, sodium citrate, calcium carbonate, dicalcium phosphate, and certain types of alumina.

The pharmaceutical compositions of the invention may also contain other non-toxic adjuvants and modifiers such as dyes, surfactants, perfumes, flavoring agents, preservatives and biocides.

The compounds of the present invention may also be administered parenterally for example by intramuscular, subcutaneous or intravenous injection, or, if necessary, as a continuous drip infusion. A group of preferred pharmaceutical compositions of the invention are therefore those adapted for parenteral injection. The diluents and carriers used are therefore preferably those that adapt the active ingredient for parenteral administration. Examples of such diluents and carriers are solvents and suspending diluents such as water and water-miscible organic solvents, in particular sesame oil, groundnut oil, aqueous propylene glycol, and N,N'-dimethyl formamide. A preferred example of a pharmaceutical composition of the invention adapted for parenteral administration is a sterile isotonic saline aqueous solution of the active ingredient, which may be buffered with a pharmaceutically acceptable buffer. The solution may be rendered isotonic in any known manner, for example by the incorporation of sodium chloride and/or glucose. Such solutions can be administered as a single dose or as a continuous drip infusion, or divided into a series of doses.

In oral and parenteral administration a dose of 25,000 to 1,000,000 units per kg. body weight is appropriate.

The present invention also provides antibiotic medicaments in dosage unit form as hereinafter defined comprising as an active ingredient at least one penicillin of formula (1), or a pharmaceutically acceptable non-toxic salt thereof, either alone or in combination with a pharmaceutically acceptable solid or liquid diluent or carrier. In this case the diluent or carrier is preferably as defined above but can also be water or another common solvent.

The expression "medicament in dosage unit form" as used in the present specification means a medicament in the form of discrete portions each containing a unit dose or a multiple or sub-multiple of a unit dose of the active ingredient(s); for example, one, two, three or four unit doses or a half, a third or a quarter of a unit dose. A "unit dose" is the amount of the active ingredient(s) to be administered on one occasion and will usually be a daily dose, or for example a half, a third, or a quarter of a daily dose depending on whether the medicament is to be administered once or, for example, twice, three times, or four times a day.

The discrete portions constituting the medicament in dosage unit form can include a protective envelope. The active ingredient can be undiluted and contained in such an envelope, or can be mixed with a pharmaceutically acceptable solid or liquid diluent or carrier as defined above. Such portions can for example be in monolithic coherent form, such as tablets, lozenges, pills, suppositories, or dragees; in wrapped or concealed form, the active ingredients being within a protective envelope, such as wrapped powders, cachets, sachets, capsules, or ampoules; or in the form of a sterile solution suitable for parenteral injection, such as ampoules of buffered, isotonic, sterile, pyrogen-free aqueous solution; or in any other form known in the art.

As stated above, oral administration is one preferred form of administration for the penicillins of formula (1) and their pharmaceutically acceptable non-toxic salts. Preferred medicaments in dosage unit form according to the invention are therefore those adapted for oral administration, such as tablets, pills, dragees, capsules, and cachets, as well as wrapped powders containing the active ingredient in powdered form with a powdered diluent or carrier for suspension in water before being taken.

As stated above, another preferred mode of administration for the penicillins and their pharmaceutically acceptable non-toxic salts is parenteral administration. Preferred medicaments in dosage unit form according to the invention are therefore those adapted for parenteral injection, such as ampoules containing a measured quantity of a sterile isotonic saline injectable aqueous solution of the new active ingredient, which may be buffered with a pharmaceutically acceptable buffer. A particularly preferred medicament in dosage unit form according to the invention is dry ampoules each containing a unit dose or a multiple or sub-multiple of a unit dose of one of the new penicillins and pharmaceutically acceptable salts according to the invention. Such ampoules may be used at the place and time of administration for making up parenterally injectable solutions.

The preferred unit dose for parenteral and peroral administration of the medicaments of the invention is 1,250,000 – 90,000,000 units per person of active ingredient.

The following non-limitative examples more particularly illustrate the present invention.

The $\alpha$-aminobenzylpenicillin (ampicillin) used in the examples contained about 14% of water, but anhydrous $\alpha$-aminobenzylpenicillin [compare U.S. Pat. No. 3,144,445] can be used equally well.

Unless expressly stated otherwise, "ampicillin" denotes the $\alpha$-aminobenzylpenicillin having the D(—)- = R-configuration in the side chain.

The $\beta$-lactam content of the penicillins was determined iodometrically in the following Examples. All substances described here showed an IR spectrum corresponding to their structure. The NMR spectra of the penicillins were recorded in $CD_3OD$ solution; the signals indicated in the Examples correspond to the $\tau$-scale; they agree with the particular structure.

The figures quoted in the Examples for the effectiveness against certain bacteria (units/ml) are minimum inhibitory concentrations in the test tube series dilution test after 24 hours' incubation.

In the case of the data: "Effectiveness in Animal Experiments", A denotes that the particular penicillin is more effective than ampicillin when used subcutaneously in mice against *Proteus vulgaris* 1017, and B denotes that it is more effective than ampicillin and carbenicillin against *Klebsiella aerobacter* 63.

EXAMPLE 1

Sodium D(—)-$\alpha$-(3-acetyl-3-allyl ureido)-benzylpenicillin:

5.5 parts by weight of D(—)-$\alpha$-(3-acetyl-3-allyl-ureido)-$\alpha$-phenylacetic acid were dissolved in 50 parts by volume of dichloromethane, with exclusion of moisture, and 2.0 parts by weight of triethylamine were added while cooling. The mixture was now cooled to between —5° and —10° C, and 3.6 parts by weight of tetramethylchloroformamidinium chloride were added as several portions over the course of a few minutes. Thereafter, the mixture was stirred for 30 minutes at this temperature and any insoluble matter was filtered off without the solution rising to above 0° C. The filtrate was cooled to −10° C and added all at once to a solution of 4.1 parts by weight of 6-aminopenicillanic acid and 3.4 parts by weight of triethylamine in 50 parts by volume of dichloromethane, cooled to −10° C. [The aminopenicillanic acid was stirred for 1.5 hours at room temperature with the triethylamine and 2 parts by weight of a molecular sieve (Zeolite VS 10-2) which had been ground in a mortar; thereafter, the mixture was filtered while excluding moisture, and the filtrate was employed for the reaction]. The combined solutions were left to stand for one hour at 0° C and subsequently poured into 100 parts by volume of water. The pH value was adjusted to 6.5, the dichloromethane phase was separated off, and the aqueous phase was covered with 200 parts by volume of a 1:1 mixture of ethyl acetate and ether. Sufficient 2 N hydrochloric acid was added, while stirring vigorously and cooling with ice, to obtain a pH value of 2.0 in the aqueous layer. The organic phase was separated off, washed with 2 × 40 parts by volume of water and dried for two hours over $MgSO_4$ in a refrigerator. 20 parts by volume of a 1 M solution of sodium 2-ethylhexanoate in ether containing methanol were now added, the mixture was largely concentrated in vacuo at 0° C, the residue was taken up in just sufficient methanol, and the sodium salt of the penicillin was precipitated by adding excess ether whilst shaking vigorously.

Yield: 67%.

β-Lactam content: 81%.

|  | C | H | N | S |
|---|---|---|---|---|
| Calculated: | 51.4 | 5.3 | 10.9 | 6.2 |
| Found: | 51.5 | 6.0 | 10.3 | 5.5 |

According to the IR spectrum and thin layer chromatogram, the product was identical with a comparison sample prepared from ampicillin and N-acetyl-N-allyl-carbamic acid chloride.

EXAMPLE 2

Sodium D(−)-α-(3-γ-chlorobutyryl-3-methyl-ureido)-benzylpenicillin:

A solution was prepared, as described in Example 1, from 6.25 parts by weight of D(−)-α-(3-γ-chlorobutyryl-3-methylureido)-phenylacetic acid and 3.6 parts by weight of tetramethylchloroformamidinium chloride, and was kept for 1.5 hours at −5° to −10° C. Thereafter it was combined with a solution of 4.1 parts by weight of 6-aminopenicillanic acid and 3.5 parts by weight of triethylamine in dichloromethane, which was stored for one hour at room temperature. Thereafter the mixture was worked up as described in Example 1.

Yield: 62%

β-Lactam content: 84%

|  | C | H | Cl | N | S |
|---|---|---|---|---|---|
| Calculated: | 48.0 | 5.1 | 6.4 | 10.2 | 5.8 |
| Found: | 48.1 | 5.2 | 5.8 | 9.9 | 6.4 |

NMR signals at τ = 2.3–2.9 (5 H), 4.45 (1 H), 4.55 (2 H), 5.8 (1 H), 6.4 (2 H), 6.75 (3 H), 7.3 (2 H), 7.9 (2H) and 8.5 ppm (6 H).

EXAMPLE 3

If, in the procedure of Example 2, the D(−)-α-(3-γ-chlorobutyryl-3-methylureido)-phenylacetic acid used there is replaced by 0.02 mol of:
D(−)-α-(3-β-chloropropionyl-3-methyl-ureido)-phenylacetic acid,
D(−)-α-(3-γ-trifluorobutyryl-3-methyl-ureido)-phenylacetic acid,
D(−)-α-(3-γ-trichlorobutyryl-3-methyl-ureido)-phenylacetic acid,
D(−)-α-(3-γ-trichlorobutyryl-3-β-chloroethyl-ureido)-phenylacetic acid,
D(−)-α-(3-cinnamoyl-3-methyl-ureido)-phenylacetic acid,
D(−)-α-(3-[1,2,5,6,-tetrahydrobenzoyl]-3-methyl-ureido)-phenylacetic acid or
D(−)-α-(3-hexahydrobenzoyl-3-methyl-ureido)-phenylacetic acid, the following penicillins are obtained in the form of their sodium salts:
D(−)-α-(3-β-chloropropionyl-3-methyl-ureido)-benzylpenicillin,
D(−)-α-(3-γ-trifluorobutyryl-3-methyl-ureido)-benzylpenicillin,
D(−)-α-(3-γ-trichlorobutyryl-3-methyl-ureido)-benzylpenicillin,
D(−)-α-(3-γ-trichlorobutyryl-3-β-chloroethyl-ureido)-benzylpenicillin,
D(−)-α-(3-cinnamoyl-3-methyl-ureido)-benzylpenicillin,
D(−)-α-(3-[1,2,5,6-tetrahydrobenzoyl]-3-methyl-ureido)-benzylpenicillin
or D(−)-α-(3-hexahydrobenzoyl-3-methyl-ureido)-benzylpenicillin.

EXAMPLE 4

Sodium D,L-α-(3-benzoyl-3-methyl-ureido)-p-methylbenzyl-penicillin:

This penicillin was prepared, as described in Examples 1 and 2, from 5.5 parts by weight of D,L-α-(3-benzoyl-3-methyl-ureido)-p-tolyl-acetic acid, 3 parts by weight of tetramethyl-chloroformamidinium chloride and 4.35 parts by weight of 6-aminopenicillanic acid.

Yield: 59%.

β-Lactam content: 84%.

|  | C | H | N | S |
|---|---|---|---|---|
| Calculated: | 54.4 | 5.3 | 9.7 | 7.9 |
| Found: | 54.9 | 5.9 | 9.5 | (5.6) |

NMR signals at τ = 2.5 (5 H), 2.5–3.0 (4 H), 4.3–4.65 (3.0 H), 5.8 (1 H), 6.9 (3 H), 7.7 (3 H) and 8.2–8.5 ppm (6 H).

Effectiveness in Animal Experiments: A and B.

EXAMPLE 5

Sodium D,L-(3-γ-chlorobutyryl-3-methyl-ureido)-(2-thienyl)-methylpenicillin

This penicillin was prepared, in the manner described in Examples 1 and 2, from 5.9 parts by weight of D,L-(3-γ-chlorobutyryl-3-methyl-ureido)-(2-thienyl)-acetic acid, 3.5 parts by weight of tetramethylchloroformamidinium chloride and 4.06 parts by weight of 6-aminopenicillanic acid.
Yield: 64%.
β-Lactam content: 95.5%.
NMR signals at τ = 2.5–3.2 (3 H), 4.1 (1 H), 4.4 (2 H), 5.8 (1 H), 6.3 (2 H), 6.7 (3 H), 7.2 (2 H), 7.9 (2 H) and 8.4 ppm (6 H).
Effectiveness in Animal Experiments: B.

EXAMPLE 6

If, in the procedure of Example 1, the D(−)-α-(3-acetyl-3-allyl-ureido)-phenylacetic acid used there is replaced by: 0.02 mol of:

α-(3-acetyl-3-methyl-ureido)-p-tolylacetic acid,
α-(3-acetyl-3-methyl-ureido)-p-chlorophenylacetic acid,
α-(3-acetyl-3-methyl-ureido)-p-methylsulphenyl-phenylacetic acid,
α-(3-acetyl-3-methyl-ureido)-p-methoxyphenylacetic acid,
α-(3-acetyl-3-methyl-ureido)-o-chlorophenylacetic acid,
α-(3-acetyl-3-methyl-ureido)-m-iodo-phenylacetic acid,
α-(3-acetyl-3-methyl-ureido)-2,6-dichloro-phenylacetic acid,
α-(3-acetyl-3-methyl-ureido)-2,6-dimethoxy-phenylacetic acid,
α-(3-acetyl-3-methyl-ureido)-2,4-dibromo-phenylacetic acid,
α-(3-acetyl-3-methyl-ureido)-m-methyl-phenylacetic acid,
α-(3-acetyl-3-methyl-ureido)-2,6-dimethyl-phenylacetic acid,
α-(3-acetyl-3-methyl-ureido)-2-chloro-6-fluoro-phenylacetic acid
α-(3-acetyl-3-methyl-ureido)-2-thienyl-acetic acid,
or α-(3-acetyl-3-methyl-ureido)-3-thienyl-acetic acid,
the sodium salts of the following penicillins are obtained:

α-(3-acetyl-3-methyl-ureido)-p-methylbenzylpenicillin,
α-(3-acetyl-3-methyl-ureido)-p-chloro-benzyl-penicillin,
α-(3-acetyl-3-methyl-ureido)-p-methylsulphenyl-benzylpenicillin,
α-(3-acetyl-3-methyl-ureido)-p-methoxybenzyl-penicillin,
α-(3-acetyl-3-methyl-ureido)-o-chlorobenzylpenicillin,
α-(3-acetyl-3-methyl-ureido)-m-iodobenzylpenicillin,
α-(3-acetyl-3-methyl-ureido)-2,6-dichlorobenzyl-penicillin,
α-(3-acetyl-3-methyl-ureido)-2,6-dimethoxybenzyl-penicillin,
α-(3-acetyl-3-methyl-ureido)-2,4-dibromobenzyl-penicillin,
α-(3-acetyl-3-methyl-ureido)-m-methylbenzyl-penicillin,
α-(3-acetyl-3-methyl-ureido)-2,6-dimethyl-benzyl-penicillin,
α-(3-acetyl-3-methyl-ureido)-2-chloro-6-fluoro-benzylpenicillin,
α-(3-acetyl-3-methyl-ureido)-α-2-thienylmethyl-penicillin or
α-(3-acetyl-3-methyl-ureido)-α-3-thienylmethyl-penicillin.

EXAMPLE 7

Sodium D(−)-α-(3-methoxycarbonyl-3-methyl-ureido)-2,6-dichlorobenzylpenicillin 1.35 parts by weight of tetramethylchloroformamidinium chloride were dissolved in 15 parts by volume of dichloromethane and cooled to 0° C while excluding moisture. 2.4 parts by weight of D(−)-α-(3-methoxycarbonyl-3-methyl-ureido)-2,6-dichloro-phenylacetic acid, in a little methylene chloride, were added to this solution. A solution of 1.04 parts by volume of triethylamine in 5 parts by volume of dichloromethane was now added dropwise at −5° C over the course of 30 minutes. After a further 40 minutes at −5° C, the mixture was combined with a solution of the triethylamine salt from 2.22 parts by weight of 6-aminopenicillanic acid and 1.6 parts by volume of triethylamine in 25 parts by volume of dichloromethane, cooled to −20° C. The mixture was now stirred for 30 minutes at 0° C, with a further 0.4 part by volume of triethylamine being added after 15 minutes. Thereafter, the mixture was stirred for a further 30 minutes at room temperature and poured into water, the aqueous layer was separated off at pH 6.5, and the sodium salt of the penicillin was isolated as described in Example 1.
Yield: 28%.
β-Lactam content: 94%.
NMR signals at τ = 2.6 (2.1 H), 2.7 (0.9 H), 3.4 (0.7 H), 3.8 (0.3 H), 4.35-4.50 (2 H), 5.8 (1 H), 6.15 (3 H), 6.8 (2.1 H), 6.85 (0.9 H) and 8.45 ppm (6 H).

EXAMPLE 8

Sodium L(+)-α-(3-methoxycarbonyl-3-methyl-ureido)-2,6-dichlorobenzylpenicillin

This penicillin was prepared, in the manner described in Example 7, from 3.1 parts by weight of L(+)-α-(3-methoxycarbonyl-3-methyl-ureido)-2,6-dichloro-phenylacetic acid, 1.74 parts by weight of tetramethyl-chloroformamidinium chloride and 2.87 parts by weight of 6-aminopenicillanic acid.
Yield: 47%
β-Lactam content: 92%
NMR signals at τ = 2.6 (1.8 H), 2.7 (1.2 H), 3,35 (0.6 H) 3.8 (0.4 H), 4.4 (2 H), 5.75 (1 H), 6.15 (3 H), 6.8 (1.8 H), 6.85 (1.2 H), and 8.4 ppm (6 H).

EXAMPLE 9

Sodium D,L-α-(3-methoxycarbonyl-3-methyl-ureido)-2,6-dichlorobenzylpenicillin

A solution of 5.0 parts by weight of D,L-α-(3-methoxycarbonyl-3-methylureido)-2,6-dichloro-phenylacetic acid in 10 parts of volume of acetone was added dropwise, at 0° C, to a suspension of 3.0 parts by weight of finely ground tetramethylchloroformamidinium chloride in 20 parts by volume of dry acetone. After 5 minutes, the mixture was cooled to −5° C and 2.1 parts by volume of triethylamine in 10 parts by volume of acetone were added dropwise, slowly and uniformly, over the course of 30 minutes whilst excluding moisture. The mixture was kept at 0° C for one hour, while stirring, and thereafter the precipitate was filtered off without the solution rising to above 0° C. The filtrate was now added, in several portions, to a solution of 3.23 parts by weight of 6-aminopenicillanic acid in 25 parts by volume of 80% strength aqueous tetrahydrofurane (sufficient 2 N NaOH being added for solution just to occur [pH 8.2]), at 0° C, while keeping the pH value at between 7.5 and 8.0 by adding 2 N NaOH. The mixture was allowed to come to room temperature while stirring, where it was stirred until no further addition of sodium hydroxide solution was necessary for maintaining the pH value of 7.5 to 8.0 (1 to 2 hours). Thereafter, the pH value was lowered to 6.5 with a little dilute hydrochloric acid, 20 parts by volume of water were added, and the tetrahydrofurane was evaporated off in vacuo at room temperature. The aqueous solution which remained was extracted once with 25 parts by volume of ether and covered with 50 parts by volume of a 1:1 mixture of ethyl acetate and ether. The solution was acidified to pH 2.0 with dilute hydrochloric acid while cooling with ice, and the organic phase was separated off. The latter was twice washed with 10 parts by volume of water at a time, dried over $MgSO_4$ for 4 hours at 0° C, and filtered. The sodium salt of the penicillin was precipitated by adding 15 parts by volume of a 1 molar solution of sodium 2-ethyl-hexanoate in ether containing methanol. The solvent was almost completely distilled from the mixture in vacuo at 0° C, the residue was taken up in the minimum possible amount of methanol, and the product was precipitated by adding ether. After standing for one hour at 0° C, it was filtered off, washed with ether containing methanol and subsequently dried for several days over $P_2O_5$ in a vacuum desiccator.

Yield: 71%.

β-Lactam content: 68%.

|  | C | H | Cl | N | S |
|---|---|---|---|---|---|
| Calculated: | 41.3 | 4.2 | 12.2 | 9.6 | 5.5 |
| Found: | 41.1 | 5.0 | 14.0 | 9.0 | 4.9 |

NMR signals at $\tau$ = 2.5 (1.95 H), 2.6 (1.05 H), 3.35 and 3.40 (0.65 H), 3.8 (0.35 H), 4.45 (2 H), 5.8 (1 H), 6.2 (3 H), 6.75 (1.95 H), 6.8 (1.05 H) and 8.4 ppm (6 H).

EXAMPLE 10

A.

D(−)-α-(3-Methoxycarbonyl-3-methyl-ureido)-phenylacetic acid 15.1 parts by weight of D(−)-C-phenylglycine were stirred for 15 minutes with 20:2 parts by weight of triethylamine in 180 parts by volume of a 3:1 mixture of dimethylsulphoxide and water. 15.2 parts by weight of N-methoxy-carbonyl-N-methyl-carbamic acid chloride in 30 parts by volume of dry acetone were now added dropwise within 30 minutes in such a way that the temperature did not exceed 20° C. The mixture was stirred for a further 2 hours, 200 parts by volume of water were then added and the whole was acidified to pH 2 with dilute hydrochloric acid. Thereafter the mixture was extracted three times with 120 parts by volume of ethyl acetate at a time, and the organic phase was washed with 50 parts by volume of water and dried over $MgSO_4$. After filtration, the solvent was distilled off in vacuo, the remnants of dimethylsulphoxide were stripped off at 80° C and 0.1 mm Hg. The glassy oil, which was left in 73% yield, was pure methoxycarbonyl-methyl-ureidophenylacetic acid, according to the NMR spectrum.

|  | C | H | N |
|---|---|---|---|
| Calculated: | 54.0 | 5.3 | 10.5 |
| Found: | 54.9 | 5.6 | 9.6 |

NMR signals at $\tau$ = 0.4 (1 H), 2.4–2.8 (5 H), 4.65 (1 H), 6.2 (3 H) and 6.9 ppm (3 H).

B. Sodium D(−)-α-(3-methoxycarbonyl-3-methyl-ureido-benzyl-penicillin

This penicillin was prepared as described in Example 7, from 5.3 parts by weight of D(−)-α-(3-methoxycarbonyl-3-methyl-ureido)-phenylacetic acid, 3.4 parts by weight of tetramethyl chloroformamidinium chloride and 4.0 parts by weight of 6-amino-penicillanic acid. Yield: 63%.

β-Lactam content: 69%.

NMR signals at $\tau$ = 2.3–2.9 (5 H), 4.45 (1 H), 4.5 and 4.55 (2 H), 5.8 (1 H), 6.2 (3 H), 6.85 (3 H) and 8.45 ppm (6 H).

The Table which follows compares the anti-bacterial action of this product (A) with that of the penicillin (B) prepared from ampicillin and N-methoxycarbonyl-N-methyl-carbamic acid chloride, and with the product (C) which was prepared according to the instructions of Example 27:

| Type of Bacterium | Effectiveness [units /ml] | | |
|---|---|---|---|
|  | (A) | (B) | (C) |
| Escherichia coli 14 | 12.5 | 6.25 | 100 |
| Escherichia coli 183/58 | 50 | 25 | 200 |
| Pseudomonas aerug. Bonn | 50 | 25 | 400 |
| Pseudomonas aerug. Walter | 50 | 25 | 400 |
| Klebsiella K 10 | 200 | 200 | 400 |
| Klebsiella 63 | 200 | 200 | 400 |
| Staphylococcus aureus 133 | 1.56 | 1.56 | 6.25 |

EXAMPLE 11

A. D(−)-α-(3-Isopropoxycarbonyl-3-methyl-ureido)-phenylacetic acid 15.1 parts by weght of D(−)-C-phenylglycine were dissolved in 250 parts by volume of 50% strength aqueous dioxane by adding sufficient dilute sodium hydroxide solution. Thereafter the pH value was lowered to 7.8 with 2 N HCl, whereupon a part of the phenylglycine precipitated in a finely divided form. The mixture was cooled to 0° C and 18.0 parts by weight of N-isopropoxycarbonyl-N-methylcarbamic acid chloride in 30 parts by volume of anhydrous dioxane were added dropwise over the course of 30 minutes, the pH value of 7.5–8.0 being maintained by simultaneous addition of 2 N sodium hydroxide solution. The mixture was subsequently stirred at room temperature until no further addition of alkali was necessary for keeping the pH constant. 300 parts by volume of water were now added and the solution was extracted once with 150 parts by volume of ether. Thereafter it was acidified to pH = 2 with 2 N NCl, and the oil which precipitated was taken up in several portions of ethyl acetate. The combined organic solutions were washed once with 100 parts by volume of water and were dried for some hours over MgSO$_4$. After filtration, they were evaporated, and the oily residue was freed of dioxane at 60°–80° C and 0.1 mm Hg. The glassy product was obtained in 48% yield. It was completely pure, according to the NMR spectrum and the thin layer chromatogram.

|  | C | H | N |
|---|---|---|---|
| Calculated: | 57.1 | 6.1 | 9.5 |
| Found: | 56.9 | 5.7 | 9.8 |

NMR signals at $\tau$ = 0.3 (1 H), +0.4 (1 H), 2.3–2.8 (5 H), 4.6 (1 H), 5.0 (1 H), 6.9 (3 H) and 8.75 ppm (6 H).

B. The following α-ureido-arylacetic acids were prepared as described in Example 11A:

1. D(−)-α-(3-Acetyl-3-allyl-ureido)-phenylacetic acid from 8.1 parts by weight of N-acetyl-N-allylcarbamic acid chloride and 7.5 parts by weight of D(−)-C-phenylglycine.
Yield: 100%.

|  | C | H | N |
|---|---|---|---|
| Calculated: | 60.8 | 5.9 | 10.1 |
| Found: | 60.3 | 6.1 | 9.8 |

NMR signals at $\tau$ = 0.0 (1 H), 2.6 (5 H), 3.75–4.5 (1 H), 4.6 (1 H), 4.7–5.15 (2 H), 5.5–5.9 (2 H) and 7.7 ppm (3 H).

2. D(−)-α-(3-γ-Chlorobutyryl-3-methyl-ureido)-phenylacetic acid from 9.9 parts by weight of N-γ-chlorobutyryl-N-methylcarbamic acid chloride and 7.5 parts by weight of D(−)-C-phenyl-glycine.
Yield: 99%.

|  | C | H | Cl | N |
|---|---|---|---|---|
| Calculated: | 53.8 | 5.5 | 11.3 | 9.0 |
| Found: | 53.9 | 5.8 | 10.8 | 9.4 |

NMR signals at $\tau$ = −0.1 (1 H), 2.6 (5 H), 4.6 (1 H), 6.3 (2 H), 6.8 (3 H), 7.2 (2 H) and 7.9 ppm (2 H).

3. D,L-α-(3-Benzoyl-3-methyl-ureido)-4-tolylacetic acid from 3.2 parts by weight of N-benzoyl-N-methylcarbamic acid chloride and 3.8 parts by weight of D,L-C-(4-tolyl)-glycine.
Yield: 90%.
NMR signals at $\tau$ = 2.5 (5 H), 2.6 (2 H), 2.8 (2 H), 4.5 (1 H), 6.85 (3 H) and 7.7 ppm (3 H).

4. D(−)-α-(3-Methoxycarbonyl-3-methyl-ureido)-2,6-dichloro phenylacetic acid from 1.75 parts by weight of N-acetyl-N-methyl-carbamic acid chloride and 3.31 parts by weight of D(−)-C-(2,6-dichlorophenyl)-glycine hydrobromide. [we assume that the acid, which can be obtained from 2,6-dichlorobenzyldehyde via the hydantoin in a manner which is in itself known, and which after acylation of the amino group and splitting of the racemate with optically active bases, followed by removal of the acylating group, is obtained in a laevorotatory and a dextrorotatory form, belongs, by analogy to the known conditions in the case of C-phenylglycine, to the D-series in the laevo-rotatory form, and to the L-series in the dextro-rotary form].

Yield: 90%. Melting point = 149° C, $[\alpha]_D$ = 28.1°
NMR signals at $\tau$ = 0.2 (1 H), 2.5 (3 H), 3.6 (1 H), 6.2 (3 H) and 6.9 ppm (3 H).

5. L(+)-α-(3-Methoxycarbonyl-3-methyl-ureido)-2,6-dichloro phenylacetic acid from 1.6 parts by weight of N-methoxycarbonyl-N-methylcarbamic acid chloride and 3.01 parts by weight of L(+)-C-(2,6-dichlorophenyl)-glycine hydrobromide.
Yield: 100%, $[\alpha]_D$ = + 29.3°
NMR signals as indicated in Example 9.B.4.

6. D,L-α-(3,Methoxycarbonyl-3-methyl-ureido)-2,6-dichlorophenylacetic acid from 3.03 parts by weight of N-methoxycarbonyl-N-methyl-carbamic acid chloride and 4.4 parts by weight of D,L-C-(2,6-dichlorophenyl)-glycine.
Yield: 78%. Melting point = 216° C.
NMR signals as indicated in Example 9.B.4.

7. D(−)-α-(3-n-Butoxycarbonyl-3-methyl-ureido)-phenylacetic acid from 9.7 parts by weight of N-n-butoxycarbonyl-N-methylcarbamic acid chloride and 7.1 parts by weight of D-C-phenylglycine.
Yield: 100%.

|  | C | H | N |
|---|---|---|---|
| Calculated: | 58.4 | 6.5 | 9.1 |
| Found: | 58.6 | 6.9 | 9.5 |

NMR signals at $\tau$ = 0.5 (1 H), 2.6 (5 H), 4.65 (1 H), 5.8 (2 H), 6.9 (3 H), 8.0–9.0 (4 H) and 9.05 ppm (3 H).

8. D,L-α-(3-Benzoyl-3-allyl-ureido)-4-methoxyphenyl-glycine from 4.5 parts by weight of N-benzoyl-N-allylcarbamic acid choride and 3.6 parts by weight of D,L-C-(4-methoxyphenyl)-glycine.
Yield: 70%.
NMR signals at $\tau$ = 0.6 (1 H), 2.5 (5 H), 2.5 (5 H), 2.7 (2 H), 3.0 (2 H), 3.8-4.5 (1 H), 4.6–5.2 (3 H), 5.6–5.8 (2 H) and 6.2 ppm (3 H).

9. D(−)-α-(3-Acetyl-3-benzyl-ureido)-phenylacetic acid from 8.5 parts by weight of N-acetyl-N-benzyl-carbamic acid chloride and 6.0 parts by weight of D(−)-C-phenylglycine.
Yield: 92%. Melting point = 183°–185° C.

|  | C | H | N |
|---|---|---|---|
| Calculated: | 66.3 | 5.6 | 8.6 |
| Found: | 66.3 | 5.7 | 8.6 |

NMR signals at $\tau$ = −0.1 (1 H), 2.6 (5 H), 2.7 (5 H), 4.55 (1 H), 5.0 (2 H) and 7.8 ppm (3 H).

10. D,L-α-(3-Benzoyl-3-allyl-ureido)-2,6-dichlorophenylacetic acid from 4.5 parts by weight of N-benzoyl-N-allyl-carbamic acid chloride and 4.4 parts by weight of D,L-C-(2,6-dichlorophenyl)-glycine.
Yield: 97%.

|  | C | H | Cl | N |
|---|---|---|---|---|
| Calculated: | 56.0 | 4.0 | 17.4 | 6.9 |
| Found: | 55.6 | 4.4 | 16.0 | 6.5 |

NMR signals at $\tau$ = 0 (1 H), 2.3–2.65 (8 H), 3.6 (1 H), 3.9–4.5 (1 H), 4.8–5.3 (2 H) and 5.6–5.9 ppm (2 H).

11. D,L-α-(3-Acetyl-3-allyl-ureido)-2-thienylacetic acid from 3.2 parts by weight of N-acetyl-N-allylcarbamic acid chloride and 2.9 parts by weight of D,L-C-(2-thienyl)-glycine.
Yield: 99%.
NMR signals at $\tau$ = 2.5–3.1 (3 H), 3.7–4.4 (1 H), 4.3 (1 H), 4.6–5.1 (2 H), 5.5–5.7 (2 H) and 7.7 ppm (3 H).

12. D,L-α-(3-Dimethylaminocarbonyl-3-methyl-ureido)-2,6-dichloro-phenylacetic acid from 3.3 parts by weight of N-dimethylamino-carbonyl-N-methyl-carbamic acid chloride and 4.4 parts by weight of D,L-C-(2,6-dichlorophenyl)-glycine.
Yield: 86%. Melting point = 205° C.
NMR signals at $\tau$ = 1.6 (1 H), 2.5 (3 H), 3.7 (1 H), 7.0 (3 H) and 7.1 ppm (6 H).

13. D,L-α-(3-Methoxycarbonyl-3-methyl-ureido)-4-methoxyphenylacetic acid from 3.0 parts by weight of N-methoxycarbonyl-N-methylcarbamic acid chloride and 3.6 parts by weight of D,L-C-(4-methoxyphenyl)-glycine.
Yield: 87%.
NMR signals at $\tau$ = 2.6 (2 H), 3.05 (2 H), 4.6 (1 H), 6.2 (6 H) and 6.8 ppm (3 H).

14. D,L-α-(3-Dimethylaminocarbonyl-3-methyl-ureido)-4-methoxyphenylacetic acid from 3.3 parts by weight of N-dimethylamino-carbonyl-N-methylcarbamic acid chloride and 3.6 parts by weight of D,L-C-(4-methoxyphenyl)-glycine.
Yield: 100%.
NMR signals at $\tau$ = 2.0 (1 H), 2.6 (2 H), 3.05 (2 H), 4.6 (1 H), 6.2 (3 H), 6.95 (3 H) and 7.1 ppm (6 H).

15. D,L-α-(3-Methoxycarbonyl-3-methyl-ureido)-2-thienyl acetic acid from 3.0 parts by weight of N-methoxycarbonyl-N-methylcarbamic acid hydrochloride and 2.9 parts by weight of D,L-C-(2-thienyl)-glycine.
Yield: 100%.
NMR signals at $\tau$ = 0.4 (1 H), 2.5–3.1 (3 H), 4.25 (1 H), 6.2 (3 H) and 6.8 ppm (3 H).

16. D,L-α-(3-Dimethylaminocarbonyl-3-methyl-ureido)-phenylacetic acid from 3.3 parts by weight of N-dimethylamino-carbonyl-3-methyl-carbamic acid chloride and 2.9 parts by weight of D,L-C-(2-thienyl)-glycine.
Yield: 84%.
NMR signals at $\tau$ = 1.9 (1 H), 2.5–3.1 (3 H), 4.3 (1 H), 6.9 (3 H) and 7.1 ppm (6 H)

17. D,L-α-(3-Benzoyl-3-allyl-ureido)-α-2-thienylacetic acid from 4.5 parts by weight of N-benzoyl-N-allyl-carbamic acid chloride and 2.9 parts by weight of D,L-C-(2-thienyl)-glycine.
Yield: 96%.
NMR signals at $\tau$ = 2.5 (5 H), 2.5–3.1 (3 H), 3.8–4.5 (2 H), 4.8–5.3 (2 H) and 5.5–5.8 ppm (2 H).

18. D,L-α-(3-γ-Chlorobutyryl-3-methyl-ureido)-2-thienylacetic acid from 4.0 parts by weight of N-γ-chlorobutyryl-N-methylcarbamic acid chloride and 2.9 parts by weight of D,L-α-(2-thienyl)-glycine.
Yield: 99%.
NMR signals at $\tau$ = 2.5–3.1 (3H), 4.2 (1 H), 6.35 (2 H), 6.7 (3 H), 7.2 (2 H) and 7.9 ppm (2 H).

19. D,L-α-(3-[2-Furoyl]-3-methyl-ureido)-2-thienylacetic acid from 5.6 parts by weight of N-(2-furoyl)-N-methyl-carbamic acid chloride and 4.7 parts by weight of D,L-C-(2-thienyl)-glycine.
Yield: 100%.

20. D(−)-α-(3-Allyloxycarbonyl-3-methyl-ureido)-phenylacetic acid from 15.8 parts by weight of N-allyloxycarbonyl-N-methylcarbamic acid chloride and 15.1 parts by weight of D-C-phenylglycine.
Yield: 88%.
NMR signals at $\tau$ = 1.8 (1 H), +0.4 (1 H), 2.6 (5 H), 3.7–4.3 (1 H, 4.4–4.9 (3 H), 5.3 (2 H), and 6.85 ppm (3 H).

21. D(−)-α-(3-[3-Nitro-4-methylbenzoyl]-3-methyl-ureido)-phenylacetic acid from 8.0 parts by weight of N-(3-nitro-4-methylbenzoyl)-N-methyl-carbamic acid chloride and 4.7 parts by weight of D(−)-C-phenylglycine.
Yield: 46%.
NMR signals at $\tau$ = 1.6–2.8 (8 H), 4.6 (1 H), 6.8 (3 H) and 7.4 ppm (3 H).

22. D(−)-α-(3-[4-Methylbenzoyl]-3-methyl-ureido)-phenylacetic acid from 13 parts by weight of N-p-methylbenzoyl-N-methylcarbamic acid chloride and 9.2 parts by weight of D(−)-C-phenylglycine.
Yield: 85%.
NMR signals at $\tau$ = 0.2 (1 H), 2.4–2.9 (9 H), 6.65 (1 H), 6.9 (3 H) and 7.6 ppm (3 H).

23. D,L-α-(3-Benzoyl-3-methyl-ureido)-2,6-dichloro-phenylacetic acid from 7.2 parts by weight of N-benzoyl-N-methylcarbamic acid chloride and 8.0 parts by weight of D,L-C-(2,6-dichlorophenyl)-glycine.
Yield: 100%. Melting point = 200° C.
NMR signals at $\tau$ = −0.4 (1 H), 2.2–2.7 (8 H), 3.5 (1 H) and 6.9 (3 H).

24. D,L-α-(3-Benzoyl-3-methyl-ureido)-4-methylsulphenylphenylacetic acid from 10.0 parts by weight of N-benzoyl-N-methylcarbamic acid chloride and 10.0 parts by weight of D,L-C-(4-methylsulphenylphenyl)-glycine.
Yield: 73%
NMR signals at $\tau$ = 0.2 (1 H), 2.3–2.8 (9 H), 4.65 (1 H), 6.9 (3 H) and 7.5 ppm (3 H).

25. D,L-α-(3-Ethoxycarbonyl-3-methyl-ureido)-4-methylsulphenylphenylacetic acid from 16.8 parts by weight of N-ethoxycarbonyl-N-methyl-carbamic acid chloride and 20.0 parts by weight of D,L-C-(4-methylsulphenylphenyl)-glycine.
Yield: 85%. Melting point = 12°–122° C.
NMR signals at $\tau$ = 0.4 (1H), 2.4–2.9 (4 H), 4.65 (1 H), 5.76 (2 H), 6.85 (3 H) and 7.55 ppm (3 H).

26. D,L-α-(3-β-Chloropropionyl-3-methyl-ureido)-(1,2,5,6-tetrahydrophenylacetic acid from 18.4 parts by weight of N-β-chloropropionyl-N-methylcarbamic acid chloride and 15.5 parts by weight of D,L-C-(1,2,5,6-tetrahydrophenyl)-glycine.
Yield: 73%.
NMR signals at $\tau$ = 0.6 (1 H), 4.3 (2 H), 5.7 (1 H), 6.2 (2 H), 6.8 (2 H) and 7.7–8.8 ppm (7 H).

27. D(−)-α-(3-[2-Thenoyl]-3-methyl-ureido)-phenylacetic acid from 9.0 parts by weight of N-(2-thenoyl)-N-methyl-carbamic acid chloride and 6.6 parts by weight of D-C-phenylglycine.
Yield: 50%.

28. D(−)-α-(3,5-Dimethyl-isoxazol-4-oyl]-3-methyl-ureido)-phenylacetic acid from 8.5 parts by weight of N-(3,5-dimethylisoxazol-4-oyl)-N-methylcarbamic acid chloride and 5.9 parts by weight of D-C-phenylglycine.
Yield: 32%.

C. Sodium D(−)-α-(3-isopropoxycarbonyl-3-methyl-ureido)-benzylpenicillin:

This pencillin was manufactured as described in Example 9 from 5.9 parts by weight of D(−)-α-(3-isopropoxycarbonyl-3-methyl-ureido)-phenylacetic acid, 3.7 parts by weight of tetramethylchloroformamidinium chloride and 4.0 parts by weight of 6-aminopenicillanic acid.
Yield: 45%.
β-Lactam content: 86%

|  | C | H | N | S |
|---|---|---|---|---|
| Calculated: | 48.8 | 5.6 | 10.4 | 5.9 |
| Found: | 48.7 | 5.9 | 10.8 | 5.8 |

NMR signals at $\tau$ = 2.3–2.8 (5H), 4.4 (1 H), 4.55 (2 H), 5.0 (1 H), 5.8 (1 H), 6.85 (3 H, 8.5 (6 H), and 8.7 ppm (6 H).

The Table which follows compares the anti-bacterial action of this product (A) with the penicillin (B) prepared from ampicillin and N-i-propoxycarbonyl-N-methylcarbamic acid chloride and with the product (C) which was obtained from D(−)-α-(3-i-propoxycarbonyl-3-methylureido)-phenylacetic acid according to the procedure described in Example 28:

| Type of Bacterium | Effectiveness [units/ml] | | |
|---|---|---|---|
|  | (A) | (B) | (C) |
| Escherichia coli 14 | 6.25 | 6.25 | 100 |
| Escherichia coli C 165 | 50 | 25 | 200 |
| Escherichia coli 183/58 | 12.5 | 6.25 | 400 |
| Pseudomonas aer. Bonn. | 50 | 25 | >400 |
| Pseudomonas aer. Walter | 100 | 50 | >400 |

EXAMPLE 12

Sodium
D(−)-α-(3-n-butoxycarbonyl-3-methyl-ureido)-benzylpenicillin

This penicillin was prepared in the manner described in Example 9 from 5.6 parts by weight of D(−)-α-(3-n-butoxycarbonyl-3-methyl-ureido)-phenylacetic acid, 3.3 parts by weight of tetramethyl-chloroformamidinium chloride and 3.6 parts by weight of 6-aminopenicillanic acid. The ureidoacetic acid was stirred with the tetramethylchloroformamidinium chloride in acetone at −5° C for only 20 minutes.
Yield: 38%.
β-Lactam content: 61%.

|  | C | H | N | S |
|---|---|---|---|---|
| Calculated: | 48.1 | 6.0 | 9.7 | 5.6 |
| Found: | 48.4 | 5.5 | 9.4 | 5.5 |

NMR signals at $\tau$ = 2.3–2,8 (5 H), 4.45 (1 H), 4.55 (2 H, 5.8 (3 H), 6.85 (3 H and 8.1–8.9 ppm (13 H).

EXAMPLE 13

If, in the procedure of Example 10, the D(−)-α-(3-methoxycarbonyl-3-methyl-ureido)-phenylacetic acid used there is replaced by 0.018 mol of:
D(−)-α-(3-ethoxycarbonyl-3-methyl-ureido)-phenylacetic acid,
D(−)-α-(3-dimethylaminocarbonyl-3-methyl-ureido)-phenylacetic acid,
D(−)-α-(3-dimethylaminocarbonyl-3-ethyl-ureido)-phenylacetic acid,
D(−)-α-(3-dimethylaminocarbonyl-3-propyl-ureido)-phenylacetic acid,
D(−)-α-(3-dimethylaminocarbonyl-3-i-propyl-ureido)-phenylacetic acid,
D(−)-α-(3-dimethylaminocarbonyl-3-n-butyl-ureido)-phenylacetic acid,
D(−)-α-(3-dimethylaminocarbonyl-3-allyl-ureido)-phenylacetic acid,
D(−)-α-(3-dimethylaminocarbonyl-3-cyclohexyl-ureido)-phenylacetic acid,
D(−)-α-(3-dimethylaminocarbonyl-3-phenyl-ureido)-phenylacetic acid,
D(−)-α-(3-[1-pyrrolidylcarbonyl]3-methyl-ureido)-phenylacetic acid,
D(−)-α-(3-[1-piperidylcarbonyl]-3-methyl-ureido)-phenylacetic acid,
D(−)-α-(3-diethylaminocarbonyl-3-methyl-ureido)-phenylacetic acid,
D(−)-α-(3-ethylaminocarbonyl-3-methyl-ureido)-phenylacetic acid,
D(−)-α-(3-methylaminocarbonyl-3-methyl-ureido)-phenylacetic acid,
D(−)-α-(3-phenylaminocarbonyl-3-methyl-ureido)-phenylacetic acid,
D(−)-α-(3-[4-morpholinyl]-carbonyl-3-methyl-ureido)-phenylacetic acid,
D(−)-α-(3-[1-pyrrolidylcarbonyl]-3-ethyl-ureido)-phenylacetic acid,
D(−)-α-(3-[1-piperidylcarbonyl]-3-ethyl-ureido)-phenylacetic acid,
D(−)-α-(3-diethylaminocarbonyl-3-ethyl-ureido)-phenylacetic acid,
D(−)-α-(3-ethylaminocarbonyl-3-ethyl-ureido)-phenylacetic acid,
D(−)-α-(3-methylaminocarbonyl-3-ethyl-ureido)-phenylacetic acid,
D(−)-α-(3-phenylaminocarbonyl-3-ethyl-ureido)-phenylacetic acid,
D(−)-α-(3-[4-morpholinyl]-carbonyl-3-ethyl-ureido)phenylacetic acid,
D(−)-α-)3-[1-pyrrolidyl]-carbonyl-3-n-propyl-ureido)-phenylacetic acid,
D(−)-α-(3-[1-piperidyl]-carbonyl-3-i-propyl-ureido)-phenylacetic acid,
D(−)-α-(3-diethylaminocarbonyl)-3-n-butyl-ureido)-phenylacetic acid or
D(−)-α-(3-dimethylaminocarbonyl)-3-cyclohexyl-ureido-phenylacetic acid, the sodium salts of the following penicillins are obtained:
D(−)-α-(3-ethoxycarbonyl-3-methyl-ureido)-benzylpenicillin,
D(−)-α-(3-dimethylaminocarbonyl-3-methyl-ureido)-benzylpenicillin,
D(−)-α-(3-dimethylaminocarbonyl-3-ethyl-ureido)-benzylpenicillin,
D(−)-α-(3-dimethylaminocarbonyl-3-propyl-ureido)-benzylpenicillin,
D(−)-α-(3-dimethylaminocarbonyl-3-i-propyl-ureido)-benzylpenicillin,
D(−)-α-(3-dimethylaminocarbonyl-3-n-butyl-ureido)-benzylpenicillin,
D(−)-α-(3-dimethylaminocarbonyl-3-allyl-ureido)-benzylpenicillin,
D(−)-α-(3-dimethylaminocarbonyl-3-cyclohexyl-ureido)-benzylpenicillin,
D(−)-α-(3-dimethylaminocarbonyl-3-phenyl-ureido)-benzylpenicillin, D(−)-α-(3-[1-pyrrolidylcarbonyl]-3-methyl-ureido)-benzylpenicillin,
D(−)-α-(3-[1-piperidylcarbonyl]-3-methyl-ureido)-benzylpenicillin,
D(−)-α-(3-diethylaminocarbonyl-3-methyl-ureido)-benzylpenicillin,
D(−)-α-(3-ethylaminocarbonyl-3-methyl-ureido)-benzylpenicillin,
D(−)-α-(3-methylaminocarbonyl-3-methyl-ureido-benzylpenicillin,
D(−)-α-(3-phenylaminocarbonyl-3-methyl-ureido)-benzylpenicillin,
D(−)-α-(3-[4-morpholinyl]-carbonyl-3-methyl-ureido)-benzylpenicillin,
D(−)-α-(3-[1-pyrrolidylcarbonyl]-3-ethyl-ureido)-benzylpenicillin,
D(−)-α-(3-[1-piperidylcarbonyl]-3-ethyl-ureido)-benzylpenicillin,
D(−)-α-(3-diethylaminocarbonyl-3-ethyl-ureido)-benzylpenicillin,
D(−)-α-(3-ethylaminocarbonyl-3-ethyl-ureido)-benzylpenicillin,
D(−)-α-(3-methylaminocarbonyl-3-ethyl-ureido)-benzylpenicillin,
D(−)-α-(3-phenylaminocarbonyl-3-ethyl-ureido)-benzylpenicillin,
D(−)-α-(3-[4-morpholinyl]-carbonyl-3-ethyl-ureido)-benzylpenicillin,
D(−)-α-(3-[1-pyrrolidyl]-carbonyl-3-n-ethyl-ureido)-benzylpenicillin,
D(−)-α-(3-[1-piperidyl]-carbonyl-3-i-propyl-ureido)-benzylpenicillin,
D(−)-α-(3-diethylaminocarbonyl)-3-n-butyl-ureido)-benzylpenicillin, or
D(−-α-(3-diethylaminocarbonyl-3-cyclohexyl-ureido)-benzylpenicillin.

EXAMPLE 14

Sodium D,L-α-(3-benzoyl-3-allyl-ureido)-4-methoxybenzyl-penicillin

This penicillin was prepared in the manner described in Example 9, from 4.4 parts by weight of D,L-α-(3-benzoyl-3-allyl-ureido)-4-methoxyphenylacetic acid, 2.26 parts by weight of tetramethylchloroformamidinium chloride and 2.6 parts by weight of 6-aminopenicillanic acid.
Yield: 51%
β-Lactam content: 65%.

|  | C | H | N | S |
|---|---|---|---|---|
| Calculated: | 55.4 | 5.2 | 9.2 | 5.3 |
| Found: | 55.4 | 4.8 | 8.1 | 4.5 |

NMR signals at τ = 2.6 (5 H), 2.7 (2 H), 3.2 (2 H), 3.9–4.5 (1 H), 4.55 (3 H), 4.7–5.2 (2 H), 5.6–5.9 (3 H), 6.25 (3 H) and 8.4 ppm (6 H).

EXAMPLE 15

Sodium D,L-α-(3benzoyl-3-allyl-ureido)-2,6-dichlorobenzyl-penicillin

This penicillin was prepared in the manner described in Example 9 from 7.2 parts by weight of D,L-α-(3-benzoyl-3-allyl-ureido)-2,6-dichlorophenylacetic acid, 4.05 parts by weight of tetramethylchloroformamidinium chloride and 3.86 parts by weight of 6-aminopenicillanic acid.
Yield: 46%.
β-Lactam content: 83%.

|  | C | H | Cl | N | S |
|---|---|---|---|---|---|
| Calculated: | 49.5 | 4.3 | 10.8 | 1.6 | 4.9 |
| Found: | 49.9 | 5.1 | 11.3 | 8.2 | 4.4 |

NMR signals at τ= 2.4–2.9 (8 H), 3.4 (1H), 3.8–4.4 (1 H), 4.4–4.6 (2 H), 4.8–5.2 (2 H), 5.5–5.8 (2 H), 5.85 (1 H) and 8.5 ppm (6 H).

EXAMPLE 16

If, in the procedure of Example 4, the D,L-α-(3-benzoyl-3-methyl-ureido)-p-tolyl-acetic acid used there is replaced by 0.015 mol of:
D(−)-α-(3-benzoyl-3-methyl-ureido)-phenylacetic acid,
D(−)-α-(3-benzoyl-3-ethyl-ureido)-phenylacetic acid,
D(−)-α-(3-benzoyl-3-methyl-ureido)-4-chlorophenylacetic acid,
D(−)-α-(3-benzoyl 3-methyl-ureido)-4-methoxyphenylacetic acid,
D(−)-α-(3-benzoyl-3-methyl-ureido)-2-chlorophenylacetic acid,
D(−)-α-(3-benzoyl-3-methyl-ureido)-3-iodophenylacetic acid,
D(−)-α-(3-benzoyl-3-methyl-ureido)-2,6-dimethoxyphenylacetic acid,
D(−)-α-(3-benzoyl-3-methyl-ureido)-2,4-dibromophenylacetic acid,
D(−0-α-(3-benzoyl-3-methyl-ureido)-3-thienylacetic acid,
D(−)-α-(3-benzoyl-3-methyl-ureido)-m-tolylacetic acid,
D(−)-α-(3-benzoyl-3-methyl-ureido)-2,6-dimethylphenylacetic acid,
D(−)-α-(3-benzoyl-3-methyl-ureido)-2-chloro-6-fluorophenylacetic acid,
D(−)-α(3-benzoyl-3-methyl-ureido)-2-thienylacetic acid,
L(+)-α-(3-benzoyl-3-methyl-ureido)-phenylacetic acid,
D(−)-α-(3-[3-nitro-4-methoxyphenyl]-3-methyl-ureido)-phenylacetic acid,
D(−)-α-(3-p-chlorobenzoyl-3-ethyl-ureido)-phenylacetic acid,
D(−)-α-(3-o-bromobenzoyl-3-n-propyl-ureido)-phenylacetic acid,
D(−)-α-(3-methoxybenzoyl-3-methyl-ureido)-phenylacetic acid,
D(−)-α-(3-p-methoxycarbonylaminobenzoyl-3-methyl-ureido)-phenyl acetic acid,
D(−)-α-(3-p-methylsulphenylbenzoyl-3-methyl-ureido)-phenylacetic acid,
D(−)-α-(3-[2-chloro-5-methoxybenzoyl]-3-n-butyl-ureido)-phenylacetic acid,
D(−)-α-(3-p-nitrobenzoyl-3-methyl-ureido)-phenylacetic acid,
D(−)-α-(3-[2-chloro-4-ethylsulphenylbenzoyl]-3-methyl-ureido)-phenylacetic acid,
D(−)-α-(3-m-cyanobenzoyl-3-methyl-ureido)-phenylacetic acid, D(—)-α-(3-[3,5-dimethylbenzoyl]-3-methyl-ureido)-phenylacetic acid,
D(—)-α-(3-benzoyl-3-allyl-ureido)-phenylacetic acid,
D(—)-α-(3-m-iodobenzoyl-3-methyl-ureido)-phenylacetic acid,
D(—)-α-(3-benzoyl-3-phenyl-ureido)-phenylacetic acid or
D(—)-α-(3-naphthoyl(1)-3-methyl-ureido)-phenylacetic acid, the sodium salts of the following penicillins are obtained:
D(—)-α-(3-benzoyl-3-methyl-ureido)-benzylpenicillin,
D(—)-α-(3-benzoyl-3-ethyl-ureido)-benzylpenicillin,
D(—)-α-(3-benzoyl-3-methyl-ureido)-4-chlorobenzylpenicillin,
D(—)-α-(3-benzoyl-3-methyl-ureido)-4-methoxybenzylpenicillin,
D(—)-α-(3-benzoyl-3-methyl-ureido)-2-chloro-benzylpenicillin,
D(—)-α-(3-benzoyl-3-methyl-ureido)-3-iodo-benzylpenicillin,
D(—)-α-(3-benzoyl-3-methyl-ureido)-2,6-dimethoxy-benzylpenicillin,
D(—)-α-(3-benzoyl-3-methyl-ureido)-2,4-dibromobenzylpenicillin,
D(—)-α-(3-benzoyl-3-methyl-ureido)-3-thienylmethylpenicillin,
D(—)-α-(3-benzoyl-3-methyl-ureido)-3-methylbenzylpenicillin,
D(—)-α-(3-benzoyl-3-methyl-ureido)-2,6-dimethylbenzylpenicillin,
D(—)-α-(3-benzoyl-3-methyl-ureido)-2-chloro-6-fluorobenzylpenicillin,
D(—)-α-(3-benzoyl-3-methyl-ureido)-2-thienylmethylpenicillin,
L(+)-α-(3-benzoyl-3-methyl-ureido)-benzylpenicillin,
D(—)-α-(3-[3-nitro-4-methoxyphenyl]-3-methyl-ureido)-benzylpenicillin,
D(—)-α-(3-p-methoxybenzoyl-3-methyl-ureido)-benzylpenicillin,
D(—)-α-(3-p-methoxycarbonylaminobenzoyl-3-methyl-ureido)-benzyl penicillin,
D(—)-α-(3-p-chlorobenzoyl-3-ethyl-ureido)-benzylpenicillin,
D(—)-α-(3-o-bromobenzoyl-3-n-propyl-ureido)-benzylpenicillin,
D(—)-α-(3-[2-chloro-5-methoxybenzoyl]-3-n-butyl-ureido)-benzylpenicillin,
D(—)-α-(3-p-methylsulphenylbenzoyl-3-methyl-ureido)-benzylpenicillin,
D(—)-α-(3-p-nitrobenzoyl-3-methyl-ureido)-benzylpenicillin,
D(—)-α-(3-[2-chloro-4-ethylsulphenyl-benzoyl]-3-methyl-ureido)-benzylpenicillin,
D(—)-α-(3-m-cyano-benzoyl-3-methyl-ureido)-benzylpenicillin,
D(—)-α-(3-[3,5-dimethyl-benzoyl]-3-methyl-ureido)-benzylpenicillin,
D(—)-α-(3-benzoyl-3-allyl-ureido)-benzylpenicillin,
D(—)-α-(3-m-iodobenzoyl-3-methyl-ureido)-benzylpenicillin,
D(—)-α-(3-benzoyl-3-phenyl-ureido)-benzylpenicillin or
D(—)-α-(3-naphthyl(1)-3-methyl-ureido)-benzylpenicillin.

EXAMPLE 17

Sodium D,L-α-(3-acetyl-3-allyl-ureido)-2-thienylmethylpenicillin

This penicillin was prepared in the manner described in Example 9 from 5.0 parts by weight of D,L-α-(3-acetyl-3-allyl-ureido)-2-thienyl-acetic acid, 3.6 parts by weight of tetramethylchloroformamidinium chloride and 3.9 parts by weight of 6-aminopenicillanic acid. Yield: 53%.
β-Lactam content: 72%.
NMR signals at τ = 2.5–3.2 (3 H), 3.8–4.4 (1 H), 4.2 (1 H), 4.5 (2 H), 4.6–5.0 (2 H), 5.5–5.7 (2 H), 5.8 (1 H), 7.7 (3 H), and 8.4 ppm (6 H).

|  | C | H | N | S |
|---|---|---|---|---|
| Calculated: | 46.2 | 4.9 | 10.8 | 12.3 |
| Found: | 46.6 | 5.3 | 10.4 | 12.3 |

EXAMPLE 18

Sodium D,L-α-(3-methoxycarbonyl-3-methyl-ureido)-4-methoxybenzylpenicillin 3.04 parts by weight of tetramethylchloroformamidinium chloride in 20 parts by volume of dry dichloromethane were initially taken at 0° C, and a solution of 4.8 parts by weight of D,L-α-(3-methoxycarbonyl-3-methylureido)-4-methoxyphenylacetic acid in 10 parts by volume of methylene chloride was added. 2.24 parts by volume of triethylamine in 10 parts by volume of methylene chloride were now added dropwise over the course of 30 minutes at 0° C, with exclusion of moisture. Thereafter the mixture was stirred for 20 minutes at +5° C, insoluble matter was filtered off without the solution rising to above 5° C, and the filtrate was cooled to —20° C. A solution of 5.0 parts by weight of 6-aminopenicillanic acid and 3.5 parts by volume of triethylamine in 20 parts by volume of methylene chloride, prepared as described in Example 1, and also cooled to —20° C, was added thereto. The mixture was stirred for 30 minutes at 0° C and subsequently for a further 30 minutes at room temperature, and was finally poured into 150 parts by volume of ice water and adjusted to a pH value of 6.5 with 2 N sodium hydroxide solution. After separating off the organic layer and adding 150 parts by volume of a 1:1 mixture of ethyl acetate and ether, the mixture was worked up as described in Example 1 and the sodium salt of the penicillin was isolated.
Yield: 54%.
β-Lactam content: 75%.
NMR signals at τ = 2.6 (2H), 3.1 (2 H), 4.3–4.9 (3 H), 5.8 (1 H), 6.2 (6 H), 6.85 (3 H) and 8.5 ppm (6 H).
Effectiveness in Animal Experiments: B.

EXAMPLE 19

Sodium D,L-α-(3-dimethylaminocarbonyl-3-methyl-ureido)-4-methoxybenzylpenicillin This penicillin was prepared as described in Example 18, from 6.0 parts by weight of D,L-α-(3-dimethylaminocarbonyl-3methyl-ureido)-4-methoxyphenylacetic acid, 3.8 parts by weight of tetramethylchloroformamidinium chloride and 6.2 parts by weight of 6-aminopenicillanic acid.
Yield: 23%.
β-Lactam content: 59%.
NMR signals at τ = 2.65 (2 H), 3.1 (2 H), 4.4–4.8 (3 H), 5.65 (1 H), 6.2 (3 H), 6.9 (3 H), 7.05 (6 H) and 8.4 ppm (6 H).

EXAMPLE 20

Sodium D,L-α-(3-methoxycarbonyl-3-methyl-ureido)-2-thienylmethylpenicillin

This penicillin was prepared as described in Example 18, from 4.5 parts by weight of D,L-α-(3-methoxycarbonyl-3-methylureido)-thienylacetic acid, 3.2 parts by weight of tetramethylchloroformamidinium chloride and 5.2 parts by weight of 6-aminopenicillanic acid.
Yield: 62%.
β-Lactam content: 84%.
NMR signals at τ = 2.5 –3.2 (3H), 4.2 (1 H), 4.5 (2 H), 5.8 (1 H), 6.2 (3 H), 6.8 (3 H) and 8.4 ppm (6 H).
Effectiveness in animal experiments: A

EXAMPLE 21

Sodium D,L-α-(3-benzoyl-3-allyl-ureido)-2-thienylmethyl-penicillin:

This penicillin was prepared as described in Example 18, from 6.0 parts by weight of D,L-α-(3-benzoyl-3-allyl-ureido)-2-thienylacetic acid, 3,4 parts by weight of tetramethylchloroformamidinium chloride and 5.5 parts by weight of 6-aminopenicillanic-acid.
Yield: 45%.
β-Lactam content: 77%.
NMR signals at τ = 2.5 (5 H) 2.5–3.1 (3 H), 3.7–4.4 (2 H), 4.5 (2 H), 4.7–5.2 (2 H), 5.5–5.9 (3 H) and 8.4 ppm (6 H). Effectiveness in Animal Experiments: B.

EXAMPLE 22

Sodium D,L-α-(3-[2-furoyl]-3-methyl-ureido)-2-thienylmethylpenicillin:

This penicillin was prepared as described in Example 18, from 11.6 parts by weight of D,L-α-(3-[2-furoyl]-3-methyl-ureido)-2-thienylacetic acid, 6.5 parts by weight of tetramethylchloroform-amidinium chloride and 3.2 parts by weight of 6-aminopenicillanic acid.
Yield: 39%.
β-Lactam content: 88%.
NMR signals at τ = 2.2 (1 H), 2.5–3.1 (4 H), 3.35 (1 H), 4.1 (1 H), 4.45 (2 H), 5.8 (1 H), 6.55 (3 H) and 8.4 ppm (6 H).
Effectiveness in animal experiments: A and B

EXAMPLE 23

Sodium D,L-α-(3-dimethylaminocarbonyl-3-methyl-ureido)-2-thienylmethylpenicillin:

A suspension of 3.9 parts by weight of tetramethyl-chloroformamidinium chloride in 30 parts by volume of dry acetone was treated with a solution of D,L-α-(3-dimethylaminocarbonyl-3-methyl-ureido)2-thienylacetic acid in 10 parts by volume of acetone over the course of 5 minutes at −20+ C, and subsequently 2.1 parts by volume of triethylamine in 5 parts by volume of acetone were added dropwise over the course of 30 minutes. After the mixture had been stirred for a further hour at −20° C, it was filtered in such a way that the temperature of the solution did not rise above −10° C. It was again cooled to −20° C and combined with a vigorously stirred solution of 3.9 parts by weight of 6-aminopenicillanic acid in 50 ml of 60% strength aqueous tetrahydrofurane (solution took place after adding sufficient 2 N NaOH to establish a pH valve of 8.2), cooled to −5° C. A pH range of 7.5 - 8.0 was maintained by adding 2 N sodium hydroxide solution. After 15 minutes, the mixture was allowed to come to room temperature and stirring was continued until no further change in the pH value was observable. The subsequent working-up of the reaction mixture and the isolation of the penicillin was carried out in the manner indicated in Example 9.
Yield: 43%.
β-Lactam content: 54%.
NMR signals at τ = 2.5–3.2 (3 H), 4.5 (3 H), 5.8 (1 H), 6.9 (3 H), 7.05 (6 H), and 8.4 ppm (6 H).

EXAMPLE 24

Sodium D(−)-α-(3-γ-chlorobutyryl-3-methyl-ureido)-benzylpenicillin 5.1 parts by weight of D(−)-α-(3-γ-chlorobutyryl-3-methyl-ureido)-phenylacetic acid and 3.0 parts by weight of tetramethylchloro-formamidinium chloride were reacted in methylene chloride as described in Example 18. The resulting solution was combined with a solution of 6.5 parts by weight of N-trimethylsilyl-6-aminopenicillanic acid trimethylsilyl ester in 33 parts by volume of dry methylene chloride at 0° C. 1.3 parts by weight of pyridine were added and the mixture was stirred, while excluding moisture, for one hour at 0° C and subsequently for 2.5 hours at room temperature. It was now poured into 120 parts by volume of ice water, a pH valve of 7 - 8 was established and the methylene chloride was stripped off in vacuo. The aqueous phase was shaken with 50 parts by volume of ether, which was then discarded, whilst the aqueous phase was freed of solid constituents by filtration. It was now covered with 200 parts by volume of a 1 : 1 mixture of ether and ethyl acetate, cooled to 0° C and acidified to pH = 2 with 2 N hydrochloric acid, while stirring vigorously. The organic solution was separated off, twice washed with 50 parts by volume of water at a time, dried over MgSO₄ and filtered, and the sodium salt of the penicillin was precipitated by adding 15 ml of a 1 M solution of sodium 2-ethylhexanoate in ether containing methanol. The entire mixture was concentrated almost to dryness at 0° C, rapidly dissolved in as little methanol as possible, and precipitated by adding excess ether. Non-crystalline solid substance.
Yield: 29%.
β-Lactam content: 49%. Position of the NMR signals as indicated in Example 2.

The crude product still contained O-α-(3-γ-chlorobutyryl-3-methyl-ureido)-phenylacetic acid which was removable by fractional extraction of the aqueous penicillin salt solution at pH values of 5.5 – 6.5.

EXAMPLE 25

If, in the procedure of Example 1, the D(−)-α-(3-acetyl-3-allyl-ureido)-phenylacetic acid used there is replaced by 0.02 mol of:
 D(−)-α-(3-acetyl-3-methyl-ureido)-phenylacetic acid,
 D(−)-α-(3-acetyl-3-ethyl-ureido)-phenylacetic acid, D(−)-α-(3-acetyl-3-vinyl-ureido)-phenylacetic acid,
D(−)-α-(3-acetyl-3-n-propyl-ureido)-phenylacetic acid,
D(−)-α-(3-acetyl-3-propenyl-ureido)-phenylacetic acid,
D(−)-α-(3-acetyl-3-i-propyl-ureido)-phenylacetic acid,
D(−)-α-(3-acetyl-3-n-butyl-ureido)-phenylacetic acid,
D(−)-α-(3-acetyl-3-β-methoxyethyl-ureido)-phenylacetic acid,
D(−)-α-(3-acetyl-3-β-dimethylaminoethyl-ureido)-phenylacetic acid,
D(−)-α-(3-acetyl-3-cyclohexyl-ureido)-phenylacetic acid,
D(−)-α-(3-acetyl-3-cyclobutyl-ureido)-phenylacetic acid,
D(−)-α-(3-acetyl-3-benzyl-ureido)-phenylacetic acid,
D(−)-α-(3-formyl-3-methyl-ureido)-phenylacetic acid,
D(−)-α-(3-formyl-3-ethyl-ureido)-phenylacetic acid,
D(−)-α-(3-formyl-3-propyl-ureido)-phenylacetic acid,
D(−)-α-(3-formyl-3-i-propyl-ureido)-phenylacetic acid,
D(−)-α-(3-acetyl-3-t-butyl-ureido)-phenylacetic acid,
D(−)-α-(3-formyl-3-n-butyl-ureido)-phenylacetic acid,
D(−)-α-(3-formyl-3-allyl-ureido)-phenylacetic acid,
D(−)-α-(3-formyl-3-benzyl-ureido)-phenylacetic acid,
D(−)-α-(3-formyl-3-phenyl-ureido)-phenylacetic acid,
D(−)-α-(3-formyl-3-cyclopropyl-ureido)-phenylacetic acid,
D(−)-α-(3-formyl-3-cyclobutyl-ureido)-phenylacetic acid,
D(−)-α-(3-formyl-3-cyclopentyl-ureido)-phenylacetic acid or
D(−)-α-(3-formyl-3-cyclohexyl-ureido)-phenylacetic acid, the following penicillins are obtained in the form of their sodium salts:
D(−)-α-(3-acetyl-3-methyl-ureido)-benzylpenicillin,
D(−)-α-(3-acetyl-3-ethyl-ureido)-benzylpenicillin,
D(−)-α-(3-acetyl-3-vinyl-ureido)-benzylpenicillin,
D(−)-α-(3-acetyl-3-n-propyl-ureido)-benzylpenicillin,
D(−)-α-(3-acetyl-3-prop-1-enyl-ureido)-benzylpenicillin,
D(−)-α-(3-acetyl-3-i-propyl-ureido)-benzylpenicillin,
D(−)-α-(3-acetyl-3-n-butyl-ureido)-benzylpenicillin,
D(−)-α-(3-acetyl-3-t-butyl-ureido)-benzylpenicillin,
D(−)-α-(3-acetyl-3-β-methoxyethyl-ureido)-benzylpenicillin.
D(−)-α-(3-acetyl-3-β-dimethylaminoethyl-ureido)-benzylpenicillin,
D(−)-α-(3-acetyl-3-cyclohexyl-ureido)-benzylpenicillin,
D(−)-α-(3-acetyl-3-cyclobutyl-ureido)-benzylpenicillin,
D(−)-α-(3-acetyl-3-benzyl-ureido)-benzylpenicillin,
D(−)-α-(3-formyl-3-methyl-ureido)-benzylpenicillin,
D(−)-α-(3-formyl-3-ethyl-ureido)-benzylpenicillin,
D(−)-α-(3-formyl-3-propyl-ureido)-benzylpenicillin,
D(−)-α-(3-formyl-3-i-propyl-ureido)-benzylpenicillin,
D(−)-α-(3-formyl-3-n-butyl-ureido)-benzylpenicillin,
D(−)-α-(3-formyl-allyl-ureido)-benzylpenicillin,
D(−)-α-(3-formyl-3-benzyl-ureido)-benzylpenicillin,
D(−)-α-(3-formyl-3-phenyl-ureido)-benzylpenicillin,
D(−)-α-(3-formyl-3-cyclopropyl-ureido)-benzylpenicillin,
D(−)-α-(3-formyl-3-cyclobutyl-ureido)-benzylpenicillin,
D(−)-α-(3-formyl-3-cyclopentyl-ureido)-benzylpenicillin,
or D(−)-α-(3-formyl-3-cyclohexyl-ureido)-benzylpenicillin.

EXAMPLE 26

If, in the procedure of Example 1, the D(−)-α-(3-acetyl-3-allyl-ureido)-phenylacetic acid used there is replaced by 0.02 mol of:
D(−)-α-(3-methoxyacetyl-3-methyl-ureido)-phenylacetic acid,
D(−)-α-(3-propionyl-3-methyl-ureido)-phenylacetic acid,
D(−)-α-(3-methylsulphenylacetyl-3-methyl-ureido)-phenylacetic acid,
D(−)-α-(3-propionyl-3-ethyl-ureido)-phenylacetic acid,
D(−)-α-(3-propionyl-3-vinyl-ureido)-phenylacetic acid,
D(−)-α-(3-n-butyryl-3-methyl-ureido)-phenylacetic acid,
D(−)-α-(3-methoxycarbonyl-acetyl-3-methyl-ureido)-phenylacetic acid,
D(−)-α-(3-i-butyryl-3-methyl-ureido)-phenylacetic acid,
D(−(-α-(3-acryloyl-3-methyl-ureido)-phenylacetic acid,
D(−)-α-(3-pivaloyl-3-methyl-ureido)-phenylacetic acid,
D(−)-α-(3-cyanomethyl-acetyl-3-methyl-ureido)-phenylacetic acid,
D(−)-α-(3-acetyl-3-phenyl-ureido)-phenylacetic acid,
D(−)-α-(3-propionyl-3-phenyl-ureido)-phenylacetic acid,
D(−)-α-(hexahydroazepin-2-on-1-yl-carbonylamino)-phenylacetic acid
or D(−)-α-(pyrrolid-2-on-1-yl-carbonylamino)-phenylacetic acid, the following penicillins are obtained:
D(−)-α-(3-methoxyacetyl-3-methyl-ureido)-benzylpenicillin,
D(−)-α-(3-propionyl-3-methyl-ureido)-benzylpenicillin,
D(−)-α-(3-methylsulphenylacetyl-3-methyl-ureido)-benzylpenicillin,
D(−)-α-(3-propionyl-3-ethyl-ureido)-benzylpenicillin,
D(−)-α-(3-propionyl-3-vinyl-ureido)-benzylpenicillin,
D(−)-α-(3-n-butyryl-3-methyl-ureido)-benzylpenicillin,
D(−)-α-(3-methoxycarbonylacetyl-3-methyl-ureido)-benzylpenicillin,
D(−)-α-(3-i-butyryl-3-methyl-ureido)-benzylpenicillin, D(—)-α-(3-acryloyl-3-methyl-ureido)-benzylpenicillin, D(—)-α-(3-pivaloyl-3-methyl-ureido)-benzylpenicillin, D(—)-α-(3-cyanomethyl-acetyl-3-methyl-ureido)-benzylpenicillin, D(—)-α-(3-acetyl-3-phenyl-ureido)-benzylpenicillin, D(—)-α-(3-propionyl-3-phenyl-ureido)-benzylpenicillin, D(—)-α-(hexahydroazepin-2-on-1-yl-carbonylamino)-benzylpenicillin or D(—)-α-(pyrrolid-2-on-1-yl-carbonylamino)-benzylpenicillin.

EXAMPLE 27

Attempt to prepare sodium D(—)-α-(3-methoxycarbonyl-3-methyl-ureido)-benzylpenicillin:

5.2 parts by weight of D(—)-α-(3-methoxycarbonyl-3-methyl-ureido)-phenylacetic acid were suspended in a mixture of 10 parts by weight of benzene, 5 parts by weight of thionyl chloride and 0.05 part by weight of dimethylformamide and the mixture was subsequently carefully warmed, whilst stirring with a magnetic stirrer. The mixture was kept at about 60° C until the evolution of gas had ceased, and subsequently thionyl chloride and benzene were removed in a waterpump vacuum, finally at 0.1 mm Hg and 50° C. The product which remained showed strong bands in the IR spectrum at 1805, 1725 and 1175cm⁻¹.

Yield: 5.5 parts by weight. Calculated as D(—)-α-(3-methoxycarbonyl-3-methyl-ureido)-phenylacetic acid chloride:

| Calculated: | C 50.55 | H 4.56 | Cl 12.47 | N 9.84 |
|---|---|---|---|---|
| Found: | C 47.57 | H 4.29 | Cl 11.6 | N 9.68 |

5 parts by weight of the product thus obtained, dissolved in 10 parts by volume of dry tetrahydrofurane, were added dropwise, while stirring, to an ice-cooled solution of 3.8 parts by weight of 6-aminopenicillanic acid in 50 parts by volume of 80% strength aqueous tetrahydrofurane (addition of sufficient 2 N sodium hydroxide solution for solution to occur at pH 8.2). In the course thereof, the pH value was kept at between 7 and 8 by simultaneous addition of further 2 N sodium hydroxide solution. Thereafter, the mixture was further stirred for 30 minutes at 0° C and then stirred at room temperature until no further addition of sodium hydroxide solution was necessary for maintaining a pH value of 7 = 8.

100 parts by volume of water was now added, the tetrahydrofurane was removed at 0° C in vacuo, and the aqueous solution which remained was extracted with 50 parts by volume of ether to remove neutral constituents. It was then covered with 150 parts by volume of a 1 : 1 mixture of ether and ethyl acetate and thereafter acidified with dilute hydrochloric acid to pH = 2.0, while cooling with ice and stirring.

The organic phase was separated off, washed with 50 parts by volume of water and dried over MgSO₄.

Thereafter, 17 parts by volume of a 1 M solution of sodium 2-ethylhexanoate in ether containing methanol were added, the mixture was evaporated almost to dryness in vacuo, and the residue was dissolved in the minimum amount of methanol. On adding excess ether, a colorless, non-crystalline product precipitated, which, after decanting the supernatant solution, was digested with ether, filtered off and dried over P₂O₅ in a vacuum dessicator.

Yield: 6 parts by weight.

β-Lactam content: 88%. Calculated as methoxycarbonyl-methyl-ureido-benzylpenicillin:

|  | C 49.3 | H 4.7 | Cl — | N 11.5 | S 6.6 |
|---|---|---|---|---|---|
| Found: | C 47.5 | H 6.0 | Cl 0.1 | N 9.9 | S 7.0 |

The thin layer chromatogram of the product (silica gel, 10 : 3 : 1 mixture of n-butanol, n-pentane and glacial acetic acid, running time 1.5 hours) showed spots at Rf values of 0.045, 0.11 – 0.3 and 0.56. Authentic D(—)-α-(3-methoxycarbonyl-3-methyl-ureido)-benzylpenicillin, manufactured either according to the method of Example 8 or by acylation of ampicillin with N-methoxycarbonyl-N-methyl-carbamic acid chloride, showed an Rf value of 0.45 under the same conditions. An electrophorogram developed with Bacillus subtilis showed the presence of several antibiotically active substances, of which, however, none agreed with the authentic material. Finally, the NMR spectrum permitted the presence of major amounts of the desired methoxycarbonyl-methylureido-benzylpenicillin to be ruled out; rather it confirmed the assumption of a mixture of several different substances.

As regards the anti-bacterial effectiveness of this product, see the Table accompanying Example 8.

EXAMPLE 28

In the reaction of D(—) -α-(3-i-propoxycarbonyl-3-methyl-ureido)-phenylacetic acid and of D(—)-α-(3-n-butoxycarbonyl-3-methyl-ureido)-phenylacetic acid with thionyl chloride and subsequently with 6-aminopenicillanic acid in the manner described in Example 11 C, products were in each case again obtained which proved to be mixtures of several antibiotically active substances, but of which none was identical with the authentic D(—)-α-(3-i-propoxycarbonyl-3-methyl-ureido)-benzylpenicillin or D(—)-α-(3-n-butoxycarbonyl-3-methyl-ureido)-benzylpenicillin manufactured according to the instruction of Examples 9C and 10. The Rf values of thin layer chromatograms developed on silica gel with a 9 : 3 : 1 mixture of n-butanol, pentane and glacial acetic acid were 0.080 and 0.35, and 0.078, 0.46 and 0.75, respectively.

Under the same conditions, the authentic products showed Rf values of 0.56 and 0.64 respectively.

Products from the reaction of D(—)-α-(3-i-propoxycarbonyl-3-methyl-ureido)-phenylacetic acid:

For anti-bacterial effectiveness, see the Table accompanying Example 9C.

Products from the reaction of D(—)-α-(3-n-butoxycarbonyl-3-methyl-ureido)-phenylacetic acid:

The Table which follows compares the anti-bacterial action of this product (A) with the penicillins (B) prepared from ampicillin and N-n-butoxycarbonyl-N-methyl-carbamic acid chloride:

| Type of Bacterium | Effectiveness [units/ml] | |
|---|---|---|
|  | (A) | (B) |
| Escherichia coli 14 | 100 | 3.12 |
| Escherichia coli C 165 | 200 | 6.25 |
| Escherichia coli 183/58 | 400 | 6.25 |

-continued

| Type of Bacterium | Effectiveness [units/ml] (A) | (B) |
| --- | --- | --- |
| *Proteus* 3400 | >400 | 25 |
| *Proteus* 1017 | >400 | 12.5 |
| *Pseudomonas aerug.* Bonn. | >400 | 12.5 |
| *Pseudomonas aerug.* Walter | >400 | 25 |
| *Staphylococcus aur.* 133 | 12.5 | <0.78 |

EXAMPLE 29

Sodium D(−)-α-(3-cyclohexyloxycarbonyl-3-methyl-ureido)-benzylpenicillin:

4.5 parts by weight of 6-aminopenicillanic acid were suspended in 60 parts by volume of 50% strength aqueous tetrahydrofurane, the amount of triethylamine just sufficient to dissolve the aminopenicillanic acid was added, the resulting solution, which had a pH of 8.0 (glass electrode) was cooled to 0° C, and a solution of 8.0 parts by weight of O-[D(−)-α-(3-cyclohexyloxycarbonyl-3-methylureido)-phenylacetyl]-C-cyano-C-ethoxy-carbonyl-formaldehydeoxime in 25 parts by volume of tetrahydrofurane was added dropwise, while keeping the pH of the solution at 7.5 by appropriate addition of triethylamine. Thereafter the mixture was stirred for 90 minutes at 22° C, 100 parts by volume of water were added, the solution was adjusted to pH 6.5, the tetrahydrofurane was largely removed in vacuo in a rotary evaporator, and the remaining aqueous solution was covered with a 1 : 1 mixture of ether and ethyl acetate, stirred, cooled to 0° – 5° C and acidified to pH 1.5 with 2 N hydrochloric acid.

The organic phase was separated off, washed with water and dried over sodium sulphate in a refrigerator, and the sodium salt of the penicillin was precipitated by means of 1 M solution of sodium 2-ethylhexanoate in ether containing methanol. The supernatant solution was decanted from the initially oily precipitate, and the latter was converted into a colourless powder by trituration with dry ether.

β-Lactam content: 82%. NMR signals at τ = 2.4–3.0 (5 H), 4.3–4.7 (3 H), 5.2 (1 H), 5.8 (1 H), 6.8 (3 H) and 7.9–9.0 ppm (16 H).

The biological activity of this penicillin (A) and of the penicillin (B) prepared from ampicillin and N-cyclohexyloxycarbonyl-N-methyl-carbamic acid chloride were identical within the limit of error, as is shown by the Table below. Minimum inhibitory concentration in units/ml:

| | A | B |
| --- | --- | --- |
| *E. coli* 14 | 3.12 | 1.56 |
| *E. coli* A 261 | 400 | 400 |
| *E. coli* C 165 | 6.25 | 6.25 |
| *E. coli* 183/58 | 3.12 | 1.56 |
| *Proteus* 3400 | 12.5 | 6.25 |
| *Proteus* 1017 | 12.5 | 6.25 |
| *Pseudomonas aerug.* Bonn | 25 | 25 |
| *Pseudomonas aerug.* Walter | 50 | 50 |
| *Klebsiella* E 10 | 200 | 100 |
| *Klebsiella* 63 | 100 | 100 |
| *Staphylococcus aureus* 1777 E | 200 | 400 |
| *Staphylococcus aureus* 133 | <0.7 | <0.7 |
| *Enterococcus* ATCC 9790 | 100 | 100 |

EXAMPLE 30

Sodium D(−)-α-(3-allyloxycarbonyl-3-methyl-ureido)-benzylpenicillin:

7.1 parts by weight of 6-aminopenicillanic acid were dissolved in a mixture of 120 parts by volume of methylene chloride and 10 parts by volume of triethylamine, 12.4 parts by weight of O-[D(−)-α-(3-allyloxycarbonyl-3-methylureido)-phenylacetyl]-C-cyano-C-ethoxycarbonyl-formaldehydeoxime were added, the solution was left to stand for 24 hours in a refrigerator, diluted with 150 parts by volume of methylene chloride and exhaustively extracted by shaking with sodium bicarbonate solution, the combined bicarbonate extracts were covered with a 1 : 1 mixture of ether and ethyl acetate, the pH of the aqueous phase was adjusted to 5.0 with 2 N hydrochloric acid, while stirring, the organic phase was separated off, the aqueous phase was covered with fresh ether-ethyl acetate mixture, the aqueous phase was then acidified to pH 1.5 with 2 N hydrochloric acid, while stirring and cooling with ice, the organic phase was separated off, and the sodium salt of the penicillin was precipitated and isolated in the manner described in Example 29.

Yield: 30%.

β-Lactam content: 74%.

Calculated: C 49.7 H 5.2 N 10.5 S 6.1

Found: C 49.9 H 6.1 N 10.4 S 5.6 NMR signals at = 2.4–2.8 (5H), 3.7–4.3 (1 H), 4.4–4.9 (5 H), 5.1–5.4 (2H), 5.8 (1 H), 6.8 (3 H) and 8.45 ppm (6 H).

The biological effectiveness of this penicillin (A) and of the penicillin (B) prepared from ampicillin and N-allyloxycarbonyl-N-methyl-carbamic acid chloride were identical within the limit of error, as is shown by the Table below. Minimum inhibitory concentration in units/ml:

| | A | B |
| --- | --- | --- |
| *E. coli* 14 | 0.8–4 | 3.12 |
| *E. coli* A 261 | 100–500 | >400 |
| *E. coli* C 165 | 4–20 | 12.5 |
| *E. coli* 183/58 | 4–20 | 6.25 |
| *Proteus* 3400 | 20–100 | 25 |
| *Proteus* 1017 | 20–100 | 12.5 |
| *Pseudomonas aerug.* Bonn | 4–20 | 12.5 |
| *Pseudomonas aerug.* Walter | 20–100 | 12.5 |
| *Klebsiella* K 10 | 20–100 | 50 |
| *Klebsiella* 63 | 20–100 | 25 |
| *Staphylococcus aureus* 133 | 0.8–4 | 0.78 |
| *Enterococcus* ATCC 9790 | 20–100 | 50 |

EXAMPLE 31

Sodium α-(3-benzoyl-3-methyl-ureido)-2,6-dichlorobenzyl-penicillin

This penicillin was prepared in the manner described in Example 30 from 2.82 parts by weight of 6-aminopenicillanic acid, 6.0 parts by weight of O[α-(3-benzoyl-3-methylureido)-2,6-dichlorophenylacetyl]-C-cyano-C-ethoxycarbonyl-formaldehydeoxime, 50 parts by volume of methylene chloride and 4 parts by volume of triethylamine.

Yield: 40%.

β-Lactam content: 80%.

Calculated: C 47.4; H 4.3 N 8.8 S 5.0

Found: C 47.1 H 4.7 N 8.9 S 5.4

NMR signals at τ = 2.4–2.9 (8 H), 3.3 (0.6 H), 3.8 (0.4 H), 4.45 (2 H), 5.8 (1 H), 6.8 (0.6 H). 6.85 (0.4 H) and 8.45 ppm (6 H).

EXAMPLE 32

Sodium α-(3-benzoyl-3-methyl-ureido)-2,6-dichlorobenzyl-penicillin 5.6 parts by weight of α-(3-benzoyl-3-methylureido)-2,6-dichlorophenylacetic acid were dissolved in a mixture of 70 parts by volume of dry acetone and 2.5 parts by volume of triethylamine at −5° C to −10° C, 2.9 parts by weight of 1-methyl-2-chloro-pyrrolinium chloride were added, the mixture was stirred for 45 minutes, the precipitate thereby formed (triethylamine hydrochloride) was filtered off, the filtrate was combined with a solution of 4.3 parts by weight of 6-aminopenicillanic acid in water which was prepared with the aid of triethylamine, had a pH of 7.5 and was cooled to −10° C, the mixture was subsequently stirred for 2 hours at −5° C, and the pH was at the same time kept at 7.5 by appropriate addition of triethylamine. The mixture was then diluted with 130 parts by volume of water, the pH was adjusted to 6.5 by means of 2 N hydrochloric acid, the acetone was stripped off in vacuo, the solution which remained was adjusted to pH 7.5 and extracted by shaking with a 1 : 1 mixture of ether and ethyl acetate, the aqueous phase was separated off covered with fresh organic phase, and acidified to pH 1.5 with 2 N hydrochloric acid, while stirring and cooling in ice, the organic phase was separated off, washed with water and dried for 2 hours in a refrigerator over sodium sulphate, and the sodium salt of the penicillin was precipitated and isolated in the manner described in Example 27.
Yield: 33%.
β-Lactam content: 78%.
NMR signals at τ = 2.4–2.75 (8 H), 3.3 (0.7 H), 3.7 (0.3 H), 4.4 (2 H), 5.75 (1 H), 6.8 (3 H) and 8.45 ppm (6 H).
Effectiveness in animal experiments : A and B

EXAMPLE 33

Sodium α-(3-benzoyl-3-methyl-ureido)-4-methylthiobenzyl-penicillin:

This penicillin was prepared, as described in Example 32, from 6.0 parts by weight of α-(3-benzoyl-3-methylureido)-4-methylthiophenylacetic acid, dissolved in 70 parts by volume of acetone and 2.35 parts by volume of triethylamine, after reaction with 2.7 parts by weight of 1-methyl-2-chloropyrrolinium chloride, by combination with a solution of 6-aminopenicillanic acid in water, of pH 7.5, prepared by addition of triethylamine.
Yield: 45%.
β-Lactam content: 72%.
NMR signals at τ = 2.4–2.9 (9 H), 4.4 (1 H), 4.5 (2 H), 5.8 (1 H), 6.9 (3 H), 7.6 (3 H) and 8.45 ppm (6 H).
Effectiveness in animal experiments : A and B

EXAMPLE 34

Sodium α-(3-ethoxycarbonyl-3-methyl-ureido)-4-methylthiobenzylpenicillin:

This penicillin was prepared in the manner described in Example 32 from 6.0 parts by weight of α-(3-ethoxycarbonyl-3-methylureido)-4-methylthiophenylacetic acid, 80 parts by volume of acetone, 2.6 parts by volume of triethylamine and 3.0 parts by weight of 1-methyl-2-chloropyrrolinium chloride, by combination with a solution of 4.4 parts by weight of 6-aminopenicillanic acid in 70 parts by volume of 50% strength aqueous acetone, prepared by addition of triethylamine.
Yield: 44%.
β-Lactam content: 78%.
NMR signals at τ = 2.6 (2 H), 2.75 (2 H), 4.5 (1 H), 4.55 (2 H), 5.5–5.9 (3 H), 6.85 (3 H), 7.55 (3 H), 8.4 (6 H) and 8.6 ppm (3 H).

EXAMPLE 35

Sodium α-(3-ethoxycarbonyl-3-methyl-ureido)-4-methylthiobenzylpenicillin:

To prepare this penicillin, 6.0 parts by weight of α-(3-ethoxycarbonyl-3-methylureido)-4-methylthiophenylacetic acid were dissolved in 80 parts by volume of acetone, with the addition of 2.6 parts by volume of triethylamine, 3.0 parts by weight of 1-methyl-2-chloro-pyrrolinium chloride were added at −5° C to −10° C, the mixture was stirred for 45 minutes at the same temperature, a solution of 4.4 parts by weight of 6-aminopenicillanic acid in a mixture of 70 parts by volume of 50% strength aqueous acetone and triethylamine, which had a pH of 7.5, was added, the mixture was subsequently stirred for 2 hours at −5° C and diluted with 150 parts by volume of water, and the reaction mixture was worked up as in Example 32, to isolate the sodium salt of the penicillin. Yield: 44%.
β-Lactam content: 78%.
Calculated: C 46.7 H 5.2 N 9.9 S 11.3
Found: C 47.0 H 5.6 N 9.4 S 10.8
NMR signals as indicated in Example 34. The spectra of both substances are identical.
Effectiveness in animal experiments: A

EXAMPLE 36

Sodium α-(3-β-chloropropionyl-3-methyl-ureido)-cyclohex-3-enylmethylpenicillin:

This penicillin was prepared in the manner described in Example 32, from 5.3 parts by weight of α-(3-β-chloropropionyl-3-methylureido)-cyclohex-3-enyl-acetic acid, after reaction with 3.0 parts by weight of 1-methyl-2-chloro-pyrrolinium chloride in the presence of 2.6 parts by volume of triethylamine, by reaction with 4.4 parts by weight of 6-aminopenicillanic acid which had been dissolved in 50% strength aqueous acetone, at pH 7.5, by means of triethylamine.
Yield: 44%.
β-Lactam content: 78%.
NMR signals at τ = 4.3 (2 H), 4.5 (2 H), 5.8 (1 H), 6.2 (2 H), 6.65 (3 H), 6.8 (2 ) and 7.7 - 8.8 ppm (13 H).

EXAMPLE 37

Sodium D(−)-α-[3-(2-thenoyl)-3-methyl-ureido]-benzyl-penicillin

To prepare this penicillin, 3.9 parts by weight of D(−)-α-[3-(2-thenoyl)-3-methyl-ureido]-phenylacetic acid were dissolved in 55 parts by volume of acetone with the addition of 2.0 parts by volume of triethylamine, 2.3 parts by weight of 1-methyl-2-chloropyrrolinium chloride were added at −5° C to −10° C, the mixture was stirred for 45 minutes at the same temperature, a solution of 3.1 parts by weight of 6-aminopenicillanic acid in a mixture of 60 parts by volume of 90% strength aqueous acetone and triethylamine, which had a pH of 7.5, was added, and the mixture was stirred for 2 hours at −5° C and worked up — as described in Example 32 — to isolate the sodium salt of the penicillin.
Yield: 56%.
β-Lactam content: 64%.
NMR signals at $\tau$ = 2.1–3.0 (8 H), 4.35–4.8 (3 H), 5.8 (1 H), 6.55 (3 H) and 8.45 ppm (6 H).

EXAMPLE 38

Sodium D(−)-α-[3-(3,5-dimethylisoxazoloyl-4)-3-methyl-ureido]-benzylpenicillin:

To prepare this penicillin, 3.9 parts by weight of D-α-[3-(3,5-dimethylisoxazoloyl-4)-3-methyl-ureido]-phenylacetic acid were dissolved in 60 parts by volume of methylene chloride with the addition of 2.0 parts by volume of triethylamine, the solution was cooled to −10° C, 2.2 parts by weight of 1-methyl-2-chloropyrrolinium chloride was added, and the mixture was left to stand for 90 minutes at −10° to −35° C (solution A).

Separately, 3.1 parts by weight of 6-aminopenicillanic acid were suspended in 60 parts by volume of methylene chloride, 3.4 parts by volume of triethylamine were added, and the mixture was stirred for 4 hours at 22° C (solution B). Solution B was then cooled to between 0° and −5° C, and solution A was added in several portions, over the course of 30 minutes, while stirring and continuing to cool.

Thereafter the mixture was stirred for a further hour at 0° to 5° C, the solvent was stripped off in vacuo, the residue was taken up in water and a 1 : 1 mixture of ether and ethyl acetate, the pH was adjusted to 7.5 while stirring, the organic phase was separated off, the aqueous phase was covered with fresh ether-ethyl acetate mixture, the pH was brought to 1.5 by means of 2 N hydrochloric acid, while stirring and cooling with ice, the organic phase was separated off, washed with water and dried over magnesium sulphate for 2 hours in a refrigerator, and the penicillin was isolated as the sodium salt, as described in Example 32.
Yield: 50%
β-Lactam content: 80%.
Calculated C 50.7 H 5.0 N 12.3 S 5.6
Found: C 51.1 H 5.4 N 11.6 S 5.8
NMR signals at $\tau$ = 2.35–2.9 (5 H), 4.4 (1 H), 4.5 (2 H), 5.8 (1 H), 6.8 (3 H), 7.6 (3 H), 7.75 (3 H) and 8.45 ppm (6 H).

EXAMPLE 39

If, in the procedure of Example 37, the D(−)-α-[3-(2-thenoyl)-3-methylureido]-phenylacetic acid used there is replaced by 0.012 mol of:

D(−)-α-[3-(2-furoyl)-3-methyl-ureido]-phenylacetic acid,
D(−)-α-[3-(2-furoyl)-3-ethyl-ureido]-phenyl-acetic acid,
D(−)-α-[3-(2-furoyl)-3-n-propyl-ureido) -phenylacetic acid,
D(−)-α-[3-(2-furoyl)-3-phenyl-ureido]-phenylacetic acid,
D(−)-α-[3-(2,5-dimethylfuroyl-3-)-3-methyl-ureido]-phenylacetic acid,
D(−)-α[3-(5-bromofuroyl-3-)-3-methyl-ureido]-phenylacetic acid,
D(−)-α-[3-(5-methoxymethylfuroyl-2-)-3-methyl-ureido]-phenylacetic acid,
D(−)-α-[3-(3,5-dimethylisothiazol-3-yl)-carbonyl)-3-methyl-ureido]phenylacetic acid,
D(−)-α-[3-(isoxazol-4-yl)-carbonyl-3-methyl-ureido]-phenylacetic acid,
D(−)-α-[3-(isoxazol-3-yl)-carbonyl-3-methyl-ureido]-phenylacetic acid,
D(−)-α-[3-(3-methylthiodiazol(1,2,5)-4-yl)-carbonyl-3-methyl-ureido]-phenylacetic acid or
D(−)-α-[3-(4-methylthiadiazol(1,2,3)-5-yl)-carbonyl-3-methyl-ureido]-phenylacetic acid the sodium salts of the following penicillins are obtained:

D(−)-α-[3-(2-furoyl)-3-methyl-ureido]-benzyl-penicillin,
D(−)-α-[3-(2-furoyl)-3ethyl-ureido]-benzylpenicillin,
D(−)-α-[3-(2-furoyl)-3-n-propyl-ureido]-benzyl-penicillin,
D(−)-α-[3-(2-furoyl)-3-phenyl-ureido]-benzyl-penicillin,
D(−)-α-[3-(2,5-dimethylfuroyl-3)-3-methyl-ureido-benzylpenicillin,
D(−)-α-[3-(5-bromofuroyl-3)-3-methyl-ureido]-benzylpenicillin,
D(−)-α-[3-(5-methoxymethylfuroyl-2)-3-methyl-ureido]-benzylpenicillin,
D(−)-α-[3-(3,5-dimethylisothiazol-3-yl)-carbonyl-3-methyl-ureido]-benzylpenicillin,
D(−)-α-[3-(isoxazol-4-yl)-carbonyl-3-methyl-ureido]-benzylpenicillin,
D(−)-α-[3-isoxazol-3-yl)-carbonyl-3-methyl-ureido)]-benzylpenicillin,
D(−)-α-[3-(3-methylthiodiazol(1,2,5)-4-yl)-carbonyl-3-methyl-ureido]-benzylpenicillin or
D(−)-α-[3-(4-methylthidiazol(1,2,3)-5-yl)-carbonyl-3-methyl-ureido]-benzylpenicillin.

EXAMPLE 40

A. D(−)-α-(3-Cyclohexyloxycarbonyl-3-methyl-ureido)-phenyl-acetic acid 13.5 parts by weight of bis-(trimethylsilyl)-C-phenylglycine were dissolved in 100 parts by volume of dry carbon tetrachloride, a solution of 10.0 parts by weight of N-cyclohexyloxycarbonyl-N-methyl-carbamic acid chloride in 30 parts by volume of carbon tetrachloride was slowly added dropwise at 0° C while excluding moisture, and the mixture was left to stand overnight in a refrigerator. Thereafter it was washed 3 times with 50 parts by volume of water at a time, and the organic phase was evaporated to dryness in vacuo.
Yield of oily product: 95%.
NMR signals at $\tau$ = 0.5 (1 H), 2.5 (5 H), 4.6 (1 H), 5.2 (1 H), 6.8 (3 H) and 7.9–8.9 ppm (10 H).

B. O-[D(−)-α-(3-Cyclohexyloxycarbonyl-3-methyl-ureido)-phenylacetyl]-C-cyano-C-ethoxycarbonyl-formaldehydeoxime 2.92 parts by weight of C-cyano-C-ethoxycarbonyl-formaldehydeoxime were dissolved in 50 parts by volume of tetrahydrofurane, 2.9 parts by volume of triethylamine were added, the mixture was cooled to −10° C, 1.5 parts by volume of thionyl chloride were then slowly added dropwise while stirring and continuing to cool, and the mixture was subsequently stirred for 15 minutes at −10° C. A solution, cooled to 0° C, of 6.88 parts by weight of D(−)-α-(3-cyclohexyloxycarbonyl-3-methyl-ureido)-phenylacetic acid in a mixture of 50 parts by volume of tetrahydrofurane and 2.9 parts by volume of triethylamine was then added dropwise over the course of approx. 45 minutes while continuing to cool, and the reaction mixture was subsequently stirred for a further hour at 0° C. The triethylamine hydrochloride which had separated out was then filtered off, the filtrate was evaporated in vacuo from a bath at 15°–20° C using a rotary evaporator, the residue was dissolved in methylene chloride, the solution was cooled to 0° C and once shaken rapidly with ice water, and the organic phase was subsequently dried at 0° C over sodium sulphate, filtered, and evaporated in vacuo by means of a rotary evaporator, from a bath at 20° C, and finally from a bath at 40° C. A colourless, varnish-like substance is obtained.

Yield: 98%.
Specific rotation: $[\alpha]_{589}$ −8.1° (54.2 mg; methanol).
The substance showed an IR spectrum corresponding to its structure.
NMR signals at $\tau$ = 0.5 (1 H), 2.6 (5 H), 4.3 (1 H), 5.25 (1 H), 5.7 (2 H), 6.8 (3 H) and 8.0–9.0 ppm (13 H).

EXAMPLE 41

O-[D(−)-α-(3-Allyloxycarbonyl-3-methyl-ureido)-phenylacetyl]-C-cyano-C-ethoxycarbonyl-formaldehydeoxime This substance was prepared in the manner described in Example 40, from 5.86 parts by weight of C-cyano-C-ethoxycarbonyl-formaldehydeoxime, 100 parts by volume of tetrahydrofurane, 57 parts by volume of triethylamine, 3.0 parts by volume of thionyl chloride and a mixture of 12.0 parts by weight of D(−)-α-(3-allyloxycarbonyl-3-methyl-ureido)-phenylacetic acid, 100 parts by volume of tetrahydrofurane and 5.7 parts by volume of triethylamine. A colorless, varnish-like substance is obtained.

Yield: over 80%.
Specific rotation: $[\alpha]_{589}$ −19.8° (50.6 mg; methanol).
The substance showed an IR spectrum corresponding to its structure.
NMR signals at $\tau$ = 0.4 (1 H), 2.6 (5 H), 3.7–4.2 (1 H), 4.3 (1 H), 4.5–4.9 (2 H), 5.3 (2 H), 5.65 (2 H), 6.8 (3 H) and 8.65 ppm (3 H).

EXAMPLE 42

O-[D(−)-α-(3-benzoyl-3-methyl-ureido)-2,6-dichlorophenylacetyl]-C-cyano-C-ethoxycarbonyl-formaldehydeoxime This substance was prepared in the manner described in Example 40, from 2.85 parts by weight of C-cyano-C-ethoxycarbonyl-formaldehydeoxime, 50 parts by volume of tetrahydrofurane, 2.8 parts by volume of triethylamine, 1.45 parts by volume of thionyl chloride and a mixture of 7.6 parts by weight of D(−)-α-(3-benzoyl-3-methyl-ureido)-2,6-dichlorophenylacetic acid, 50 parts by volume of tetrahydrofurane and 2.8 parts by volume of triethylamine. A colorless, varnish-like substance was obtained.

Yield: over 80%.
The IR spectrum of the substance showed the bands corresponding to its structure.
NMR signals at $\tau$ = 0.5 (1 H), 2.45 (5 H), 3.55 (1 H), 5.65 (2 H), 6.9 (3 H) and 8.7 (3 H).

EXAMPLE 43

Sodium α-(pyrrolid-2-on-1-yl-carbonylamino)-α-p-tolyl-methylpenicillin

This penicillin was prepared in the manner described in Example 1, from 14.5 parts by weight of α-pyrrolid-2-on-1-ylcarbonylamino)-α-p-tolylacetic acid, 10.2 parts by weight of tetramethyl-chloroformamidinium chloride and 15 parts by weight of 6-amino-penicillanic acid.

Yield: 29%
β-Lactam content: 67%
NMR signals at $\tau$ = 2.5 – 3.05 (4 H), 4.5 (3 H), 5.8 (1 H), 6.1 – 6.4 (2 H), 7.4 (2 H), 7.7 (3 H), 8.0 (2 H) and 8.3 – 8.6 ppm (6 H).

EXAMPLE 44

Sodium α-(3-fluorobenzoyl-3-methyl-ureido)-α-p-tolyl-methylpenicillin

This penicillin was prepared in the manner indicated in Example 2, from 9 parts by weight of N-o-fluorobenzoyl-N-methylureido-N-p-tolylacetic acid, 4.95 parts by weight of tetramethyl-chloroformamidinium chloride and 8.5 parts by weight of 6-amino-penicillanic acid.

Yield: 59%
β-Lactam content: 87%
Calculated: C 53.7 H 4.8 N 9.7 S 5.5
Found: C 53.4 H(6.0) N 9.7 S 5.9.
NMR signals at $\tau$ = 2.3 – 3.1 (8 H), 4.5 (3 H), 5.8 (1 H), 6.3 (3 H), 7.7 (3 H) and 8.2 – 8.5 ppm (6 H).
Effectiveness in animal experiments: A and B.

EXAMPLE 45

Sodium α-[(imidazolidin-2-on-1-yl)-carbonylamino]-p-methyl-benzylpenicillin 3.76 parts by weight of tetramethylchloroformamidinium chloride were suspended in 15 parts by volume of dry acetone and stirred for 10 minutes with exclusion of moisture. The product was filtered off, again with exclusion of moisture, and the reagent was suspended in 40 parts by volume of methylene chloride and cooled to 0° C. 5.53 parts by weight of α-[(imidazolidin-2-on-1-yl)-carbonylamino]-p-methylphenylacetic acid in a little methylene chloride were now added and a solution of 2.0 parts by weight of triethylamine in 20 parts by volume of methylene chloride was added dropwise to the mixture over the course of 30 minutes, while stirring and excluding moisture. The mixture was stirred for a further 20 minutes at +5° C and then cooled to −20° C and treated, all at once, with a solution of the triethylamine salt of 6-aminopenicillanic acid in methylene chloride, also cooled to −20° C. (This solution had been prepared by stirring 5.8 parts by weight of 6-aminopenicillanic acid, 3.4 parts by weight of triethylamine and 8 parts by weight of anhydrous sodium sulphate in 40 parts by volume of methylene chloride for two hours, and subsequent filtering). The mixture was left to reach 0° C while stirring, was treated with a further 0.9 part by weight of triethylamine after a short time, and was further stirred for 30 minutes at 0° C and 30 minutes at room temperature. It was now poured into ice water, the pH value was adjusted to 5.5 and the methylene chloride was stirred off in vacuo. The residue was twice extracted with ether and the ether was eluted with a little water. The combined aqueous solutuons were covered with a layer of ethyl acetate and adjusted to a pH value of 1.5 with dilute hydrochloric acid while stirring and cooling with ice. The ethyl acetate phase was separated off, the water was again extracted with ethyl acetate, and the combined extracts were washed with water. They were dried for about one hour at 0° C over $MgSO_4$, filtered and treated with 20 parts by volume of a 1 molar solution of sodium 2-ethylhexanoate in ether containing methanol, and the mixture was evaporated in vacuo at room temperature until it acquired an oily consistency. It was now dissolved in the requisite amount of methanol and this solution was added dropwise to 500 parts by volume of a mixture of about 500 parts by volume of absolute ether and 50 parts by volume of methanol, while stirring vigorously. The product which precipitated was filtered off after standing for a short time, suspended in dry ether and again filtered off. It was dried in vacuo over $P_2O_5$ for about 2 days.

Yield: 70%
β-Lactam content: 86%
NMR signals, see Table 2, page 96,
IR bands at 3280, 1760, 1712, 1655, 1600, 1520, 1270 and 765 $cm^{-1}$ (in Nujol suspension).

EXAMPLE 46

Sodium α-[(imidazolidin-2-on-1-yl)-carbonylamino]-p-methylbenzylpenicillin 2.8 parts by weight of α[(imidazolidin-2-on-1-yl)-carbonylamino]-p-methylphenylacetic acid were reacted, in the manner described in Example 45, with 1.7 parts by weight of 1-methyl-2-chloro-Δ 1-pyrrolinium chloride instead of tetramethyl-chloroformamidinium chloride, and subsequently with 2.6 parts by weight of 6-aminopenicillanic acid in the form of its triethylamine salt, to give the sodium salt of α[(imidazolidin-2-on-1-yl)-carbonylamino]-p-methylbenzylpenicillin.
Yield: 54%
β-Lactam content: 39%
NMR signals, see Table 2, page 96.
The position of the IR bands agrees with that of the penicillin of Example 45.

EXAMPLE 47

Sodium α-[(imidazolidin-2-on-1-yl)-carbonylamino]-p-chloro benzylpenicillin

This penicillin was manufactured in the manner described in Example 1, from 5.95 parts by weight of α-[(imidazolidin-2on-1-yl)-carbonylamino]-p-chlorophenylacetic acid, 3.76 parts by weight of tetramethyl-chloroformamidinium chloride and 5.8 parts by weight of 6-aminopenicillanic acid.

Yield: 59%
β-Lactam content: 86%
NMR signals, see Table 2, page 97.
IR bands at 3300, 1775, 1727, 1667, 1608, 1540, 1287 and 780 $cm^{-1}$.

EXAMPLE 48 A

Sodium α-[(imidazolidin-2-on-1-yl)-carbonylamino]-p-chlorobenzylpenicillin 3.6 parts by weight of α[(imidazolidin-2-on-1-yl)carbonylamino]-p-chlorophenylacetic acid were reacted in the manner described in Example 1 with 2.22 parts by weight of 1,3-dimethyl-2-chloro-Δ-1-imidazolinium chloride and subsequently with 3.02 parts by weight of 6-aminopenicillanic acid to give the sodium salt of α-[(imidazolidin-2-on-1-yl)carbonylamino]-p-chlorobenzylpenicillin.
Yield: 65%
β-lactam content: 72%
NMR signals, see Table 2, page 97. The IR spectrum in Nujol is identical with that of the penicillin of Example 47.

EXAMPLE 48 B

α-[(Imidazolidin-2-on-1-yl)-carbonylamino]-p-methylphenylacetic acid 16.5 parts by weight of α-(4-methylphenyl)-glycine were dissolved in 200 parts by volume of 50% strength aqueous dioxane, with the addition of sufficient 2 N sodium hydroxide solution. Thereafter the mixture was adjusted back to a pH value of 7-8 with 5 N hydrochloric acid, whereupon the aminoacid separated out partially as a fine precipitate. A solution of 11.8 parts by weight of 1-chlorocarbonyl-imidazolidin-2-one in 50 parts by volume of warm acetone was now added dropwise, while stirring and cooling by means of an ice bath. The pH was at the same time maintained at between 7 and 8 by appropriate addition of 2 N sodium hydroxide solution. After completion of the addition, the mixture was stirred for a further 15 minutes at room temperature until the pH value remained constant. Unreacted aminoacid (6 parts by weight) was filtered off, and the filtrate was evaporated to half its volume in vacuo and extracted once with 100 parts by volume of ether. The aqueous phase was adjusted to a pH of 1-2 with 2 N hydrochloric acid and the oil which precipitated was taken up in ethyl acetate by extraction with 2 × 100 parts by volume. The combined ethyl acetate extracts were washed with 50 parts by volume of water, dried over $MgSO_4$ and subsequently evaporated in dryness. A glassy foam was obtained, which through trituration with petroleum ether was converted into a finely granular, non-crystalline powder.
Yield: 48%. NMR signals, see Table 2, page 97.

EXAMPLE 48 C

The following α-[(imidazolidin-2-on-1-yl)-carbonylamino]-phenylacetic acid was produced as described in Example 48 B:
α-[(Imidazolidin-2-on-1-yl)-carbonylamino]-p-chlorophenylacetic acid from 18.6 parts by weight of α-(4-chlorophenyl)-glycine and 11.8 parts by weight of 1-chlorocarbonylimidazolidin-2-one. Recovered unreacted α-(4-chlorophenyl)glycine: 6 parts by weight.
Yield of product moist with ether: 33 parts by weight.

The substance was recrystallised from ethyl acetate/petroleum ether.

1st fraction, yield: 35% relative to converted starting
2nd fraction, yield: 15% material.

Melting point = 115°–120° C. NMR signals, see Table 2, page 97.

EXAMPLE 48 D

1-Chlorocarbonyl-imidazolidin-2-one 4 parts by weight of phosgene in 10 parts by volume of absolute tetrahydrofurane were added dropwise, over the course of 15 minutes, to a vigorously stirred solution of 3.5 parts by weight of imidazolidone-(2) [manufactured according to Fischer and Koch, Ann. 232, page 224 (1886)] in 50 parts by volume of absolute tetrahydrofurane. Thereafter the reaction mixture was stirred for 3 hours at 10° C and a stream of dry air was then passed through it to blow out the hydrochloric acid produced, and residues of phosgene. It was now evaporated to dryness in vacuo on a rotary evaporator, and the solid residue was dried over concentrated sulphuric acid at about 12 mm Hg.

Yield: 93%. Melting point = 150° C after recrystallisation from acetone-pentane.

Calculated: C 32.3 H 3.4 N 18.8 Cl 23.9
Found: C 32.3 H(4.5) N 18.7 Cl 23.9

NMR signals at $\tau$ = 5.7 to 6.1 (2 H) and 6.3 to 6.7 (2 H), (acetone-$d_6$ as the solvent), symmetrical $A_2B_2$-system.

IR bands at 3230, 1790, 1700, 1270 and 1150 $cm^{-1}$.

EXAMPLE 48 E

If, in the procedure of Example 45, the α-[(imidazolidin-2-on-1-yl)-carbonylamino]-p-methylphenylacetic acid used therein is replaced by 0.02 mol of one of the following:

α-[(imidazolidin-2-on-1-yl)-carbonylamino]-thienyl(2)-acetic acid,

α-[(imidazolidin-2-on-1-yl)-carbonylamino]-thienyl(3)-acetic acid,

α-[(imidazolidin-2-on-1-yl)-carbonylamino]-p-hydroxyphenylacetic acid,

α-[(imidazolidin-2-on-1-yl)-carbonylamino]-m-hydroxyphenylacetic acid,

α[(imidazolidin-2-on-1-yl)-carbonylamino]-o-chlorophenylacetic acid,

α-[(imidazolidin-2-on-1-yl)-carbonylamino]-o,o'-difluorophenylacetic acid,

α-[(imidazolidin-2-on-1-yl)-carbonyl-amino]-o,o'-chlorofluorophenylacetic acid or α-[(imidazolidin-2-on-1-yl)-carbonylamino]-p-acetylaminophenylacetic acid, the following penicillins are obtained in the form of their sodium salts:

α-[(imidazolidin-2-on-1-yl)-carbonylamino]-thienyl(2)-methylpenicillin,

α-[(imidazolidin-2-on-1-yl)-carbonylamino]-thienyl(3)-methylpenicillin,

α-[(imidazolidin-2-on-1-yl)-carbonylamino]-p-hydroxybenylpenicillin,

α-[(imidazolidin-2-on-1-yl)-carbonylamino]-m-hydroxybenzylpenicillin,

α-[(imidazolidin-2-on-1-yl)-carbonylamino]-o-chlorobenzylpenicillin,

α-[(imidazolidin-2-on-1-yl)-carbonylamino]o,o'-difluorobenzylpenicillin,

α-[(imidazolidin-2-on-1-yl)-carbonylamino]-o,o'-chlorofluorobenzylpenicillin or

α-[(imidazolidin-2-on-1-yl)-carbonylamino]-p-acetylaminobenzylpenicillin.

EXAMPLE 49

D(−)-α-[(Imidazolidin-2-on-1-yl)-carbonylamino]-phenylacetic acid 9.7 parts by weight of D(−)-C-phenylglycine were suspended in 150 parts by volume of 50% strength aqueous dioxane and sufficient 40% strength aqueous sodium hydroxide solution waas added dropwise at room temperature, while stirring, for the phenylglycine to have just dissolved. Approximately 15% strength hydrochloric acid was then added to this solution, while stirring, until the pH of the solution had reached 7.5 –8.0. The fine suspension of the phenylglycine which is present at that stage was cooled to about +5° C, 10.6 parts by weight of finely powdered imidazolidin-2-on-1-yl-carbonyl chloride were gradually introduced at this temperature, while stirring, and at the same time the pH was kept at 7.5 – 8.0 by appropriate addition of approximately 5 N sodium hydroxide solution. The phenylglycine hereupon dissolved, apart from a small amount of residue. The mixture was stirred for a further 60 minutes at +5° C, during which time a little sodium hydroxide solution still had to be added occasionally in the first 15 minutes only, to maintain the desired pH. Small amounts of insoluble matter were then filtered off. The filtrate was largely freed of dioxane by means of a rotary evaporator, covered with a layer of ethyl acetate, acidified with 2 N hydrochloric acid to pH 1.5 –2.0 and thoroughly stirred, and the organic phase was then separated off, twice washed with water, dried over magnesium sulphate and completely evaporated in a rotary evaporator. The residue, a colorless clear foam, was dried for two days over $P_4O_{10}$ in a desiccator with an open tap, connected to an oil pump. Yield: 7.9 parts by weight. In the IR spectrum (solvent: dimethylsulphoxide), the substance shows two double bands in the region left open by the solvent, namely at 1720 and 1670, and at 1525 and 1480 $cm^{-1}$, respectively. NMR signals, see Table 2, page 97.

EXAMPLE 50

α-[(Imidazolidin-2-on-1-yl)-carbonylamino]-4-methylthiophenylacetic acid a. α-Amino-4-methylthiophenylacetic acid This aminoacid was obtained according to the usual procedure: starting from 4-metylthiobenzaldehyde, via the cyanhydrin and α-aminonitrile, and its saponification with boiling 20% strength hydrochloric acid. Melting point > 260° on the Kofler bench.

The IR spectrum (Nujol) shows a single band in the carbonyl region at 1740 $cm^{-1}$ and a broad absorption between 1570 and 1670 $cm^{-1}$, with a main peak at 1590 $cm^{-1}$.

The NMR spectrum (NaOD/$D_2O$) shows signals at $\tau$ = 2.5–2.8 (4H) (AB-system), at 5.6 (1 H) and at 7.6 ppm (3 H).

b. α-[(Imidazolidin-2-on-1-yl)-carbonylamino]-4-methylthiophenylacetic acid

This compound was manufactured from 13 parts by weight of the aminoacid described above and 10 parts by weight of imidazolidin-2-on-1-yl-carbonyl chloride, in the manner described in Example 5.

Yield: 6.7 parts by weight of a yellowish hard foam.

In the IR spectrum (solvent: dimethylsulphoxide) the substance shows two double bands in the range left open by the solvent, namely at 1710 and 1660, and at 1520 and 1480 cm$^{-1}$. NMR signals, see Table 2, pages 97.

EXAMPLE 51

Sodium D(−)-α-[(imidazolidin-2-on-1-yl)-carbonylamino]-benzylpenicillin 3.8 parts by weight of D(−)-α-[(imidazolidin-2-on-1-yl)-carbonylamino]-phenylacetic acid were dissolved in 65 parts by volume of dichloromethane, 2.7 parts by weight of 1-methyl-2-chloro-Δ1-pyrrolinium chloride were added, and after cooling to −10° C 2.0 parts by volume of triethylamine were added gradually. This reaction mixture was then stirred for one hour at −5° C (mixture A). 4.0 parts by weight of 6-aminopenicillanic acid in 80 parts by volume of dichloromethane were treated with 4.4 parts by volume of triethylamine and 4.0 parts by weight of anhydrous sodium sulphate and then stirred for two hours at room temperature. After filtration, the solution was cooled to −20° C and combined with the mixture A. The reaction mixture was left to reach 0° C of its own accord, and was then stirred for a further hour at 0° C. The solvent was now removed in a rotary evaporator, the residue was dissolved in water, and the solution was covered with a layer of ethyl acetate and acidified with dilute hydrochloric acid at 0° to 5° C, while stirring, until pH 1.5 was reached. The organic phase was then separated off, washed with water, dried over magnesium sulphate while cooling, and filtered, and after dilution with an equal amount of ether the sodium salt of the penicillin was precipitated from the filtrate by adding a solution of sodium 2-ethylcaproate dissolved in ether containing methanol.
Yield: 1.3 parts by weight.
β-Lactam content: 34%.
IR band at 1775 cm$^{-1}$. NMR signals, see Table 2, page 98.

EXAMPLE 52

D(−)-α-[(Imidazolidin-2-on-1-yl)-carbonylamino]-benzylpenicillin (free acid and sodium salt)

Mixture A was prepared in a corresponding manner to Example 51, from 3.8 parts by weight of D(−)-α-[(imidazolin-2-on-1-yl)-carbonylamino]-phenylacetic acid, 65 parts by volume of dichloromethane, 3.0 parts by weight of 1,3-dimethyl-2-chloro-Δ1-imidazolinium chloride and 2.0 parts by volume of triethylamine, and reacted with the dried solution prepared from 4.0 parts by weight of 6-aminopenicillanic acid, 80 parts by volume of dichloromethane, 4.4 parts by volume of triethylamine and 4.0 parts by weight of Na$_2$SO$_4$. After removing the solvent and distributing the reaction product between an aqueous phase of pH 1.5 and ethyl acetate, a precipitate which is neither soluble in the acid aqueous phase nor in the organic phase was formed and this was filtered off, washed with water and dried. This product was the free acid of the desired penicillin. Yield 1.5 parts by weight. The ethyl acetate phase which was above the acid aqueous phase was separated off, washed with water, dried over magnesium sulphate and diluted with ether, and the sodium salt of the penicillin was precipitated.
Yield: 1.9 parts by weight.
β-Lactam content (free acid): 92%.
β-Lactam content (sodium salt): 89%.
The two penicillins show an IR spectrum which corresponds to their structure. NMR signals, see Table 2, page 98.

EXAMPLE 53

D(−)-α-[(Imidazolidin-2-on-1-yl)-carbonylamino]-benzylpenicillin (free acid and sodium salt)

The penicillin was prepared in a manner corresponding to Example 52, from 3.8 parts by weighr of D(−)-α-[(imidazolidin-2-on-1-yl)-carbonylamino]-phenylacetic acid, 50 parts by volume of dichloromethane, 1.2 parts by weight of tetramethylchloroformamidinium chloride and 1.0 part by volume of triethylamine, constituting mixture A, and 2.0 parts by weight of 6-aminopenicillanic acid in 50 parts by volume of dichloromethane and 2.2 parts by volume of triethylamine as well as 2.0 parts by weight of sodium sulphate. 0.2 part by weight of penicillan was obtained as the free acid and 1.9 parts by weight as the sodium salt.
β-Lactam content (free acid): 90%.
β-Lactam content (sodium salt): 25%.
The free acid showed an IR spectrum corresponding to its structure.

EXAMPLE 54

Sodium α-[(imidazolidin-2-on-1-yl)-carbonylamino]-4-methylthiobenzylpenicillin

This penicillin was prepared in a manner corresponding to Example 51, from 4.5 parts by weight of α-[(imidazolidin-2-on-1-yl)-carbonylamino]-4-methylthio-phenylacetic acid, 80 parts by volume of dichloromethane, 2.7 parts by weight of 1-methyl-2-chloro-Δ1-pyrrolinium chloride and 2.0 parts by volume of triethylamine, constituting mixture A, and 4.0 parts by weight of 6-aminopenicillanic acid, 80 parts by volume of dichloromethane, 4.4 parts by volume of triethylamine and 4.0 parts by weight of sodium sulphate.
Yield: 4.2 parts by weight of sodium salt.
β-Lactam content: 36%.
NMR signals, see Table 2, page 98.

EXAMPLE 55

Sodium α-[(imidazolidin-2-on-1-yl)-carbonylamino]-4-methylthiobenzylpenicillin

This penicillin was obtained in a manner based on Example 51, from 1.9 parts by weight of α-[(imidazolidin-2-on-1-yl)-carbonylamino]-4-methylthio-phenylacetic acid, 40 parts by volume of dichloromethane, 1.2 parts by weight of tetramethylchloroformamidinium chloride and 0.98 part by volume of triethylamine constituting mixture A, and 1.73 parts by weight of 6-aminopenicillanic acid, 40 parts by volume of dichloromethane, 1.9 parts by volume of triethylamine and 1.5 parts by weight of sodium sulphate constituting mixtue B. Yield: 2.0 parts by weight of sodium salt. β-Lactam content: 61%. The penicillin showed an IR spectrum corresponding to its structure. NMR signals, see Table 2, page 98.

EXAMPLE 56

1,3-Dimethyl-2-chloro-Δ1-imidazolinium chloride
a. N,N'-Dimethyl-N,N'-bis-trimethylsilyl-ethylenediamine:
A mixture of 176 parts by weight of N,N'-dimethylethylenediamine, 1000 parts by volume of benzene and 552 parts by volume of triethylamine were stirred at room temperature and at the same time 434 parts by weight of trimethylchlorosilane, diluted with 500 parts by volume of benzene, were added dropwise over the course of 3 hours. The mixture was stirred for a further 3.5 hours and left to stand overnight, and the precipitate present was filtered off and washed with benzene. The combined filtrates were concentrated in a rotary evaporator and the residue was distilled in vacuo. Yield: 364 parts by weight.
Boiling point $_{0.15}$ = 55°–60° C.
The NMR spectrum ($CCl_4$ as the solvent) showed signals at −160 (4 H) and −148 Hz (6 H), with the signal of the trimethylsilyl radicals (9 H) being at 0 Hz.
Analysis: Calculated: C 51.7 H 12.1 N 12.1 Found: C 51.1 H 11.9 N 12.1.

b. N,N'-Dimethylimidazolidone-(2).

A solution of 363 parts by weight of N,N'-dimethyl-N,N'-bis-trimethylsilyl-ethylenediamine in 440 parts by volume of dichloromethane, and a solution of 170 parts by weight of phosgene in 700 parts by volume of dichloromethane, were simultaneously and separately added dropwise, over the course of 4.5 hours, to 800 parts by volume of dichloromethane at room temperature, while stirring. The reaction mixture was then left to stand overnight, the unreacted phosgene was flushed out with dry air, the solvent was removed in a rotary evaporator and the residue was distilled in vacuo. Yield 119 parts by weight. Boiling point $_{10-10.5\ mm\ Hg}$ = 95°–95.5° C.

c. 1,3-Dimethyl-2-chloro-Δ-1-imidazolinium chloride:

A solution of 150 parts by weight of 1,3-dimethylimidazolidone-(2) in 200 parts by volume of toluene was added to a solution of 156 parts by weight of phosgene in 330 parts by volume of toluene, and the mixture was left to stand overnight at room temperature. The product which had then crystallised out was filtered off, washed with carbon tetrachloride and dried over $P_4O_{10}$ in a desiccator.
Yield: 177 parts by weight.
Melting point: about 95°–100° C (Kofler bench). The product is crystalline and very hygroscopic. The NMR spectrum (solvent: chloroform) shows signals at $\tau$ = 5.6 (4 H) and 6.65 ppm (6 H).

EXAMPLE 57

If, in the procedure of Example 45, the α-[(imidazolidin-2-on-1-yl)-carbonylamino]-p-methylphenylacetic acid used therein is replaced by 0.02 mol of:
D(−)-α-[(1,3-diazacylohexan-2-on-1-yl)-carbonylamino]phenylacetate acid,
α-[(1,3-diazacyclohexan-2-on-1-yl)-carbonylamino]-p-methylphenylacetic acid,
α-[(1,3-diazacyclohexan-2-on-1-yl)-carbonylamino]-p-chlorophenylacetic acid,
α[(1,3-diazacyclohexan-2-on-1-yl)-carbonylamino]-p-methylthiophenylacetic acid,
α-[(diazacyclohexan-2-on-1-yl)-carbonylamino]-p-hydroxyphenylacetic acid,
α-[(1,3-diazacyclohexan-2-on-1-yl)-carbonylamino]-thienyl(2)-acetic acid,
α-[(1,3-diazacyclohexan-2-on-1-yl)-carbonylamino]-thienyl(3)-acetic acid,
D(−)-α-[(benzimidazolon-1-yl)-carbonylamino]-phenylacetic acid,
α-[(benzimidazolon-1-yl)-carbonylamino]-p-methylphenylacetic acid,
α-[(benzimidazolon-1-yl)-carbonylamino]-p-chlorophenylacetic acid,
α-[(benzimidazolon-1-yl)-carbonylamino]-p-methylthio-phenylacetic acid,
α-[(benzimidazolon-1-yl)-carbonylamino]-p-hydroxy-phenylacetic acid,
α-[(benzimidazolon-1-yl)-carbonylamino]-thienyl(2)-acetic acid,
α-[(benzimidazolon-1-yl)-carbonylamino]-thienyl(3)-acetic acid,
D(−)-α-[(5-methyl-imidazolidin-2-on-1-yl)-carbonylamino]-phenylacetic acid,
α-[(4-methylimidazolidin-2-on-1-yl)-carbonylamino]-p-methylphenylacetic acid,
α-[(5-methylimidazolidin-2-on-1-yl)-carbonylamino]-p-chlorophenylacetic acid,
α-[(5-methylimidazolidin-2-on-1-yl)-carbonylamino]-p-methylthiophenylacetic acid,
α-[(5-methylimidazolidin-2-on-1-yl)-carbonylamino]-p-hydroxyphenylacetic acid,
α-[(5-methylimidazolidin-2-on-1-yl)-carbonylamino]-thienyl(2)-acetic acid,
α-[(5-methylimidazolidin-2-on-1-yl)-carbonylamino]-thienyl(3)-acetic acid,
D(−)-α-[(5,5-dimethylimidazolidin-2-on-1-yl)-carbonylamino]-phenylacetic acid,
α-[(5,5-dimethylimidazolidin-2-on-1-yl)-carbonylamino]-p-methylphenylacetic acid,
α-[(5,5-dimethylimidazolidin-2-on-1-yl)-carbonylamino]-p-chlorophenylacetic acid,
α-[(4,5-dimethylimidazolidin-2-on-1-yl)-carbonylamino]-p-methylthiophenylacetic acid,
α-[(5,5-dimethylimidazolidin-2-on-1-yl)-carbonylamino]-p-hydroxyphenylacetic acid,
α-[(5,5-dimethylimidazolidin-2-on-1-yl)-carbonylamino]-thienyl(2)-acetic acid or
α-[(4,4-dimethylimidazolidin-2-on-1-yl)-carbonylamino]-thienyl(3)-acetic acid,
the following penicillins are obtained in the form of their sodium salts:
D(−)-α-[(1,3-diazacyclohexan-2-on-1-yl)-carbonylamino]-benzylpenicillin,
α-[(1,3-diazacyclohexan-2-on-1-yl)-carbonylamino]-p-methylbenzylpenicillin,
α-[(1,3-diazacyclohexan-2-on-1-yl)-carbonylamino]-p-chlorobenzylpenicillin,
α-[(1,3-diazacyclohexan-2-on-1-yl)-carbonylamino]-p-methylthio-benzylpenicillin,
α-[(1,3-diazacyclohexan-2-on-1-yl)-carbonylamino]-p-hydroxybenzylpenicillin,
α-[(1,3-diazacyclohexan-2-on-1-yl)-carbonylamino]-α-thienyl(2)methylpenicillin,
α-[(1,3-diazacyclohexan-2-on-1-yl)-carbonylamino]-α-thienyl(3)methylpenicillin,
D(−)-α-[(benzimidazolon-1-yl)-carbonylamino]-benzylpenicillin,
α-[(benzimidazolon-1-yl)-carbonylamino]-p-methyl-benzylpenicillin,
α-[(benzimidazolon-1-yl)-carbonylamino]-p-chlorobenzylpenicillin,
α-[(benzimidazolon-1-yl)-carbonylamino]-p-methylthio-benzylpenicillin,
α-[(benzimidazolon-1-yl)-carbonylamino]-p-hydroxy-benzylpenicillin,
α-[(benzimidazolon-1-yl)-carbonylamino]-α-thienyl(2)-methylpenicillin,
α-[(benzimidazolon-1-yl)-carbonylamino]-α-thienyl(3)methylpenicillin, D(−)-α-[(5-methylimidazolidin-2-on-1-yl)-carbonylamino]-benzylpenicillin,
α-[(4-methylimidazolidin-2-on-1-yl)-carbonylamino]-p-methylbenzylpenicillin,
α-[(5-methylimidazolidin-2-on-1-yl)-carbonylamino]-p-chlorobenzylpenicillin,
α-[(5-methylimidazolidin-2-on-1-yl)-carbonylamino]-p-methylthiobenzylpenicillin,
α-[(5-methylimidazolidin-2-on-1-yl)-carbonylamino]-p-hydroxybenzylpenicillin,
α-[(5-methylimidazolidin-2-on-1-yl)-carbonylamino]-α-thienyl(2)-methylpenicillin,
α-[(5-methylimidazolidin-2-on-1-yl)-carbonylamino]-α-thienyl(3)methylpenicillin,
D(−)-[(5,5-dimethylimidazolidin-2-on-1-yl)-carbonylamino]-benzylpenicillin,
α-[(5,5-dimethylimidazolidin-2-on-1-yl)-carbonylamino]-p-methylbenzylpenicillin,
α-[(5,5-dimethylimidazolidin-2-on-1-yl)-carbonylamino]-p-chlorobenzylpenicillin,
α-[(4,5-dimethylimidazolidin-2-on-1-yl)-carbonylamino]-p-methylthio-benzylpenicillin,
α-[(5,5-dimethylimidazolidin-2-on-1-yl)-carbonylamino]-p-hydroxybenzylpenicillin,
α-[(5,5-dimethylimidazolidin-2-on-1-yl)-carbonylamino]-α-thienyl(2)-methylpenicillin or
α-[(4,4-dimethylimidazolidin-2-on-1-yl)-carbonylamino]-α-thienyl(3)-methylpenicillin.

EXAMPLE 58

If, in the procedure of Example 45, the α-[(imidazolidin-2-on-1-yl)-carbonylamino]-p-methylphenylacetic acid used therein is replaced by 0.02 mol of:

D(−)-α-[(imidazolidin-2-on-1-yl)-carbonylamino]-p-methoxyphenylacetic acid,
L(+)-α-[(imidazolidin-2-on-1-yl)-carbonylamino]-p-methoxyphenylacetic acid,
D,L-α-[(imidazolidin-2-on-1-yl)-carbonylamino]-p-methoxyphenylacetic acid,
D(−)-α-[(imidazolidin-2-on-1-yl)-carbonylamino]-o,o'-dichlorophenylacetic acid,
L(+)-α-[(imidazolidin-2-on-1-yl)-carbonylamino]-o,o'-dichlorophenylacetic acid or
D,L-α-[(imidazolidin-2-on-1-yl)-carbonylamino]-o,o'-dichlorophenylacetic acid, the following penicillins are obtained in the form of their sodium salts:

D(−)-α-[(imidazolidin-2-on-1-yl)-carbonylamino]-p-methoxy-benzylpenicillin,
L(+)-α-[(imidazolidin-2-on-1-yl)-carbonylamino]-p-methoxy-benzylpenicillin,
D,L-α-[(imidazolidin-2-on-1-yl)-carbonylamino]-p-methoxy-benzylpenicillin,
D(−)-α-[(imidazolidin-2-on-1-yl)-carbonylamino]-o,o'-dichlorobenzylpenicillin,
L(+)-α-[(imidazolidin-2-on-1-yl)-carbonylamino]-o,o'-dichlorobenzylpenicillin or
D,L-α-[(imidazolidin-2-on-1-yl)-carbonylamino]-o,o'-dichlorobenzylpenicillin.

Table 7

NMR data of some penicillins of the formula (1).
Position of the signals is indicated in the τ-scale [ppm]. Solvent: CD₃OD.

| Example | NMR signals at [intensity of the signals, deducting the signals of the intermediate acid] | Impurities visible in the spectrum. |
|---|---|---|
| 45 | 2.4–3.0 (4 H), 4.3–4.6 (3 H) 5.8 (1 H), 5.9–6.4 (2 H), 6.4–6.9 (2 H), 7.7 (3 H) and 8.4 (6 H) | 15% by weight of α-(imidazolidin-2-on-1-yl-carbonylamino)-p-methyl-phenylacetic acid |
| 46 | as Example 45 | 60% by weight of α-(imidazolidin-2-on-1-yl-carbonylamino)-p-methyl-phenylacetic acid |
| 47 | 2.6 (4 H), 4.3–4.6 (3 H), 5.8 (1 H), 5.9–6.8 (4 H) and 8.3–8.6 (6 H) | 10% by weight of α-(imidazolidin-2-on-1-yl-carbonylamino)-p-chloro-phenylacetic acid |
| 48A | as Example 47 | 25% by weight of α-(imidazolidin-2-on-1-yl-carbonylamino)-p-chloro-phenylacetic acid |
| 48B acetone-d₆ as the solvent | 0.9 (1 H), 2.6 (2 H), 2.8 (3 H), 4.5 (1 H), 6.2 (2 H), 6.6 (2 H), — and 7.7 (3 H) | |
| 48C acetone-d₆ as the solvent | 0.9 (1 H), 2.55 (4 H), 4.5 (1 H), 6.2 (2 H), and 6.5 (2 H) | — |
| 49 | 2.4–2.75 (5 H), 4.45–4.6 (1 H), 6.0–6.85 (4 H) | — |
| 50 | 2.55–2.8 (4 H), 4.55–4.7 (1 H), 5.95–6.8 (4 H), 7.55 (3 H) | — |
| 51 | 2.35–2.75, 4.35–4.55, 5.75 5.95–6.85, 8.3–8.55 | 58% by weight of D-α-(imidazolidin-2-on-1-yl-carbonyl-amino)-phenyl-acetic acid |
| 52 | (free acid) 2.4–2.7 (5 H), 4.3–4.6 (3 H), 5.55 (1 H), 5.9–6.7 (4 H), 8.25–8.5 (6 H) (Na salt) 2.45–2.75 (5 H), 4.3–4.6 (3 H), 5.8 (1 H), 5.95–6.75 (4 H), 8.3–8.6 (6 H) | — |
| 54 | 2.45–2.9, 4.35–4.6, 5.8, 5.9–6.85, 7.6, 8.3–8.55 | 60% by weight of α-(imidazolidin-2-on-1-yl-carbonyl-amino)-p-methyl-thio-phenylacetic acid |
| 55 | 2.4–2.9, 4.35–4.65, 5.8 5.95–6.8, 7.6, 8.3–8.6 | 40% by weight of α-(imidazolidin-2-on-1-yl-carbonyl-amino)-p-methylthio-phenylacetic acid |

EXAMPLE 59

Sodium D(−)-α-(3-benzoyl-3-methyl-ureido)-benzylpenicillin

D(−)-α-Aminobenzylpenicillin (ampicillin) 15 parts by weight) was suspended in 80% strength aqueous tetrahydrofurane (150 parts by volume) and sufficient triethylamine (approx. 7.5 parts by volume) was added dropwise at 20° C, while stirring, that a clear solution was just produced and the pH value was between 7.5 and 8.2 (glass electrode). The mixture was now cooled to 0° C and a solution of N-benzoyl-N-methylcarbamic acid chloride (6.5 parts by weight) in absolute tetrahydrofurane (25 parts by volume) was added dropwise over the course of 30 minutes, while cooling with ice, the pH value being kept between 7.5 and 8.0 through simultaneous addition of triethylamine. The mixture was stirred for 30 minutes at 0° C and subsequently further stirred at room temperature until addition of triethylamine was no longer necessary for maintaining the pH value of 7.5. Water (150 parts by volume) was now added and the pH value was adjusted to 6.5 with a little dilute surphuric acid, after which the tetrahydrofurane was largely removed in a rotary evaporator at room temperature. The aqueous solution which remained was extracted once by shaking with ether, subsequently covered with a 1:1 mixture of ethyl acetate and ether (400 parts by volume) and treated with sufficient dilute sulphuric acid, while stirring and cooling with ice, to establish a pH value of 1 – 2. The organic phase was separated off, twice washed with water (60 parts by volume at a time) and dried at 0° C over $MgSO_4$ for about one hour, and after filtering, the solution of the penicillin was treated with about 50 parts by volume of a 1 molar solution of sodium 2-ethyl hexanoate in ether containing methanol. The mixture was left to stand at 0° C for some hours, the solvent was subsequently decanted, and the residue was triturated with ether and filtered off. After drying over $P_2O_5$ in a vacuum desiccator, the sodium salt of the penicillin was obtained in the form of a noncrystalline solid.
Yield: 14.7 parts by weight (83%).
β-Lactam content: 87%.
Calculated C 55.4 H 4.8 N 10.3 S 5.9
Found: 56.2 H(7.0) N 9.7 S 5.9 NMR signals at $\tau = 2.4$ (10 H), 4.2 (1 H), 4.4 (2 H), 5.7 (1 H), 6.8 (3 H) and 8.5 ppm (6 H). Effectiveness against E. coli 14: 1.56 units/ml (6.25 units/ml)[x)] Effectiveness against Proteus 3400: 12.5 units/ml (50 units/ml)[x)] Effectiveness against Pseudomonas aerug. Bonn: 12.5 units/ml (25 units/ml[x])

The figures given in brackets give, for comparison, the particular effectiveness of the corresponding penicillin which carries hydrogen in the 3-position in the side chain (that is to say, which is not a subject of the present invention; compare Netherlands Patent No. 69/08909 published Dec. 16, 1969), that is to say sodium D(−)-α-(3-benzoylureido)benzylpenicillin.
Effectiveness in animal experiments: A and B.

EXAMPLE 60

Sodium
D(−)-α-(3-benzoyl-3-ethyl-ureido)-benzylpenicillin

This penicillin was prepared in the manner described in Example 59, from 15 parts by weight of ampicillin and 7.0 parts by weight of N-benzoyl-N-ethylcarbamic acid chloride.
Yield: (crude product): 79%
β-Lactam content: 91%
Calculated: C 53.8 H 5.4 N 9.6 S 5.6 Found: C 53.0 H 5.0 N 9.9 S 5.7.
NMR signals at $\tau = 2.5$ (5 H), 2.6 (5 H), 4.5 (3 H), 5.8 (1 H), 6.2 (2 H), 8.4 (6 H) and 8.8 ppm (3 H).
Effectiveness against E. coli 14: 6.25 units/ml.
Effectiveness against Pseudomonas Aerug. Bonn: 25 units/ml.
Effectiveness in animal experiments: A and B.

EXAMPLE 61

Sodium
D(−)-α-(3-ethoxycarbonyl-3-methyl-ureido)-benzylpenicillin

If 18 parts by weight of ampicillin were reacted with 6.6 parts by weight of N-ethoxycarbonyl-N-methylcarbamic acid chloride in the manner described in Example 59, penicillin was obtained in the form of its Na salt, in 72% yield.
β-Lactam content: 94%
Calculated: C 49.3 H 5.1 N 11.0 S 6.3 Found: C 48.9 H 5.4 N 10.8 S 6.2
NMR signals at $\tau = 2.6$ (5 H), 4.4 (1 H), 4.5 (2 H), 5.8 (3 H), 6.8 (3 H), 8.5 (6 H) and 8.7 ppm (3 H).
Effectiveness against E. coli 14: 3.12 units/ml.
Effectiveness against Pseudomonas Aerug. Bonn: 12.5 units/ml
Effectiveness in animal experiments: A and B.

EXAMPLE 62

Sodium
D(−)-α-(3-hexahydrobenzoyl-3-methyl-ureido-benzyl-penicillin

On reacting 15 parts by weight of ampicillin with 6.7 parts by weight of N-hexahydrobenzoyl-N-methylcarbamic acid chloride in accordance with the instruction of Example 59, the sodium salt of the penicillin was obtained in 60% yield.
β-Lactam content: 89%.
Calculated: C 53.5 H 6.0 N 10.0 S 5.8 Found: C 51.9 H 6.2 N 9.6 S 5.8.
NMR signals at $\tau = 2.6$ (5 H), 4.5 (1 H), 4.55 (2 H), 5.8 (1 H), 6.7 (3 H), 7.3 (1 H), 8.0–9.0 (10 H) and 8.5 ppm (6 H).
Effectiveness against Proteus 3400: 6.25 units/ml.
Effectiveness against Pseudomonas Aerug. Bonn: 12 units/ml.
Effectiveness in animal experiments: A and B.

EXAMPLE 63

Sodium
D(−)-α-(3-cinnamoyl-3-methyl-ureido)-benzylpenicillin

The sodium salt of the penicillin was prepared from 15 parts by weight of ampicillin and 7.4 parts by weight of N-cinnamoyl-N-methylcarbamic acid chloride, as in Example 59.
Yield: 72%
β-Lactam content: 90%
Calculated: C 55.9 H 5.1 N 9.6 S 5.5 Found: C 54.8 H 5.6 N 9.4 S 5.4
NMR signals at $\tau = 2.0$–3.0 (12 H), 4.4 (1 H), 4.5 (1 H), 5.8 (1 H), 6.7 (3 H), 8.4 (3 H) and 8.5 ppm (3 H).
Effectiveness against E. coli 14: <0.78 units/ml.
Effectiveness against Proteus 1017: 1.56 units/ml.
Effectiveness against Pseudomonas Aerug. Bonn: 6.25 units/ml.
Effectiveness in animal experiments: A and B.

EXAMPLE 64

Sodium
D(−)-α-(3-β-chloropropionyl-3-methyl-ureido)-benzylpenicillin 19.7 parts by weight of ampicillin were reacted with 7.0 parts by weight of N-β-chloropropionyl-N-methylcarbamic acid chloride in accordance with Example 59.
Yield: 80%
β-Lactam content: 94%
Calculated C 47l8 H 4.8 Cl 6.7 N. 10.6 S 6.1 Found: C 48.4 H 5.5 Cl 6.0 N 10.5 S 6.5:
NMR signals at $\tau = 2.6$ (5 H), 4.4 (1 H), 4.5 (2 H), 5.8 (1 H), 6.2 (2 H), 6.8 (3 H 6.9 (2 H) and 8.5 ppm (6 H)
Effectiveness against E. coli 14: 3.12 units/ml.
Effectiveness against Proteus 1017: 25 units/ml.

EXAMPLE 65

Sodium D(−)-α-(3-(1,2,5,6)-tetrahydrobenzoyl-3-methyl-ureido)benzylpenicillin

This penicillin was prepared in the manner described in Example 59, from 15.8 parts by weight of ampicillin and 7.0 parts by weight of N-1,2,5,6-tetrahydrobenzoyl-N-methyl-carbamic acid chloride.
Yield: 55%
β-Lactam content: 85% (according to the IR spectrum)
Calculated: C 55.2 H 5.6 N 10.3 S 5.9 Found: C 54.5 H 6.3 N 10.2 S 5.9
NMR signals at $\tau$ = 2.3–2.8 (5 H), 4.2–4.6 (5 H), 5.8 (1 H) 6.7 (3 H), 7.1 (1 H) and 7.6–8.8 ppm (12 H)
Effectiveness against *E. coli* 14: <0.78 units/ml.
Effectiveness against *Proteus* 1017: 3.12 units/ml.
Effectiveness against *Pseudomonas Aerug.* Bonn: 12.5 units/ml.
Effectiveness in animal experiments: A and B.

EXAMPLE 66A

Sodium D(−)-α-(3-acetyl-3-methyl-ureido)-benzylpenicillin

This penicillin was prepared in the manner described in Example 59, from 20 parts by weight of ampicillin and 6.0 parts by weight of N-acetyl-N-methyl-carbamic acid chloride.
Yield: 100%
β-Lactam content: 86%
Calculated: C 49.2 H 5.1 N 11.5 S 6.5 Found: C 49.2 H(7.0) N 10.4 S 6.5
NMR signals at $\tau$ = 2.6 (5 H), 4.45 (1 H), 4.55 (2 H), 5.8 (1 H), 6.75 (3 H), 7.7 (3 H) and 8.5 ppm (6 H).
Effectiveness against *E. coli* 14: 3.12 units/ml.
Effectiveness against *Pseudomonas Aerug.* Bonn: 6.25 units/ml.
Effectiveness against *Klebsiella* K 10: 50 units/ml.
Effectiveness in animal experiments: A and B.

EXAMPLE 66B

Crystalline sodium D(−)-α-(3-acetyl-3-methyl-ureido)-benzylpenicillin

The process of preparing sodium D(−)-α-(3-acetyl-3-methylureido)-benzylpenicillin, following Example 59, yields an amorphous product, as is shown by an X-ray diffraction picture. If this substance (3.8 parts by weight) is dissolved in ethanol (15 parts by volume) at room temperature (duration of the solution process approximately 15 to 20 minutes), acetic acid ethyl ester (60 parts by volume) is substantially added, and the clear colorless solution is left to stand at room temperature, very fine hair-like crystals (bundles of needles), which are recognizable as such with the naked eye, begin to separate out after 1 to 2 hours, if crystal seeds are not yet present. After some hours the crystals are filtered off, washed with acetic acid ethyl ester and dried thoroughly in a chamber wherein drying is effected by circulating air at 60° C.
Yield: 3.0 parts by weight
β-Lactam content: 92%
Melting point: about 212° C (corrected, decomposition) (Kofler bench)
NMR signals at $\tau$ = 2.5 (5 H), 4.4 (1 H), 4.55 (2 H), 5.8 (1 H), 6.7 (3 H), 7.7 (3 H) and 8.5 ppm (6 H)

Calculated: (1.9% $H_2O$ content C 50.1 H 5.0 N 11.7 S 6.7 (taken into account) Found: C 50.1 H 5.8 N 10.8 S 7.0

The IR spectra of the amorphous and crystalline penicillin salt are depicted in FIGS. 1 and 2.

It is however also possible to suspend the amorphous penicillin salt in acetic acid ethyl ester and then to add about 20% of ethanol while stirring. In that case, also, a clear solution is produced, from which the crystalline penicillin salt separates out.

It is furthermore also possible to use other solvent mixtures, for example ethanol/dioxane. If the amorphous salt is dissolved in acetone or warm (approx. 50° C) isopropanol and left to stand, the salt again separates out in a crystalline form.

EXAMPLE 67

Sodium D(−)-α-(3-cyclohexyloxycarbonyl-3-methyl-ureido)-benzylpenicillin

This penicillin was obtained from 20 parts by weight of ampicillin and 12 parts by weight of N-cyclohexyloxycarbonyl-N-methylcarbamic acid chloride, in the manner described in Example 59.
Yield: 49%; β-Lactam content: 94%
Calculated: C 53.2 H 5.7 N. 9.9 S 5.7 Found: C 53.1 H 6.5 N 9.7 S 5.5
NMR signals at $\tau$ = 2.6 (5 H), 4.4 (1 H), 4.5 (2 H), 5.2 (1 H) 5.8 (1 H), 6.0 (3 H) and 7.9–8.9 (16 H)
Effectiveness against *E. coli* 14: 1.56 units/ml.
Effectiveness against Proteus 3400:6.25 units/ml.
Effectiveness against *Pseudonomas Aerug.* Bonn: 25 units/ml.
Effectiveness in animal experiments: A and B.

EXAMPLE 68

Sodium D(−)-α-(3-allyloxycarbonyl-3-methyl-ureido)-benzylpenicillin

This penicillin was prepared from 19.2 parts by weight of ampicillin and 7.5 parts by weight of N-allyloxuycarbonyl-N-methyl-carbamic acid chloride in the manner described in Example 59.
Yield: 79%
β-Lactam content: 90%
Calculated: C 50.9 H 5.0 N 10.7 S 6.2 Found: C (53.8) H 5.8 N 10.7 S 6.2
NMR signals at $\tau$ = 2.6 (5 H), 3.7–4.3 (1 H), 4.4 (1 H), 4.4–4.9 (4 H), 5.2 (2 H), 5.8 (1 H), 6.8 (3 H) and 8.4 ppm (6 H).
Effectiveness against *Pseudomonas Aerug.* Bonn: 12.5 units/ml.
Effectiveness in animal experiments: A and B.

EXAMPLE 69

Sodium D(−)-α-(3-γ-trifluorobutyryl-3-methylureido)-benzylpenicillin

This penicillin was obtained in the manner described in Example 59, on reacting 16.7 parts by weight of ampicillin with 8.0 parts by weight of N-γ-trifluorobutyryl-N-methylcarbamic acid chloride.
Yield: 80%
β-Lactam content: 91%
Calculated: C 47.1 H 4.5 N 9.9 S 5.7 Found: C 46.6 H 4.9 N 9.6 S 5.8

NMR signals at τ = 2.6 (5 H), 4.4 (1 H), 4.55 (20 H), 5.8 (1 H), 6.9–7.8 (4 H), and 8.5 ppm (6 H).
Effectiveness against *E. coli* 14: 1.56 units/ml.
Effectiveness against *Proteus* 1017: 12.5 units/ml.
Effectiveness against *Pseudomonas Aerug.* Bonn: 12.5 units/ml.
Effectiveness against *Klebsiella* 63: 12.5 units/ml.
Effectiveness in animal experiments: A and B.

EXAMPLE 70

Sodium
D(−)-α-(3-[m-nitro-p-methyl]-benzoyl-3-methyl-ureido)benzylpenicillin:

This penicillin was obtaned in the manner described in Example 59, on reacting 15 parts by weight of ampicillin with 8.5 parts by weight of N-m-nitro-p-methyl-benzoyl-N-methylcarbamic acid chloride.
Yield: 64%
β-Lactam content: 88%
Calculated: C 50.7 H 4.7 N 11.3 S 5.2 Found: C 50.6 H 5.7 N 11.2 S. 50
NMR signals at τ = 1.9 (1 H), 2.2–2.4 (1 H), 2.4–2.6 (6 H), 4.4 (1 H), 4.5 (2 H), 5.8 (1 H), 6.8 (3 H), 7.4 (3 HI and 8.5 ppm (6 H).
Effectiveness against *Pseudomonas aerug.* Bonn: 12.5 units/ml.
Effectiveness against *Klebsiella* 63: 12.5 units/ml.
Effectiveness in animal experiments: A and B.

EXAMPLE 71

Sodium D
(−)-α-(3-sterinoyl-3-methyl-ureido)-benzylpenicillin

This penicillin was prepared from 15 parts by weight of ampicillin and 11.9 parts by weight of N-sterinoyl-N-methyl-carbamic acid chloride in the manner described in Example 59.
Yield: 80%
β-Lactam content: 80%
Calculated: C 61.4 H 8.0 S 4.5 Found: C 61.0 H 8.4 N 7.5 S 4.3
NMR signals at τ = 2.6 (5 H), 4.4 (1 H), 4.5 (2 H), 5.8 (1 H), 6.8 (3 H, 7.4 (2 (2H) and 8.3–9.3 ppm (39 H).

EXAMPLE 72

Sodium
D(−)-α-(3-γ-trichlorobutyryl-3-β-chloroethyl-ureido)-benzylpenicillin

This penicillin was prepared from 15 parts by weight of ampicillin and 10.4 parts by weight of N-γ-trichlorobutyryl-N-β-chloroethyl-carbamic acid chloride in the manner described in Example 59.
Yield: 56%
β-Lactam content: 91%
Calculated: C 41.9 H 4.0 Cl 2.15 n 8.5 S 4.8 C 43.2 H 5.1 Cl 20.0 N 8.5 S 4.7
Effectiveness against *E. coli* 14: 6.25 units/ml.
Effectiveness against *Klebsiella* 63: 50 units/ml.
Effectiveness in animal experiments: A and B.

EXAMPLE 73

Sodium
D(−)-α-(3-p-methylbenzoyl-3-methyl-ureido)-benzylpenicillin

This penicillin was prepared from 18 parts by weight of ampicillin and 11 parts by weight of N-P-methyl-benzoyl-N-methyl-carbamic acid chloride in the manner described in Example 59.
Yield: 79%
β-Lactam content: 89% Calculated: $C_{55.4}$ H 5.2 N 9.9 S 5.7 Found: C 54.6 H 6.7 N 9.9 S 5.8 NMR signals at τ = 2.3–2.9 (9 H), 4.35 (1 H), 4.5 (2 H), 5.8 (1 H), 6.85 (3 H), 7.65 (3 H) and 8.45 (6 H). Effectiveness against *E. coli:* 312 units/ml. Effectiveness against *Proteus* 1017: 6.25 units/ml. Effectiveness against Klebsiella 63: 12.5–25 units/ml. Effectiveness in animal experiments: A and B.

EXAMPLE 74

Sodium
D(−)-α-(3-acetyl-3-hexadecyl-ureido)-benzylpenicillin:

This penicillin was prepared from 15 parts by weight of ampicillin and 11.4 parts by weight of N-acetyl-N-hexadecylcarbamic acid chloride in the manner described in Example 59. Yield: 56% β-Lactam content: 76% Calculated: C 60.7 H 7.9 N 8.1 S 4.6 Found: C 60.3 H 8.0 N 5.76 S 4.9
NMR signals at τ = 2.6 (5 H), 4.4 (1 H), 4.55 (2 H), 5.8 (1 HI, 6.3 (2 H), 7.7 (3 H), 8. 45 (6 H), 8.7 (28 H), and 9.1 ppm (3 H),

EXAMPLE 75

Sodium
D(−)-α-(3-thenoyl-(2)-3-methyl-ureido)-benzylpenicillin

This penicillin was obtained in 81% yield on reacting 18.1 parts by weight of amplication with 8.2 parts by weight of N-2-thenoyl-N-methyl carbamic acid chloride. (See Example 59). β-Lactam content: 92% Calculated: C 50.8 H 4.4 N 10.3 S 11.8 Found: C 51.7 H 6.1 N 9.9 S 11.9
NMR signals at τ = 2.1–3.0 (8H), 4.4 (1H), 4.5 (1 H), 4.6 (1)H, 5.8 (1 H), 6.6 (3 H) and 8.5 ppm (6 H).
Effectiveness in animal experiments: A and B.

EXAMPLE 76

Sodium
D(−)-α-[3,5-dimethylisoxazol-4-yl]-carbonyl-3-methyl-ureido)-benzylpenicillin This was prepared from 18.1 parts by weight of ampicillin and 8.7 parts by weight of N-4-(3,5-dimethyl)-isoxazolyl-carbonyl-N-methyl-carbamic acid chloride. (See Example 59).
Yield: 70% β-Lactam content: 85%
Calculated: C 51.7 H 4.9 N 12.5 S 5.7 Found: C 50.6 H 6.2 N 11.1 S 5.5
NMR signals at τ = 2.6 (5 H), 4.4 (1 H), 4.5 (H), 4.6 (1 H), 5.8 (1 H), 6.8 (3 H), 7.6 (3 H), 7.75 (3 H), 8.4 (3 H) and 8.5 ppm (3 H).
Effectiveness in animal experiments: A and B.

EXAMPLE 77

If, in the procedure of Examples 59 and 64, the D-α-aminoamino-benzylpenicillin used there is replaced by 0.04 mol of:
α-amino-p-methylbenzylpenicillin,
α-amino-p-chlorobenzylpenicillin,
α-amino-p-methylthiobenzylpenicillin,
α-amino-p-methoxybenzylpenicillin,
α-amino-o-chlorobenzylpenicillin,
α-amino-m-iodobenzylpenicillin, α-amino-2,6-dichlorobenzylpenicillin,
α-amino-2,6-dimethoxybenzylpenicillin,
α-amino-2,4-dibromobenzylpenicillin,
α-amino-m-methylbenzylpenicillin,
α-amino-2,6-dimethylbenzylpenicillin,
α-amino-2-chloro-6-fluorobenzylpenicillin,
α-amino-α-2-thienylmethylpenicillin or
α-amino-α-3-thienylmethylpenicillin;
the following penicillins are obtained:
sodium α-(3-benzoyl-3-methyl-ureido)-p-methylbenzylpenicillin,
sodium α-(3-benzoyl-3-methyl-ureido)-p-chlorobenzylpenicillin,
sodium α-(3-benzoyl-3-methyl-ureido)-p-methylthiobenzylpenicillin,
sodium α-(3-benzoyl-3-methyl-ureido)-p-methoxybenzylpenicillin,
sodium α-(3-benzoyl-3-methyl-ureido)-o-chlorobenzylpenicillin,
sodium α-(3-benzoyl-3-methyl-ureido)-m-iodobenzylpenicillin,
sodium α-(3-benzoyl-3-methyl-ureido)-2,6-dichlorobenzylpenicillin,
sodium α-(3-benzoyl-3-methyl-ureido)-2,6-dimethoxybenzylpenicillin,
sodium α-(3-benzoyl-3-methyl-ureido)-2,4-dibromobenzylpenicillin,
sodium α-(3-benzoyl-3-methyl-ureido)-α-3-thienylmethylpencicillin,
sodium α-(3-benzoyl-3-methyl-ureido)-m-methylbenzylpenicillin,
sodium α-(3-benzoyl-3-methyl-ureido)-2,6-dimethylbenzylpenicillin,
sodium α-(3-benzoyl-3-methyl-ureido)-2-chloro-6-fluorobenzylpenicillin,
sodium α-(3-benzoyl-3-methyl-ureido)-α-2-thienylmethylpenicillin,
sodium α-(3-acetyl-3-methyl-ureido)-p-methylbenzylpenicillin,
sodium α-(3-acetyl-3-methyl-ureido)-p-chlorobenzylpenicillin,
sodium α-(3-acetyl-3-methyl-ureido)-p-methylthiobenzylpenicillin,
sodium α-(3-acetyl-3-methyl-ureido)-p-methoxybenzylpenicillin,
sodium α-(3-acetyl-3-methyl-ureido)-o-chlorobenzylpenicillin,
sodium α-(3-acetyl-3-methyl-ureido)-m-iodobenzylpenicillin,
sodium α-(3-acetyl-3-methyl-ureido)-2,6-dichlorobenzylpenicillin,
sodium α-(3-acetyl-3-methyl-ureido)-2,6-dimethoxybenzylpenicillin,
sodium α-(3-acetyl-3-methyl-ureido)-2,4-dibromobenzylpenicillin,
sodium α-(3-acetyl-3-methyl-ureido)-m-methylbenzylpenicillin,
sodium α-(3-acetyl-3-methyl-ureido)-2,6-dimethylbenzylpenicillin,
sodium α-(3-acetyl-3-methyl-ureido)-2-chloro-6-fluorobenzylpenicillin,
sodium α-(3-acetyl-3-methyl-ureido)-α-2-thienylmethylpenicillin or
sodium α-(3-acetyl-3-methyl-ureido)-α-3-thienylmethylpenicillin.

EXAMPLE 78

If, in the procedure of Example 59, the N-benzoyl-N-methylcarbamic acid chloride used there is replaced by 0.035 mol of:
N-acetyl-N-ethyl-carbamic acid chloride,
N-acetyl-N-vinyl-carbamic acid chloride,
N-acetyl-N-n-propyl-carbamic acid chloride,
N-acetyl-N-propenyl-carbamic acid chloride,
N-acetyl-N-i-propyl-carbamic acid chloride,
N-acetyl-N-n-butyl-carbamic acid chloride,
N-acetyl-N-t-butyl-carbamic acid chloride,
N-acetyl-N-β-methoxyethyl-carbamic acid chloride,
N-acetyl-N-β-dimethylaminoethyl-carbamic acid chloride,
N-acetyl-N-cyclohexyl-carbamic acid chloride,
N-acetyl-N-cyclobutyl-carbamic acid chloride,
N-methoxyacetyl-N-methyl-carbamic acid chloride,
N-propionyl-N-methyl-carbamic acid chloride,
N-methyl-sulphenylacetyl-N-methyl-carbamic acid chloride,
N-propionyl-N-ethyl-carbamic acid chloride,
N-propionyl-N-vinyl-carbamic acid chloride,
N-n-butyryl-N-methyl-carbamic acid chloride,
N-methoxycarbonyl-acetyl-N-methyl-carbamic acid chloride,
N-i-butyryl-N-methyl-carbamic acid chloride,
N-acryloyl-N-methyl-carbamic acid chloride,
N-pivaloyl-N-methyl-carbamic acid chloride,
N-cyanomethyl-acetyl-N-methyl-carbamic acid chloride,
N-acetyl-N-phenyl-carbamic acid chloride or
N-propionyl-N-phenyl-carbamic acid chloride; the following penicillins are obtained:
sodium D(−)-α-(3-acetyl-3-ethyl-ureido)-benzylpenicillin,
sodium D(−)-α-(3-acetyl-3-vinyl-ureido)-benzylpenicillin,
sodium D(−)-α-(3-acetyl-3-n-propyl-ureido)-benzylpenicillin,
sodium D(−)-α-(3-acetyl-3-propenyl-ureido)-benzylpenicillin,
sodium D(−)-α-(3-acetyl-3-i-propyl-ureido)-benzylpenicillin,
sodium D(−)-α-(3-acetyl-3-n-butyl-ureido)-benzylpenicillin,
sodium D(−)-α-(3-acetyl-3-t-butyl-ureido)-benzylpenicillin,
sodium D(−)-α-(3-acetyl-3-β-methoxyethyl-ureido)-benzylpenicillin,
sodium D(−)-α-(3-acetyl-3-β-dimethyl-aminoethyl-ureido)-benzylpenicillin,
sodium D(−)-α-(3-acetyl-3-cyclohexyl-ureido)-benzylpenicillin,
sodium D(−)-α-(3-acetyl-3-cyclobutyl-ureido)-benzylpenicillin,
sodium D(−)-α-(3-methoxyacetyl-3-methyl-ureido)-benzylpenicillin,
sodium D(−)-α-(3-propionyl-3-methyl-ureido)-benzylpenicillin,
sodium D(−)-α-(3-methylthio-acetyl-3-methyl-ureido)-benzylpenicillin,
sodium D(−)-α-(3-propionyl-3-ethyl-ureido)-benzylpenicillin,
sodium D(−)-α-(3-propionyl-3-vinyl-ureido)-benzylpenicillin,
sodium D(−)-α-(3-n-butyryl-3-methyl-ureido)-benzylpenicillin, sodium D(−)-α-(3-methoxycarbonyl-acetyl-3-methyl-ureido)-benzylpenicillin, sodium D(−)-α-(3-i-butyryl-3-methyl-ureido)-benzylpenicillin, sodium D(−)-α-(3-acryloyl-3-methyl-ureido)-benzylpenicillin, sodium D(−)-α-(3-pivaloyl-3-methyl-ureido)-benzylpenicillin, sodium D(−)-α-(3-cyano-methyl-acetyl-3-methyl-ureido)-benzylpenicillin, sodium D(−)-α-(3-acetyl-3-phenyl-ureido)-benzylpenicillin or sodium D(−)-α-(3-propionyl-3-phenyl-ureido)-benzylpenicillin.

EXAMPLE 79

Sodium D(−)-α-(3-benzoyl-3-methyl-ureido)-benzylpenicillin

A solution of 10.6 parts by weight of bix-trimethylsilylampicillin in 50 parts by volume of dry methylene chloride was cooled to −10° C with exclusion of moisture, and treated with a solution of 3.8 parts by weight of N-benzoyl-N-methyl-carbamic acid chloride in 20 parts by volume of absolute methylene chloride, cooled to 0° C. The mixture was left to stand in a refrigerator for 6 hours, the solvent was then stripped off in a rotary evaporator at room temperature, the residue was taken up in 100 parts by volume of a 1:1 mixture of ether and ethyl acetate, and the solution was exhaustively extracted with 2N sodium bicarbonate solution. The aqueous phase was treated with fresh ether-ethyl acetate mixture and acidified with 2 N HCl to pH = 1.5–2.0 (glass electrode), while cooling with ice; the organic phase was separated off, again washed with water and subsequently dried over $Na_2SO_4$ at 0° C, and the sodium salt of the penicillin was precipitated, and isolated, in the manner described in Example 59.

Yield: 56%

β-Lactam content: 74%

Calculated: C 54.1 H 5.0 N 10.1 S 5.8

Found: C 54.0 H 5.6 N 9.5 S 5.7 The IR and NMR spectra are identical with those of the penicillin from Example 1.

EXAMPLE 80

Sodium D(−)-α-(3-benzoyl-3-methyl-ureido)-benzylpenicillin 15 parts by weight of ampicillin were suspended in 150 parts by volume of 80% strength aqueous tetrahydrofurane and sufficient dilute HCl was subsequently added, whilst cooling to −5° C, to establish a pH value of 2.5 and partially to dissolve the ampicillin. A solution of 6.5 parts by weight of N-benzoyl-N-methyl-carbamic acid chloride in 25 parts by weight of absolute tetrahydrofurane was now added dropwise over the course of 30 minutes, at −5° C, while keeping the pH value at 2.5–3.0 by simultaneous addition of triethylamine. The mixture was stirred for a further 20 minutes until the pH value remained constant at about 3.0 even without the addition of triethylamine. A pH value of 6.5–7.0 was now established by means of triethylamine, 150 parts by volume of water are added, and the tetrahydrofurane was evaporated off in a rotary evaporator at room temperature. The aqueous solution was once extracted with 100 parts by volume of ether, then covered with 200 parts by volume of a 1:1 mixture of ether and ethyl acetate, and brought to pH = 1.5–2.0 by adding 2 N hydrochloric acid whilst cooling with ice, and the penicillin was removed from the water by repeated extraction with ether-ethyl acetate mixture. The combined organic phases were twice washed with 100 parts by volume of water at a time and dried over $MgSO_4$, and the sodium slat of the penicillin was subsequently precipitated and isolated in the manner described in Example 59.

Yield: 60%

β-Lactam content: 93.3%.

Calculated: C 54.9 H 4.9 N 10.2 S 5.8

Found: C 54.7 H 5.4 N 10.1 S 5.9 The product agrees with that of Example 1 in respect of its IR and NMR spectra.

EXAMPLE 81

Sodium D(−)-α-(3-γ-trichlorobutyryl-3-β-chloroethyl-ureido)-benzylpenicillin

A mixture of 8.0 parts by weight of ampicillin, 100 parts by volume of methylene chloride and 5.5 parts by volume of triethylamine was stirred for 2 hours at room temperature, and then stirred vigorously, for a further 15 minutes, with anhydrous sodium sulphate and filtered. The mixture was cooled to 0° C and a solution of 6.3 parts by weight of N-γ-trichlorobutyryl-N-β-chloroethyl-carbamic acid chloride in 30 parts by volume of dry methylene chloride was added dropwise over the course of 20 minutes, while excluding moisture. Thereafter the mixture was stirred for a further 90 minutes at 0° C and then concentrated to dryness in a rotary evaporator, in vacuo. The residue was taken up in water, the pH value was adjusted to 7–8 with 2 N NaOH, and the mixture was extracted once with ether. Thereafter working up took place as in Example 59 under acid conditions, and the sodium salt of the penicillin was precipitated and isolated.

Yield: 49%

β-Lactam content: 81% The product agrees with that of Example 14 as regards its IR abd NMR spectrum.

EXAMPLE 82

Calcium L(+)-α-(3-benzoyl-3-methyl-ureido)-benzylpenicillin

This penicillin was prepared as described in Example 59, but instead of the D-α-aminobenzylpenicillin used in Example 59, 0.35 part by weight of L-α-amino-benzylpenicillin was reacted with 0.15 part by weight of N-benzoyl-N-methyl-carbamic acid chloride. The penicillin was isolated as the calcium salt.

Yield: 5%

β-Lactam content: 75% NMR signals at τ= 2.4–2.8 (10 H), 4.35–4.65 (3 H), 5.8 (1 H), 6.85 (3 H) and 8.4 ppm (6 H).

EXAMPLE 83

Sodium D(−)-α-(3-[4-methoxy-3-nitrobenzoyl]-3-methyl-ureido)-benzylpenicillin

Sufficient 2 N NaOH was added to a suspension of 17.5 parts by weight of ampicillin in 250 parts by volume of 80% strength aqueous tetrahydrofurane, at 0° C, for solution just to occur. A solution of 13.6 parts by weight of N-(4-methoxy-3-nitrobenzoyl)-carbamic acid chloride in 30 parts by volume of absolute tetrahydrofurane as now added dropwise over the course of 30 minutes, and the pH value was simultaneously kept between 7.5 and 8.0 by adding 2 N sodium hydroxide solution. The mixture was stirred for a further 30 minutes at 0° C and sufficiently long (~60 minutes) at room temperature for the pH value to remain at 7–8 even without addition of sodium hydroxide solution. The tetrahydrofurane was now removed in a rotary evaporator, at room temperature, 100 parts by volume of water were added and the mixture was extracted with 100 parts by volume of ether. The aqueous phase was covered with 200 parts by volume of a 1:1 mixture of ether and ethyl acetate after which it was acidified to pH = 2 with dilute hydrochloric acid, while stirring and cooling with ice, and was then extracted twice with 100 parts by volume, at a time, of ether-ethyl acetate mixture. The combined organic phases were washed with 2 × 50 parts by volume of water and dried over anhydrous $MgSO_4$, the drying agent was filtered off, and the filtrate was treated with 50 parts by volume of a molar solution of sodium 2-ethylhexanoate in ether containing methanol. Thereafter, the solvent was almost completely removed in vacuo at room temperature, the residue was taken up in methanol, and the sodium salt of the penicillin was precipitated by adding ether. After standing for 30 minutes at 0° C, the supernatant solvent was decanted, and the residue was suspended in ether, filtered and dried over $P_2O_5$ in a vacuum desiccator.

Yield: 88%

β-Lactam content: 72%

Calculated: C 51.3 H 4.3 N 11.5 S 5.3
Found: C 51.5 H 5.7 N 10.7 S 5.1.

NMR signals at $\tau$ = 1.9 (1 H) 2.2 (1 H), 2.6 (5 H), 2.7 (1 H), 4.4 (1 H), 4.5 (2 H), 5.8 (1 H), 6.0 (3 H), 6.7 (3 H) and 8.45 ppm (6 H).

Effectiveness against *E. coli* 14: 3.12 units/ml.
Effectiveness against *Propteus* 3400: 6.25 units/ml.
Effectiveness in animal experiments: A and B.

EXAMPLE 84

If, in the procedure of Example 83, the ampicillin used there is replaced by 0.05 mol of:
α-amino-p-methylbenzylpenicillin,
α-amino-p-chlorobenzylpenicillin,
α-amino-p-methoxybenzylpenicillin,
α-amino-p-methylsulphenylbenzylpenicillin,
α-amino-o-chlorobenzylpenicillin,
α-amino-m-iodobenzylpenicillin or
α-amino-m-methylbenzylpenicillin;
the following penicillins are obtained:
sodium α-(3-[3-nitro-4-methoxybenzoyl]-3-methyl-ureido)-p-methyl-benzylpenicillin,
sodium a-(3-[3-nitro-4-methoxybenzoyl]-3-methyl-ureido)-p-chloro-benzylpenicillin,
sodium a-(3-[3-nitro-4-methoxybenzoyl]-3-methyl-ureido)-p-methoxybenzylpenicillin,
sodium α-(3-[3-nitro-4-methoxybenzoyl]-3-methyl-ureido)-p-methyl-thiobenzylpenicillin,
sodium α-(3-[3-nitro-4-methoxybenzoyl]-3-methyl-ureido)-o-chloro-benzylpenicillin,
sodium α-(3-[3-nitro-4-methoxybenzoyl]-3-methyl-ureido)-m-iodo-benzylpenicillin or
sodium α(3-[3-nitro-4-methoxybenzoyl]-3-methyl-ureido)-m-methyl-benzylpenicillin.

EXAMPLE 85

If, in the procedure according to Example 83, the N-(3-nitro-4-methoxybenzoyl)-N-methyl-carbamic acid chloride used there is replaced by 0.05 mol of:
N-(p-methoxybenzoyl)-N-methyl-carbamic acid chloride,
N-(p-methoxycarbonylaminobenzoyl)-N-methyl-carbamic acid chloride,
N-(p-chlorobenzoyl)-N-ethyl-carbamic acid chloride,
N-(o-bromobenzoyl)-N-(n-propyl)-carbamic acid chloride,
N-(p-ethoxybenzoyl)-N-(i-propyl)-carbamic acid chloride,
N-(m-chlorobenzoyl)-N-allyl-carbamic acid chloride,
N-(2-chloro-5-methoxy-benzoyl)-N-(n-butyl)-carbamic acid chloride,
N-(p-methylthiobenzoyl)-N-methyl-carbamic acid chloride,
N-(p-nitrobenzoyl)-N-methyl-carbamic acid chloride,
N-(2,4-dichlorobenzoyl)-N-methyl-carbamic acid chloride,
N-(2-chloro-4-methoxybenzoyl)-N-methyl carbamic acid chloride,
N-(2-chloro-4-ethylthiobenzoyl)-N-methyl-carbamic acid chloride,
N-(3-chloro-4-methoxybenzoyl)-N-methyl-carbamic acid chloride,
N-(m-cyanobenzoyl)-N-methyl-carbamic acid chloride,
N-(3,5-dimethylbenzoyl)-N-methyl-carbamic acid chloride,
N-(m-iodobenzoyl)-N-methyl-carbamic acid chloride or
N-(1-naphthoyl)-N-methyl-carbamic acid chloride;
the sodium salts of the following penicillins are obtained:
D(−)-α-(3-p-methoxybenzoyl-3-methyl-ureido)-benzylpenicillin,
D(−)-α-(3-p-methoxycarbonylaminobezoyl)-3-methyl-ureido)-benzylpenicillin,
D(−)-α-(3-p-chlorobenzoyl-3-ethyl-ureido)-benzylpenicillin,
D(−)-α-(3-o-bromobenzoyl-3-n-propyl-ureido)-benzylpenicillin,
D(−)-α-(3-ethoxybenzoyl-3-i-propyl-ureido)-benzylpenicillin,
D(−)-α-(3-m-chlorobenzoyl-3-allyl-ureido)-benzylpenicillin,
D(−)-α-(3-[2-chloro-5-methoxybenzoyl]-3-n-butyl-ureido)-benzylpencillin,
D(−)-α-(3-p-methylthiobenzoyl-3-methyl-ureido)-benzylpenicillin,
D(−)-α-(3-p-nitrobenzoyl-3-methyl-ureido)-benzylpenicillin,
D(−)-α-(3-[2,4-dichlorobenzoyl]-3-methyl-ureido)-benzylpenicillin,
D(−)-α-(3-[2-chloro-4-methoxybenzoyl]-3-methyl-ureido)-benzylpenicillin,
D(−)-α-(3-[2-chloro-4-ethylthiobenzoyl]-3-methyl-ureido)-benzylpenicillin,
D(−)-α-(3-[3-chloro-4-methoxybenzoyl]-3-methyl-ureido)-benzyl-penicillin,
D(−)-α-(3-m-cyanobenzoyl-3-methyl-ureido)-benzylpenicillin,
D(−)-α(3-[3,5-dimethylbenzoyl]-3-methyl-ureido)-benzylpenicillin,
D(−)-α-(3-m-iodobenzoyl-3-methyl-ureido)-benzylpenicillin, or D(—)-α-(3[i-naphthoyl]-3-methyl-ureido)-benzyl-penicillin.

EXAMPLE 86

Sodium
D(—)-α-(3-acetyl-3-allyl-ureido)-benzylpenicillin

This penicillin was prepared in the manner described in Example 83, by reacting 17.5 parts by weight of ampicillin with 8.1 parts by weight of N-acetyl-N-allyl-carbamic acid chloride.
Yield: 81%
β-Lactam content: 82%
Calculated: C 51.2H 5.3 N 10.8S 6.2
Found: C 51.9 H(6.9) N 10.5S 6.4.
NMR signals at $\tau$= 2.4–2.8 (5 H), 4.5–5.2 (6 H), 5.6 (2 H), 5.85 (1 H), 7.7 (3 H) and 8.5 ppm (6 H).
Effectiveness against *E. coli* 14: 12.5 units /ml.
Effectiveness against *Pseudomonas Aerug. Bonn:* 25 units/ml.
Effectiveness in animal experiments: A and B.

EXAMPLE 87

Sodium
D(—)-α-(3-acetyl-3-allyl-ureido)-benzylpenicillin

This penicillin was prepared from 17.5 parts by weight of ampicillin and 10.6 parts by weight of N-acetyl-N-benzyl carbamic acid chloride, in the manner described in Example 83.
Yield: 85%
β-Lactam content: 70%
Calculated: C 54.4H 5.3N 9.77S 5.7
Found: C 54.4H 5.7 N 9.77 S 5.6.
NMR signals at $\tau$ = 2.3–3.0 (10 H), 4.4 (1H), 4.5 (2 H), 5.0 (2 H), 5.8 (1 H), 7.8 (3 H) and 8.5 ppm (6 H).
Effectiveness in animal experiments: A and B.

EXAMPLE 88

Sodium
D(—)-α-(3γ-chlorobutyryl-3-methyl-ureido)-benzyl-penicillin

This penicillin was prepared from 17.5 parts by weight of ampicillin and 9.9 parts by weight of N-γ-chlorobutyryl-n-methylcarbamic acid chloride, in the manner described in Example 83.
Yield: 91%
β-Lactam content: 67%
Calculated: C 49.6 H 4.9 Cl 6.6 N 10.5 S 6.0
Found: C 49.8 H 6.1 Cl 6.1 N 10.3 S 6.5.
NMR signals at $\tau$= 2.3–2.9 (5 h), 4.45 (1 H), 4.55 (2 H), 5.8 (1H), 6.4 (2H), 6.75 (3H), 7.3 (2 H), 7.9 (2H) and 8.5 ppm (6H).
Effectiveness in animal experiments: A and B.

EXAMPLE 89

Sodium
D(—)-α-(3γ-trichlorobutyryl-3-methyl-ureido)-benzyl-penicillin

This penicillin was prepared from 17.5 parts by weight of ampicillin and 13.4 parts by weight of N-γ-trichlorobutyryN-methyl-carbamic acid chloride, in the manner described in Example 83.
Yield: 77%
β-Lactam content: 66.5%
Calculated: C 43.9 H 4.0 Cl 17.7N 9.3 S 5.3
Found: C 44.5 H 5.6Cl 15.4 N 8.2 S 5.3 NMR signals at $\tau$= 2.3–2.8 (5H), 4.4 (1 H), 4.55 (2 H), 5.8 (1H), 6.7 (4 H), 6.9 (3H) and 8.45 ppm (6 H).
Effectiveness in animal experiments: A and B.

EXAMPLE 90

Sodium
D(—)-α-(3-benzoyl-3-allyl-ureido)-benzylpenicillin

This penicillin was prepared from 17.5 parts by weight of ampicillin and 11.2 parts by weight of N-benzoyl-N-allylcarbamic acid chloride, in the manner described in Example 83.
Yield: 75%
β-Lactam content: 90%
Calculated: C 56.0 H 4.8 N 10.9 S 5.7 Found:C 56.1 H 5.6 N 9.7 S 5.8
NMR signals at $\tau$= 2.5 (5 H), 2.6 (5H), 4.3–5.0 (6H), 5.65 (2 H), 5.8 (1H), 8.5 (6H).
Effectiveness against *El coli* 14: 6.25 units/ml.
Effectiveness against *Proteus* 1017: 12.5 units/ml.
Effectiveness against *Klebsiella* 63: 25 units/ml.
Effectiveness in animal experiments: A and B.

EXAMPLE 91

Sodium
D(—)-α-(3-[2-furoyl]-3-methyl-ureido)-benzylpenicillin

This penicillin was prepared from 35 parts by weight of ampicillin and 15 prts by weight of N-2-furoyl-N-methylcarbamic acid chloride, in the manner described in Example 83.
Yield: 83%
β-Lactam content: 83%
Calculated: C 52.7 H 4.4 N 10.7S 6.1 Found: C 52.8 H 5.4 N 9.8 S 6.1.
NMR signals at $\tau$= 2.3 (1 H), 2.3–2.9 (6H), 3.4 (1H), 4.3 (1 H), 4.5 (2H), 5.7 (1H), 6.6 (3H) and 8.5 ppm (6H).

EXAMPLE 92

A. N-2-Furoyl-N-n-propyl-carbamic acid chloride
This substance can be prepared according to the data in the literature, but especially according to the following process:
A solution of 7.6 parts by weight of 2-furanecarboxylic acid N-n-propylamide in a 2:1 mixture of ether and tetrahydrofurane (150 parts by volume), which had shortly before been distilled from LiAlH$_4$, was saturated with dry nitrogen and cooled to —30° C. 28.3 parts by volume of a 1.765 M solution of Ch$_3$Li in ether was added dropwise thereto under a nitrogen atmosphere over the course of 30 minutes, while excluding moisture and stirring vigorously. The mixture was stirred for a further 15 minutes at —30° C. The resulting suspension was added from a cooled dropping funnel, so that it did not rise above —10° C, to a mixture, at —10° C. of 50 parts by volume of phosgene and 50 parts by volume of absolute tetrahydrofurane, over the course of one hour. The mixture was allowed to come to room temperature after 15 minutes and stirred for a further 30 minutes, and the excess phosgene and the solvents were then stripped off in vacuo. The LiCl, which very largely remained undissolved, could substantially be separated off by suspending in benzene. The residue which remained after distilling off the benzene could be employed directly for the preparation of the penicillin. It could however also be distilled at 105°–112° C and 0.7 mm Hg. Yield 64%. In addition to the desired N-furoyl-N-propyl-carbamic acid chloride, the product also contained a further component, which however proved not to interfere in the subsequent preparation of the penicillin.

B. Sodium D(−)-α-(3-[2-furoyl]-3-n-propyl-ureido)-benzylpenicillin

This penicillin was prepared from 10.5 parts by weight of ampicillin and 6.5 parts by weight of distilled N-2-furoyl-N-n-propylcarbamic acid chloride, in the manner described in Example 83.

Yield: 30%

β-Lactam content: 90% NMR signals at τ= 2.35 (1H), 2.6 (5; H), 2.8 (1H), 3.4 (1H), 4.4 (1H), 4.5 (2H), 5.8 (1H), 6.2 (2H), 8.1–8.9 (1H), 8.5 (6H) and 9.1 ppm (3H).

EXAMPLE 93

A. N-2-Furoyl-N-ethyl-carbamic acid chloride

This substance was prepared from 7.0 parts by weight of 2-furanecarboxylic acid -N-ethylamide, $CH_3Li$ and phosgene, in the manner described in Example 92-A. Boiling point $_{1.5}$ = 90°– 95° C. Yield: 80% (crude product).

The substance contains a second component, which however proved not to interfere in the preparation of the penicillin.

B. Sodium D(−)-α-(3-[2-furoyl]-3-ethyl-ureido)-benzylpenicillin

This penicillin was prepared from 12 parts by weight of ampicillin and 7 parts by weight of N-2-furoyl-N-ethyl-carbamic acid chloride, in the manner described in Example 83. Yield: 29%

β-Lactam content: 89% Calculated: C 52.8 H 4.6N 10.7 Found:C52.6 H(6.2) N 9.7

NMR signals at τ= 2.3 (1 H), 2.6 (5H), 2.75 (1H), 3.4 (1 H), 4.35 (1H), 4.5 (2H), 5.8 (1H), 6.05 (2H), 8.45 (6H) and 8.7 ppm (3H).

EXAMPLE 94

Sodium D(−)-α-(3-dimethylaminocarbonyl-3-methyl-ureido)-benzylpenicillin

This penicillin was prepared from 17.5 parts by weight of ampicillin and 7.8 parts by weight of N-dimethylaminocarbonyl-N-methyl-carbamic acid chloride, in the manner described in Example 83.
Yield:74%

β-Lactam content: 82%

Calculated: C 49.6H 5.4N 13.8S 6.3 Found: C 49.9H 6.4N 13.1S 6.0

NMR signals at τ= 2.6 (5 H), 4.5 (3H), 5.8 (1H), 6.95 (3h), 7.05 (6 H) and 8.45 ppm (6H).

Effectiveness in animal experiments: A and B

EXAMPLE 95

If the N-dimethylaminocarbonyl-N-methyl-carbamic acid chloride used in Example 94 is replaced by:
- 3-dimethylaminocarbonyl-3-ethyl-carbamic acid chloride,
- 3-dimethylaminocarbonyl-3-propyl-carbamic acid chloride,
- 3-dimethylaminocarbonyl-3-i-propyl-carbamic acid chloride,
- 3-dimethylaminocarbonyl-3-n-butyl-carbamic acid chloride,
- 3-dimethylaminocarbonyl-3-allyl-carbamic acid chloride,
- 3-dimethylaminocarbonyl-3-cyclohexyl-cambamic acid chloride,
- 3-dimethylaminocarbonyl-3-phenyl-carbamic acid chloride,
- N-(1-pyrrolidylcarbonyl)-N-methyl-carbamic acid chloride,
- N-(1-piperidylcarbonyl)-N-methyl-carbamic acid chloride,
- N-diethylaminocarbonyl-N-methyl-carbamic acid chloride,
- N-ethylaminocarbonyl-N-methyl-carbamic acid chloride,
- N-methylaminocarbonyl-N-methyl-carbamic acid chloride,
- N-phenylaminocarbonyl-N-methyl-carbamic acid chloride,
- N-(4-morpholinyl-carbonyl)-N-methyl-carbamic acid chloride,
- N-(1-pyrrolidyl-carbonyl)-N-ethyl-carbamic acid chloride,
- N-(1-piperidylcarbonyl)-N-ethyl-carbamic acid chloride,
- N-diethylaminocarbonyl-N-ethyl-carbamic acid chloride,
- N-ethylaminocarbonyl-N-ethyl-carbamic acid chloride,
- N-methylaminocarbonyl-N-ethyl-carbamic acid chloride,
- N-phenylaminocarbonyl-N-ethyl-carbamic acid chloride,
- N-(4-morpholinylcarbonyl)-N-ethyl-carbamic acid chloride,
- N-(1-pyrrolidylcarbonyl)-N-n-propyl-carbamic acid chloride,
- N-(1-piperidylcarbonyl)-N-i-propyl-carbamic acid chloride,
- N-diethylaminocarbonyl-N-n-butyl-carbamic acid chloride or
- N-dimethylaminocarbonyl-N-cyclohexyl-carbamic acid chloride, the following penicillins are obtained in the form of their sodium salts.
- D(−)-α-(3-dimethylaminocarbonyl-3-ethyl-ureido)-benzylpenicillin,
- D(−)-α-(3-dimethylaminocarbonyl-3-propyl-ureido)-benzylpenicillin,
- D(−)-α-(3-dimethylaminocarbonyl-3-i-propyl-ureido)-benzylpenicillin,
- D(−)-α-(3-dimethylaminocarbonyl-3-n-butyl-ureido)-benzylpenicillin,
- D(−)-α-(3-dimethylaminocarbonyl-3-allyl-ureido)-benzylpenicillin,
- D(−)-α-(3-dimethylaminocarbonyl-3-cyclohexyl-ureido)-benzylpenicillin,
- D(−)-α-(3-dimethylaminocarbonyl-3-phenyl-ureido)-benzylpenicillin,
- D(−)-α-(3-[1-pyrrolidyl]-carbonyl-3-methyl-ureido)-benzylpenicillin,
- D(−)-α-(3-[1-piperidyl]-carbonyl-3-methyl-ureido)-benzylpenicillin,
- D(−)-α-(3-diethylaminocarbonyl-3-methyl-ureido)-benzylpenicillin,
- D(−)-α-(3-ethylaminocarbonyl-3-methyl-ureido)-benzylpenicillin,
- D(−)-α-(3-methylaminocarbonyl-3-methyl-ureido)-benzylpenicillin, D(−)-α-(3-phenylaminocarbonyl-3-methyl-ureido)-benzylpenicillin, D(−)-α-(3-[4-morpholinyl]-carbonyl-3-methyl-ureido)-benzylpenicillin, D(−)-α-(3-[1-pyrrolidyl]-carbonyl-3-ethyl-ureido)-benzylpenicillin, D(−)-α-(3-[1-piperidyl]-carbonyl-3-ethyl-ureido)-benzylpenicillin, D(−)-α-(3-diethylaminocarbonyl-3-ethyl-ureido)-benzylpenicillin, D(−)-α-(3-ethylaminocarbonyl-3-ethyl-ureido)-benzylpenicillin, D(−)-α-(3-methylaminocarbonyl-3-ethyl-ureido)-benzylpenicillin, D(−)-α-(3-phenylaminocarbonyl-3-ureido)-benzylpenicillin, D(−)-α-(3-[4-morpholinyl]-carbonyl-3-ethyl-ureido)-benzylpenicillin, D(−)-α-(3-[1-pyrrolidyl]-carbonyl-3-n-propyl-ureido)-benzylpenicillin, D(−)-α-(3-[1-piperidyl]-carbonyl-3-i-propyl-ureido)-benzylpenicillin, D(−)-α-(3-diethylaminocarbonyl-3-n-butyl-ureido)-benzylpenicillin or D(−)-α-(3-dimethylaminocarbonyl-3-cyclohexyl-ureido)-benzylpenicillin.

EXAMPLE 96

Sodium D(−)-α-(3-methoxycarbonyl-3-methyl-ureido)-benzylpenicillin

This penicillin was prepared from 24.5 parts by weight of ampicillin and 10.2 parts by weight of N-methoxycarbonyl-N-methylcarbamic acid chloride, in the manner described in Example 83.

Yield: 84%

β-Lactam content: 84%

Calculated: C 47.6 H 5.0 N 11.1 S 6.4 Found: C 48.4 H 5.5 N 10.6 S 5.8 NMR signals at $\tau$ = 2.3–2.9 (5 H), 4.4 (1 H), 4.5 (2 H), 5.8 (1 H), 6.2 (3 H), 6.8 (3 H) and 8.45 ppm (6 H).

Effectiveness against *E. coli* 14: 6.25 units/ml.

Effectiveness against *Pseudomonas aerug.* Bonn: 25 units/ml.

Effectiveness in animal experiments: A and B.

EXAMPLE 97

Sodium D(−)-α-(3-i-propoxycarbonyl-3-methyl-ureido)-benzylpenicillin

This penicillin was prepared from 24.4 parts by weight of ampicillin and 12.2 parts by weight of N-i-propoxycarbonyl-N-methyl-carbamic acid chloride, in the manner described in Example 83.

Yield: 72%

β-Lactam content: 88%

Calculated: C 51.3H 5.3N 10.9S 6.2

Found: C 51.6 H 5.5 N 10.6 S 6.1

NMR signals at $\tau$ = 2.3–2.8 (5 H), 4.4 (1 H), 4.5 (2 H), 5.0 (1 H), 5.8 (1 H), 6.85 (3 H), 8.5 (6 H) and 8.7 ppm (6 H).

Effectiveness against *E. coli* 14: 6.25 units/ml.

Effectiveness against *Proteus* 3400: 25 units/ml.

Effectiveness in animal experiments: A and B.

EXAMPLE 98

Sodium D(−)-α-(3-n-butoxycarbonyl-3-methyl-ureido)-benzylpenicillin

This penicillin was prepared from 24.5 parts by weight of ampicillin and 13.6 parts by weight of N-n-butoxycarbonyl-N-methyl-carbamic acid chloride, in the manner described in Example 83.

Yield: 63%

β-Lactam content: 78% Calculated: C 52.2 H 5.5 N 10.6 S 6.0 Found: C 52.2 H 5.5 N 10.7 S 6.0

NMR signals at $\tau$ = 2.3–2.8 (5 H), 4.45 (1 H), 4.55 (2 H), 5.8 (3 H), 6.85 (3 H) and 8.1–9.3 ppm (13 H).

Effectiveness against *E. coli* 14: 3.12 units/ml.

Effectiveness, against *Proteus* 1017: 12.5 units/ml.

Effectiveness against *Pseudomonas aerug.* Bonn: 12.5 units/ml.

Effective in animal experiments: A and B.

EXAMPLE 99

A. N-Benzoyl-N-phenyl-carbamic acid chloride

This substance was obtained from 19.7 parts by weight of benzoylanilide by reaction with CH$_3$Li and phosgene, in the manner described in Example 92-A. Instead of distilling, the product was recrystallised from benzene-petroleum ether.

Yield: 90%. Melting point 64°–66° C.

B. Sodium D(−)-α-(3-benzoyl-3-phenyl-ureido)-benzylpenicillin

The triethylamine salt was prepared from 11.5 parts by weight of ampicillin in methylene chloride, as described in Example 81. Instead of anhydrous sodium sulphate, 4 parts by weight of powdered Zeolite US 10 – 2 molecular sieve, added from the start, were used. Reaction with 7.8 parts by weight of N-benzoyl-N-phenylcarbamic acid chloride, as described in Example 81, though with the addition of a further 2.0 parts by weight of triethylamine to the reaction solution, yielded this penicillin.

Yield: 72%

β-Lactam content: 88%

Calculated: C 57.9H 4.8N 9.0S 5.4 Found: C 57.7 H 5.4 N 9.0 S 6.3

NMR signals at $\tau$ = 2.4–2.9 (15 H), 4.35 (1 H), 4.5 (2 H), 5.8 (1 H), 8.4 and 8.5 ppm (6 H).

Effectiveness in animal experiments: B.

EXAMPLE 100

D(−)-α-(3-[3-Nitro-4-methoxy-benzoyl]-3-methyl-ureido)-benzylpenicillin

This penicillin was prepared from 7.0 parts by weight ampicillin and 5.5 parts by weight of N-(3-nitro-4-methoxy-benzoyl)-N-methylcarbamic acid chloride, in the manner described in Examples 81 and 99-B.

Yield: 77%

β-Lactam content: 89%

Calculated: C 48.5 H 4.7 N 10.9 S 5.0 Found: C 48.4 H 5.4 N 10.8 S 5.4

The substance agrees with that of Example 83 as regards its IR and NMR spectrum.

EXAMPLE 101

A. 1-Chlorocarbonyl-hexahydroazepin-2-one

The substance was prepared from 6.8 parts by weight of ε-caprolactam and $CH_3Li$ and phosgene, in the manner described in Example 99-A.
Boiling point$_{0.2}$ = 80°–85° C. Yield: 37% of pure material.

B. Sodium D(−)-α-(hexahydroazepin-2-on-1-yl-carbonyl-amino)-benzylpenicillin This penicillin was prepared from 8.1 parts by weight of ampicillin and 4 parts by weight of 1-chlorocarbonylhexahydroazepin-2-one, in the manner described in Examples 81 and 99-B.
Yield: 40%
β-Lactam content: 90%
NMR signals at τ = 2.6 (5 H), 4.3–4.6 (3 H), 5.8 (1 H), 6.2–6.6 (2 H), 7.5–8.0 (2 H) and 8.0–8.9 ppm (12 H).

EXAMPLE 102

Sodium D(−)-α-(pyrrolid-2-on-1-yl-carbonylamino)-benzylpenicillin

This substance was prepared from 35 parts by weight of ampicillin and 15 parts by weight of 1-chlorocarbonyl-pyrrolidone, in the manner described in Example 83.
Yield: 83%
β-Lactam content: 70%
NMR signals at τ = 2.6 (5 H), 4.4 (1 H), 4.55 (2 H), 5.8 (1 H), 6.25 (2 H), 7.4 (2 H), 8.0 (2 H) and 8.5 ppm (6 H).

EXAMPLE 103

Sodium D(−)-α-(3-formyl-3-methyl-ureido)-benzylpenicillin

This penicillin was prepared from 35 parts by weight of ampicillin and 12.2 parts by weight of N-formyl-N-methyl-carbamic acid chooride, in the manner described in Examples 81 and 99-B.
Yield: 25%
β-Lactam content: 83%

EXAMPLE 104

If the N-formyl-N-methylcarbamic acid chloride used in Example 103 is replaced by:
N-formyl-N-ethylcarbamic acid chloride,
N-formyl-N-propylcarbamic acid chloride,
N-formyl-N-i-propylcarbamic acid chloride,
N-formyl-N-n-butylcarbamic acid chloride,
N-formyl-N-allylcarbamic acid chloride,
N-formyl-N-benzylcarbamic acid chloride,
N-formyl-N-phenylcarbamic acid chloride,
N-formyl-N-cyclopropylcarbamic acid chloride,
N-formyl-N-cyclobutylcarbamic acid chloride,
N-formyl-N-cyclopentylcarbamic acid choride or
N-formyl-cyclohexylcarbamic acid chloride;
the following penicillins are obtained in the form of their sodium salts:
sodium D(−)-α-(3-formyl-3-ethyl-ureido)-benzylpenicillin,
sodium D(−)-α-(3-formyl-3-propyl-ureido)-benzylpenicillin,
sodium D(−)-α-(3-formyl-3-i-propyl-ureido)-benzylpenicillin,
sodium D(−)-α-(3-formyl-3-n-butyl-ureido)-benzylpenicillin,
sodium D(−)-α-(3-formyl-3-allyl-ureido)-benzylpenicillin,
sodium D(−)-α-(3-formyl-3-benzyl-ureido)-benzylpenicillin,
sodium D(−)-α-(3-formyl-3-phenyl-ureido)-benzylpenicillin,
sodium D(−)-α-(3-formyl-3-cyclopropyl-ureido)-benzylpenicillin,
sodium D(−)-α-(3-formyl-3-cyclobutyl-ureido)-benzylpenicillin,
sodium D(−)-α-(3-formyl-3-cyclopentyl-ureido)-benzylpenicillin and
sodium D(−)-α-(3-formyl-3-cyclohexyl-ureido)-benzylpenicillin.

EXAMPLE 105

A. N-2-Furoyl-N-phenylcarbamic acid chloride:

The substance was prepared from 9.4 parts by weight of 2-furoylanilide by reaction with $CH_3Li$ and phosgene, in the manner described in Example 101-A.
Crude yield: 95%
The product was reacted, without further purification, to give the penicillin of Example 104-B.

B. Sodium D(−)-α-(3-[2-furoyl]-3-phenyl-ureido)-benzylpenicillin

This penicillin was prepared from 16.2 parts by weight of ampicillin and 11.5 parts by weight of N-2-furoyl-N-phenylcarbamic acid chloride, in the manner described in Example 83.
Yield: 50%
β-Lactam content: 91%
NMR signals at τ = 2.4 (1 H), 2.5 (11 H), 3.7 (1 H), 4.3–4.7 (3 H), 5.8 (1 H) and 8.45 ppm (6 H).

EXAMPLE 106

If, instead of the N-2-furoyl-N-phenylcarbamic acid chloride used in Example 105, 0.03 mol of:
N-(2,5-dimethyl-fur-3-oyl)-N-methylcarbamic acid chloride,
N-(5-bromo-fur-3-oyl)-N-methylcarbamic acid chloride,
N-(5-methoxymethylfur-2-oyl)-N-methylcarbamic acid chloride or
N-3,5-(dimethylisothiazol-3-yl-carbonyl)-N-methylcarbamic acid chloride are reacted with ampicillin, the sodium salts of the following penicillins are obtained:
D(−)-α-(3-[2,5-dimetyl-furoyl-(3) ]-3-methyl-ureido-benzylpenicillin,
D(−)-α-(3-[5-bromo-furoyl-(3) ]-3-methyl-ureido)-benzylpenicillin,
D(−)-α-(3-[5-methoxymethyl-furoyl-(2) ]-3-methyl-ureido)-benzylpenicillin or
D(−)-α-(3-[3,5-dimethylisothiazole-3-yl-carbonyl]-3-methyl-ureido)-benzylpenicillin.

EXAMPLE 107

Sodium D(−)-α-(3-chlorobenzoyl-3-methyl-ureido-benzylpenicillin 16.2 parts by weight of N-o-chlorobenzoyl-N-methylcarbamic acid chloride and 5 parts by weight of triethylamine were added at −10° C to a solution of the triethylamine salt of 28 parts by weight of ampicillin in 300 parts by volume of methylene chloride, the mixture was stirred, with exclusion of moisture, for 30 minutes at this temperature, and subsequently for a further 2 hours at 0° C, and was then poured into ice water, and the pH was adjusted to 6.5. Thereafter, the organic phase was speparated off, and the aqueous phase was covered with ether/ethyl acetate mixture and adjusted to pH = 1.5–2.0 with dilute hydrochloric acid, while cooling with ice. After having separated off the organic phase and again having extracted the water with ether-/ethyl acetate mixture, the combined organic solutions were dried over MgSO$_4$ and filtered, and about 70 parts by volume of a 1 molar solution of sodium 2-ethylhexanoate in ether containing methanol were added to the filtrate. The mixture was evaporated almost to dryness in vacuo, the residue was dissolved in methanol, and the product was precipitated as a non-crystalline, white solid substance by adding ether.

Yield: 26%
β-Lactam content: 81%
Calculated: C 51.3 H 4.5 Cl 6.1 N 9.6 Found: C 51.4 H 5.9 Cl 5.6 N 9.0
NMR signals at $\tau$= 2.3–2.8 (9 H), 4.3 (1 H), 4.5 (2 H), 5.8 (1 H), 6.95 (3 H) and 8.5 ppm (6 H).
Effectiveness in animal experiments: A and B
Effectiveness in animal experiments against *Pseudomonas aerug.* Walter: better than carbenicillin.

EXAMPLE 108

Sodium D(−)-α-(3-[3-nitro-4-methoxy-benzoyl]-3-ethyl-ureido)benzylpenicillin:

This penicillin was prepared from 14.8 parts by weight of ampicillin and 12.2 parts by weight of N-(3-nitro-4-methoxybenzoyl)-N-ethyl-carbamic acid chloride, as described in

EXAMPLE 107.

Yield: 24% β-Lactam content: 86%
Calculated: C 49.2 H 4.9 n 10.6 S 4.9
Found: C 49.2 H 5.3 N 10.1 S 5.5
NMR signals at $\tau$= 2.0 (1 H), 2.3 (1 H), 2.4–1.9 (6 H), 4.5 (3 H), 5.9 (1 H), 6.1 (3 H), 6.2 (2 H), 8.3–9.0 ppm (9 H).
Effectiveness in animal experiments: A and B

EXAMPLE 109

Sodium D(-)-α-(3-[3-nitro-4-methoxybenzoyl]-3-n-propylureido)-benzylpenicillin

This penicillin was prepared from 21 parts by weight of ampicillin and 18 parts by weight of N-(3-nitro-4-methoxybenzoyl9 -N-n-propyl-carbamic acid chloride, in the manner described in Example 107.
Yield: 16% β-Lactam content: 90%
NMR signals at $\tau$= 2.0 (1 H), 2.3 81 H), 2.5–3.0 (6 H), 4.45 (1 H), 4.55 (2 H), 5.8 (1 H), 6.05 (3H), 6.1–6.6 (2 H) and 8.45–9.1 ppm (11 H).
Effectiveness in animals experiments: A and B.

EXAMPLE 110

Sodium D(−)-α-(3-methylaminocarbonyl-3-methyl-ureido)-benzylpenicillin:

This penicillin was prepared from 30 parts by weight of ampicillin and 10.5 parts by weight of N-methylaminocarbonyl-N-methyl-carbamic acid chloride, in the manner described in Example 107.
Yield: 92%
β-Lactam content: 93%
Calculated: C 48.6 H 5.1 N 14.1 S 6.5
Found: C 49.0 H 6.3 N 12.6 S 6.9
NMR signals at $\tau$= 2.6 (5 H), 4.45 (1 H), 4.5 (2 H), 5.8 (1 H), 6.8 (3 H), 7.2 (3 H) and 8.4 ppm (6 H). Effectiveness in animal experiments: B.

EXAMPLE 111

Sodium D(−):α-(3-[2,5-dichlorobenzoyl]-3-methyl-ureido)-benzylpenicillin

This penicillin was prepared from 28 parts by weight of ampicillin and 18.7 parts by weight of N-(2.5-dichlorobenzoyl)N-methylcarbamic acid chloride, in the manner described in Example 107.
Yield: 32%
β-Lactam content: 85%
Calculated: C 47.6 H 4.2 Cl 11.1 N 8.8
Found: C 48.0 H(6.0) Cl 9.7 N 8.6
NMR signals at $\tau$= 2.3-2.8 (8 H), 4.35 (1 H), 4.5 (2 H), 5.8 (1 H), 6.9 (3 H), 8.4 (3 H) and 8.5 ppm (3 H).

EXAMPLE 112

Sodium D(−)-α-(3-p-chlorobenzoyl-3-methyl-ureido)-benzylpenicillin

This penicillin was prepared from 28 parts by weight of ampicillin and 16 parts by weight of N-p-chlorobenzoyl-N-methylcarbamic acid chloride, in the manner described in Example 107.
Yield: 16%
β-Lactam content: 82%
Calculated: C 51.3 H 4.5 Cl 6.1 N 9.5 S 5.5 Found: C 51.9 H 5.6 Cl 5.4 N 9.1 S 5.5
NMR signals at $\tau$= 2.3–2.8 (9 H), 4.35 (1 H), 4.5 (2 H), 5.8 (1 H), 6.95 (3 H), 8.4 (3 H) and 8.5 ppm (3 H).
Effectiveness in animal experiments: B.

EXAMPLE 113.

Sodium (D−)-α-(3-propionyl-3-methyl-ureido)-benzylpenicillin 6.0 parts by weight off N-propionyl-N-methyl-carbamic acid chloride in 25 parts by volume of absolute tetrahydrofurane were added dropwise, at 0° C, to a solution of 18 parts by weight of ampicillin in 180 parts by volume of 80% strength aqueous tetrahydrofurane (pH = 8.2 adjusted with triethylamine), while keeping the pH at 7–8 by adding triethylamine. Thereafter the mixture was further stirred at 0° C until no more triethylamine had to be added to maintain the pH at 7 (about 15 minutes). Water was now added, the tetahydrofurane was stripped off in vacuo, the residue was extracted once with ether/ethyl acetate mixture, and the aqueous phase was covered with fresh ether/ethyl acetate mixture. Thereafter a pH of 1.5–2.0 was established by adding dilute hydrochloric acid at 0° C, whereupon the mixture was worked up as in Example 107, and the penicillin was precipitated as the sodium salt.
Yield: 85%
β-Lactam content: 91%
Calculated: C 51.1 H 5.3 N 11.3 s 6.5 Found : C 51.2 H 6.4 N 11.1 S 7.5
NMR signals at $\tau$= 2.3–2.8 (5 H), 4.4 (1 H), 4.5 (2 H), 5.8 (1 H), 6.8 (1 H), 7.4 (2 H), 8.4 (3 H), 8.5 (3 H) and 8.8 ppm (3 H).
Effectiveness in animal experiments: B.

EXAMPLE 114

Sodium D(−)-α-(3-acetyl-3-ethyl-ureido)-benzylpenicillin

This penicillin was prepared from 18 parts by weight of ampicillin and 6 parts by weight of N-acetyl-N-ethyl-carbamic acid chloride in the manner described in Example 113.
Yield: 62%
β-Lactam content: 89%
Calculated C 50.6 H 5.4 N 11.2 S 6.5 Found: C 50.7 H 6.3 N 10.8 S 6.9
signals at $\tau$= 2.4–2.8 (5 H), 4.4 (1 H), 4.5 (2 H), 5.8 (1 H), 6.25 (2 H), 7.7 (3 H), 8.45 (6 H) and 8.8 ppm (3 H).
Effectiveness in animal experiments: B.

EXAMPLE 115

Sodium D(−)-α-(3-acetyl-3-n-propyl-ureido)-benzylpenicillin

This penicillin was prepared from 28 parts by weight of ampicillin and 10 parts by weight of N-acetyl-N-n-propylcarbamic acid chloride, in the manner described in Example 113.
Yield: 67%
-Lactam content: 89.
Calculated: C 53.0 H 5.4 N 11.2 S 6.4 Found: C 52.5 H(6.6) N 10.5 S6.4
NMR signals at $\tau$= 2.3–2.8 (5 H), 4.4 (1 H), 4.5 (2 H), 5.8 (1 H), 6.3 (2 H), 7.65 (3 H), 8.2–8.7 (8 H), and 9.1 ppm (3 H).

EXAMPLE 116

Sodium D(−)-α-(3-i-butyryl-3-methyl-ureido)-benzylpenicillin

This penicillin was prepared from 28 parts by weight of ampicillin and 10 parts by weight of N-i-butyryl-N-methylcarbamic acid chloride, in the manner described in Example 113.
Yield: 33%
β-Lactam content: 91%
Calculated: C 51.1 H 5.6 N 10.8 Found: C 50.8 H 6.4 N 10.9.
NMR signals at $\tau$= 2.4–2.8 (5 H), 4.45 (1 H), 4.55 (2 H), 5.85 (1 H), 6.7 (3 H), 7.1 ( 1 H), 8.5 (6 H) and 8.9 ppm (6 H).
Effectiveness in animal experiments: B.

Examples 117

Sodium D(−)-α-(3-m-chlorobenzoyl-3-methyl-ureido)-benzyl-penicillin

This penicillin was prepared from 19.7 parts by weight of ampicillin and 10 parts by weight of N-m-chlorobenzoyl-Nmethyl-carbamic acid chloride, in the manner described in Example 113.
Yield: 62%
β-Lactam content: 86%
Calculated: C 51.5 H 4.4 Cl 6.1 N 9.6 S 5.6 Found: C 52.1 H(6.0) Cl 5.6 N 9.4 S 5.5
NMR signals at $\tau$= 2.4–2.8 (9 H), 4.35 (1 H), 4.5 (2 H), 5.8 (1 H), 6.85 (3 H), and 8.45 ppm (6 H).

EXAMPLE 118

Sodium α-(3-acetyl-3-methyl-ureido)-4-methylbenzylpenicillin

This penicillin was prepared from 2. 1 parts by weight of α-amino-4-methyl-benzylpenicillin and 1.2 parts by weight of N-acetyl-N-methyl-carbamic acid chloride, in the manner described in Example 113.
Yield: 45%
β-Lactam content: (determined by IR spectroscopy): 75%,
NMR signals at $\tau$ = 2.65 (2 H), 2.8 (2 H), 4.4–4.6 (3 H), 5.8 (1 H), 6.75 (3 H), 7.7 (6 H) and 8.25 to 8.55 ppm (6 H).

EXAMPLE 119

Sodium R,S-α-(3-dimethylaminocarbonyl-3methyl-ureido)-4-methylbenzylpenicillin

This penicillin was prepared from 1.8 parts by weight of R,S-α-amino-4-methyl-benzylpenicillin and 1.6 parts by weight of N-dimethylaminocarbonyl-N-methyl-carbamic acid chloride, as described in Example 83.
Yield:
β-Lactam content: (determined by IR spectroscopy): 65%
NMR signals at $\tau$= 2.5–2.9 (4 H), 4.4–4.7 (3 H), 5.8 (1 H), 6.9 (3 H), 7.05 (6 H), 7.7 (3 H) and 8.4 ppm (6 H).

EXAMPLE 120

Sodium R,S-α-(3-dimethylaminocarbonyl-3-methyl-ureido)-4-chlorobenzylpenicillin:

This penicillin was prepared from 2.7 parts by weight of R,S-α-amino-4-chloro-benzylpenicillin and 2.0 parts by weight of N-dimethylaminocarbonyl-N-methyl-carbamic acid chloride, as described in Example 113.
Yield: 43%
β-Lactam content: (determined by IR spectroscopy): 55–60%.
NMR signals at $\tau$ = 2.6 (4 H), 4.5 (3 H), 5.7 (1 H), 6.95 (3 H), 7.05 (6 H) and 8.3 to 8.5 ppm (6 H).

EXAMPLE 121

Sodium R,S-α-(3-acetyl-3-methyl-ureido)-4-chlorobenzyl-penicillin:

This penicillin was prepared from 1.8 parts by weight of D,L-α-amino-4-chloro-benzylpenicillin and 1.0 part by weight of N-acetyl-N-methyl-carbamic acid chloride, as described in Example 113.
Yield: 80%
β-Lactam content: (determined by IR spectroscopy): 55–60%
NMR signals at $\tau$= 2.4–2.8 (4 H), 4.3–4.6 (3 H), 5.8 (1 H), 6.7 (3 H), 7.65 (3 H) and 8.3–8.5 ppm (6 H).

EXAMPLE 122

Sodium
D,L-α-(3-acetyl-3-methyl-ureido)-α-thienyl(2)-methylpenicillin

This penicillin was prepared from 3.5 parts by weight of D,L-α-amino-α-thienyl(2)-methyl-penicillin and 1.7 parts by weight of N-acetyl-N-methyl-carbamic acid chloride, as described in Example 113.
Yield: 42%
β-Lactam content: (determined by IR spectroscopy): 80% NMR signals at $\tau$= 2.3–3.2 (3 H), 4.1–4.6 (3 H), 5.8 (1 H), 6.8 (3 H), 7.7 (3 H) and 8.3–8.6 ppm (6 H).

EXAMPLE 123

Sodium
D(−)-α-(3-[1-piperidyl]-carbonyl-3-methyl-ureido)-benzylpenicillin

This penicillin was prepared from 30 parts by weight of ampicillin and 13.5 parts by weight of N-(1-piperidylcarbonyl)N-methyl-carbamic acid chloride, in the manner described in Example 59.
Yield: (crude product): 66%
β-Lactam content: 97%
Calculated: C 53.4 H 5.6 N 12.9 S 5.9 Found: C 53.1 H 6.5 N 12.3 S 6.3
NMR signals at $\tau$= 2.6 (5 H), 4.5 (3 H), 5.8 (1 H), 6.6 (4 H), 6.9 (3 H) and 8.4 ppm (12 H).
Effectiveness against E. coli 14: 3.12 units/ml.
Effectiveness against Klebsiella K 10: 50 units/ml.

EXAMPLE 124

Sodium
D(−)-α-(3-[1-pyrrolidyl]-carbonyl-3-methyl-ureido)-benzylpenicillin

This penicillin was prepared from 30 parts by weight of ampicillin and 12.6 parts by weight of N-(1-pyrrolidylcarbonyl)N-methylcarbamic acid chloride, in the manner described in Example 59.
Yield (crude product) : 72%
β-Lactam content: 96%
Calculated: N 13.3 S 6.1 Found: N 13.2 S 6.1
NMR signals at $\tau$= 2.6 (5 H), 4.5 (3 H), 5.8 (1 H), 6.5–6.8 (4 H), 6.9 (3 H), 8.0–8.3 (4 H) and 8.5 ppm (6 H).
Effectiveness against E. coli 14: 3.12 units/ml.
Effectiveness against Proteus 3400: 50 units/ml.
Effectiveness in animal experiments: A.

EXAMPLE 125

Sodium
D(−)-α-(3-[4-morpholinyl]-carbonyl-3-methyl-ureido) benzylpenicillin:

This penicillin was prepared from 30 parts by weight of ampicillin and 13.6 parts by weight of N-(4-morpholinylcarbonyl)-N-methyl-carbamic acid chloride, in the manner described in Example 59.
Yield: (crude product): 80%
β-Lactam content: 93%
Calculated: N 12.9 S 5.9 Found: N 11.8 S 5.9
NMR signals at $\tau$ = 2.6 (5 H), 4.5 (3 H), 5.9 (1 H), 6.3–6.8 (8 H), 6.9 (3 H) and 8.5 ppm (6 H).
Effectiveness against Proteus 1017: 50 units/ml.
Effectiveness in animal experiments: A.

EXAMPLE 126

Sodium
D(−)-α-(3-diethylaminocarbonyl-3-methyl-ureido)-benzylpenicillin:

This penicillin was prepared from 30 parts by weight of ampicillin and 12.7 parts by weight of N-diethylaminocarbonylN-methyl-carbamic acid chloride, in the manner described in Example 59.
Yield: (crude product): 46%
β-Lactam content 97%
Calculated: N 13.3 S 6.1 Found: N 12.9 S 6.0
NMR signals at $\tau$ = 2.6 (5 H), 4.5 (3 H), 5.8 (1 H), 6.5–7.0 (7 H), 8.4 (6 H) and 8.7–9.0 ppm (6 H).
Effectiveness against E. coli 14: 12.5 units/ml.

EXAMPLE 127

Sodium
D(−)-α-(3-[2-nitro-4-chlorobenzoyl]-3-methyl-ureido)benzylpenicillin

This penicillin was prepared from 21 parts by weight of ampicillin and 12.8 parts by weight of N-(2-nitro-4-chlorobenzoyl)-N-methyl-carbamic acid chloride, in the manner described in Example 59.
Effectiveness Yield (crude product): 81%
β-Lactam content: 95%
Calculated: N 11.4 S 5.2 Found: N 10.6 S 5.1
NMR signals at $\tau$ = 1.7 (1 H), 2.1–2.5 (2 H), 2.6 (5 H), 4.3–4.6 (3 H), 5.8 (1 H), 6.9 (3 H) and 8.4 ppm (6 H).
Effectiveness against Proteus 1017: 3.12 units/ml. Effectiveness against Pseudomonas aerug. Bonn: 12.5 units/ml.
Effectiveness aginst Klebsiella k 10: 12.5 units/ml.
Effectiveness in animal experiments: A and B.

EXAMPLE 128

Sodium
D(−)-α-(3-[2-bromobenzoyl]-3-methyl-ureido)-benzyl penicillin

This penicillin was prepared from 30 parts by weight of ampicillin and 18.3 parts by weight of N-(2-bromobenzoyl)-Nmethyl-carbamic acid chloride, in the manner described in Example 59.
Yield (crude product): 64%
β-Lactam content: 95%
NMR signals at $\tau$ = 2.2–2.7 (9 H), 4.3–4.6 (3 H), 5.8 (1 H), 7.0 (3 H) and 8.4 ppm (6 H).
Effectiveness against Proteus 1017: 1.56 units/ml.
Effectiveness against Pseudomonas aerug Bonn: 6.25 units/ml
Effectiveness in animal experiments: A and B.

EXAMPLE 129

Sodium
D(−)-α-(3-[2-methylbenzoyl]-3-methyl-ureido)-benzylpencillin

This penicillin was prepared from 30 parts by weight of ampicillin and 14.4 parts by weight of N-(2-methylbenzoyl)N-methyl-carbamic acid chloride, in the manner described in Example 59.
Yield (crude product): 66%
β-Lactam content: 93%
NMR signals at $\tau$= 2.4–2.8 (9 H), 4.3–4.6 (3 H), 5.8 (1 H), 7.0 (3 H), 7.7 (3 H) and 8.5 ppm (6 H).
Effectiveness against Proteus 1017: 3.12 units/ml.

Effectiveness against *Pseudomonas aerug. Bonn:* 6.25 units/ml.
Effectiveness in animal experiments: A and B.

EXAMPLE 130

Sodium
D(−)-α-(3-acetyl-3-phenyl-ureido)-benzylpenicillin

This penicillin was prepared from 10 parts by weight of N-acetyl-N-phenylcarbamic acid chloride and 19 parts by weight of ampicillin, in the manner described in Example 113.
Yield: 86%
β-Lactam content: 85%
Calculated: C 53.1 H 5.0 N 9.9 S 5.7 Found: C 53.6 H 5.5 N 9.8 S 5.7
NMR signals at $\tau$= 2.4–2.8 (10 H), 4.4 (1 H), 4.55 (2 H), 5.8 (1 H), 8.1 (3 H), 8.4 (3 H) and 8.5 ppm (3 H).
Effectiveness in animal experiments: B.

EXAMPLE 131

Sodium
D(−)-α-(3-m-nitrocinnamoyl-3-methyl-ureido)-benzylpenicillin

This penicillin was prepared from 18.9 parts by weight of N-(m-nitrocinnamoyl)-N-methyl-carbamic acid chloride and 28 parts by weight of ampicillin, in the manner described in Example 113.
Yield: 78%
β-Lactam content: 88%
Calculated: C 47.9 H 5.4 N 10.2 S 4.8 Found: C 47.5 H 5.0 N 10.4 S 5.4
NMR signals at $\tau$ = 1.6 (1 H), 1.7–2.9 (8 H), 4.4 (1 H), 4.5 (2 H), 5.8 (1 H), 6.6 (3 H) and 8.5 ppm (6 H).
Effectiveness in animal experiments: A and B.

EXAMPLE 132

Sodium
D(−)-α-(3-[4-nitrophenacetyl]-3-methyl-ureido)-benzylpenicillin

This penicillin was prepared from 16.3 parts by weight of N-p-nitrophenacetyl-N-methyl-carbamic acid chloride and 28 parts by weight of ampicillin, in the manner described in Example 113.
Yield: 92%
β-Lactam content: 84%
Calculated: C 51.1 H 4.6 N 11.5 S 5.3 Found: C 51.3 H 5.4 N 11.2 S 5.7
NMR signals at $\tau$ = 1.8 (2), 2.5 (2 H), 2.6 (5 H), 4.4 (1 H), 4.55 (2 H), 2.6 (1 H), 5.85 (2 H), 6.7 (3 H), 8.4 (3 H), and 8.5 ppm (3 H).
Effectiveness in animal experiments: A and B.

EXAMPLE 133

D(−)-α-(1-Imidazolidin-2-on-1-yl carbonylamino)-benzylpenicillin

This penicillin was prepared from 5.4 parts by weight of N-chlorocarbonyl-imidazolidin-2-one and 12.7 parts by weight of ampicillin in the manner described in Example 59. After acidification, the product was obtained as the free penicillin acid, which is sparingly soluble in ethyl acetate. and which was filtered off, washed with water and dried over $P_2O_5$ in vacuo.
Yield: 72%
β-Lactam content: 93%
Calculated: C 50.1 H 5.0 N 14.6 S 6.7 Found: C 50.1 H 5.6 N 13.8 S 6.8

NMR signals at $\tau$ = 0.9 (2 H), 2.35 (1 H), 2.6 (5 H), 4.25 (1 H), 4.55 (2 H), 5.7 (1 H), 6.0–7.0 (4 H), 8.4 (3 H) and 8.55 ppm (3 H) Solvent: DMSO-$D_6$.

EXAMPLE 134

Sodium
D(−)-α-(1-piperidin-2-on-1-yl-carbonylamino)-benzylpenicillin

This penicillin was prepared from 9 parts by weight of 1-chlorocarbonyl-2-chloro-1,4,5,6-tetrahydropyridine and 21 parts by weight of ampicillin in the manner described in Example 113.
Yield: 85%
β-Lactam content: 89%
NMR signals at $\tau$ = 2.4–2.8 (5 H), 4.4 (1 H), 4.45 (1 H) 4.55 (1 H), 5.8 (1 H), 6.15–6.5 (2 H), 7.6–8.0 (2 H) and 8.0–8.6 ppm (10 H).
Effectiveness in animal experiments: A and B.

EXAMPLE 135

Sodium
α-(3-o-chlorobenzoyl-3-methyl-ureido)-α-thienyl(2)-methylpenicillin:

This penicillin was prepared from 1.9 parts by weight of N-o-chlorobenzoyl-N-methylcarbamic acid chloride and 1.5 parts by weight of α-amino-α-thienyl(2)-methylpenicillin in the manner described in Example 113.
Yield: 35%
βLactam content: 55–60% (estimated from the IR spectrum).
NMR signals at $\tau$ = 2.4–3.1 (7 H), 4.3–4.5 (3 H), 5.8 (1 H), 6.9 (3 H) and 8.2–8.6 ppm (6 H).
Effectiveness in animal experiments: B.

EXAMPLE 136

Sodium
D(−)-α-(3-methyl-1,3-diazcyclohexane-2-on-1-yl-carbonyl-amino)-benzylpenicillin This penicillin was prepared from 12.4 parts by weight of 1-chloro-carbonyl-2-oxo-3-methyl-1,3-diazacyclohexane and 17.5 parts by weight of ampicillin, in the manner described in Example 113.
Yield: 46%
β-Lactam content: 90%
Calculated: C 50.1 H 5.3 N 13.3 S 6.1 Found: C 50.4 H 6.2 N 13.1 S 6.4
NMR signals at $\tau$ = 2.3–2.8 (5 H), 4.3–4.6 (3 H), 5.8 (1 H), 6.25 (2 H), 6.4–6.8 (2 H), 7.0 (3 H), 8.0 (2 H), 8.4 (3 H) and 8.5 ppm (3 H).

EXAMPLE 137

Sodium
D(−)-α-(3-o-fluorobenzoyl-3-methyl-ureido)-benzylpenicillin

This penicillin was prepared from 9.05 parts by weight of N-o-fluorobenzoyl-N-methyl-carbamic acid chloride and 17.5 parts by weight of ampicillin, in the manner described in Example 113.
Yield: 88%
β-Lactam content: 92%
Calculated: C 54.6 H 4.4 N 10.2 S 5.8 Found: C 54.2 H(5.6) N 10.1 S 5.8
NMR signals at $\tau$ = 2.4–2.9 (9 H), 4.35 (1 H), 4.5 (2 H), 5.8 (1 H), 6.8 (3 H) and 8.5 ppm (6 H).

EXAMPLE 138

Sodium
D(−)-α-(3-o-chlorobenzoyl-3-ethyl-ureido)-benzyl-
penicillin

This penicillin was prepared from 10.7 parts by weight of N-o-chlorobenzoyl-N-ethyl-carbamic acid chloride and 17.5 parts by weight of ampicillin, in the manner described in Example 113
Yield: 90%
β-Lactam content: 93%
Calculated: C 52.5 H 4.6 Cl 6.0 N 9.4 S 5.4 Found: C 52.3 H 5.4 Cl 5.6 N 9.2 S 5.4
NMR signals at $\tau = 2.3$–2.8 (9 H), 4.35 (1 H), 4.5 (2 H), 5.8 (1 H), 6.4 (2 H), 8.4 (3 H), 8.5 (3 H) and 9.0 ppm (3 H).

EXAMPLE 139

Sodium
D(−)-α-(3-o-chlorobenzoyl-3-n-propyl-ureido)-ben-
zylpenicillin

This penicillin was prepared from 11.0 parts by weight of N-o-chlorobenzoyl-N-n-propyl-carbamic acid chloride and 17.5 parts by weight of ampicillin, in the manner described in Example 113.
Yield: 82%
β-Lactam content: 92%
Calculated: C 53.3 Cl 5.8 N 9.2 H 4.8 S 5.3 Found: C 53.7 Cl 5.4 N 9.2 H(6.2) S 5.6
NMR signals at $\tau = 2.3$–2.8 (9 H), 4.4 (1 H), 4.5 (2 H), 5.8 (1 H), 6.3–6.7 (2 H), 8.2–8.7 (2 H), 8.4 (3 H), 8.5 (3 H) and 9.3 ppm (3 H).

EXAMPLE 140

Sodium
D(−)-α-(3-o-nitrobenzoyl-3-methyl-ureido)-benzyl-
penicillin

This penicillin was prepared from 12.1 parts by weight of N-o-nitrobenzoyl-N-methyl-carbamic acid chloride and 21 parts by weight of ampicillin, in the manner described in Example 113.
Yield: 94%
β-Lactam content: 92%
Calculated: C 51.1 H 4.3 N 11.9 S 5.5 Found: C 50.9 H 5.3 N 11.1 S 5.6
NMR signals at $\tau = 1.75$ (1 H), 2.05–2.8 (8 H), 4.35 (1 H), 4.5 (2 H), 5.8 (1 H), 6.95 (3 H), 8.4 (3 H) and 8.5 (3 H).
Effectiveness in animal experiments: B.

EXAMPLE 141

Sodium
D(−)-α-(3,o,o'-dichlorobenzoyl-3-methyl-ureido)-
benzylpencillin

This penicillin was prepared from 13.3 parts by weight of N-o,o'-dichlorobenzoyl-N-methyl-carbamic acid chloride and 21 parts by weight of ampicillin, in the manner described in Example 113.
Yield: 91%
β-Lactam content: 91%
Calculated: C 48.6 H 4.0 Cl 11.5 N 9.1 S 5.2 Found: C 48.9 H 4.5 Cl 11.1 N 8.9 S 5.3
NMR signals at $\tau = 2.3$–2.8 (8 H), 4.3 (1 H), 4.5 (2 H), 5.75 (1 H), 6.9 (3 H), 8.4 (3 H) and 8.5 ppm (3 H).
Effectiveness in animal experiments: B.

EXAMPLE 142

Sodium
D(−)-α-(3-[2,4-dichlorobenzoyl]-3-methyl-ureido)-
benzylpenicillin

This penicillin was prepared from 13.3 parts by weight of N-(2,4-dichlorobenzoyl)-N-methyl-carbamic acid chloride and 21 parts by weight of ampicillin, in the manner described in Example 113.
Yield: 84%
β-Lactam content: 92%
Calculated: C 48.6 H 4.0 Cl 11.5 N 9.1 S 5.2 Found: C 48.7 H 4.6 Cl 10.9 N 9.0 S 5.8
NMR signals at $\tau = 2.4$ (1 H), 2.4–2.8 (7 H), 4.35 (1 H), 4.5 (2 H), 5.8 (1 H), 6.9 (3 H), 8.4 (3 H) and 8.5 ppm (3 H).
Effectiveness in animal experiments: A and B.

EXAMPLE 143

Sodium
D(−)-α-(3-propionyl-3-phenyl-ureido)-benzylpenicil-
lin

This penicillin was prepared from 15.5parts by weight of N-propionyl-N-phenyl-carbamic acid chloride and 27.5 parts by weight of ampicillin, in the manner described in Example 113.
Yield: 78%
β-Lactam content: 87%
Calculated: C 55.3 H 5.1 N 9.9 S 5.7 Found: C 55.1 H 5.1 N 9.8 S 6.0 NMR signals at $\tau = 2.2$–2.3 (10 H), 4.4 (1 H), 4.5 (2 H), 5.75 (1 H), 7.9 (2 H), 8.4 (3 H), 8.5 (3 H) and 9.0 ppm (3 H).
Effectiveness in animal experiments: B.

EXAMPLE 144

A.

D(−)-α-(Imidazolidin-2-on-1-yl-carbonylamino)-ben-
zylpenicillin 14 parts by weight of D-α-aminobenzylpenicillin (ampicillin) were suspended in 80% strength aqueous tetrahydrofurane (130 parts by volume) and sufficient triethylamine (approx. 6.5 parts by volume) was added dropwise, while stirring, at 20° C, that a clear solution was just produced and the pH value was between 7.5 and 8.2 (glass electrode). The mixture was now cooled to 0° C and a solution of 5.4 parts by weight of N-chlorocarbonyl-imidazolidin-2-one in 25 parts by volume of absolute tetrahydrofuran was added dropwise over the course of 30 minutes, while cooling with ice and stirring vigorously, the pH value being kept between 7.5 and 8.0 by simultaneous addition of triethylamine. The mixture was further stirred for 30 minutes at 0° C and subsequently at room temperature until no further addition of triethylamine was necessary to maintain the pH value of 7.5. 130 parts by volume of water were now added and the tetrahydrofurane was largely removed in a rotary evaporator at room temperature. The aqueous solution which remained was once extracted by shaking with ether, covered with 300 parts by volume of ethyl acetate, cooled to 0° C and treated with sufficient dilute hydrochloric acid, while stirring and cooling with ice, to establish a pH value of 1.5 to 2.0. The organic phase was separated off, the aqueous suspension was again extracted with about 300 parts by volume of ethyl acetate, and the organic extracts were combined.

The penicillin, which is rather sparingly soluble in ethyl acetate and which was suspended in the aqueous phase, was filtered off, carefully washed with ice water until free of acid, and dried in vacuo at about 1 mm Hg over $P_2O_5$. The substance is crystalline; long needles are visible under the microscope.

Yield: 71%

β-Lactam content: 93%

Calculated: C 50.1 H 5.0 N 14.6 S 6.7 Found: C 50.1 H 5.6 N 13.8 S 6.8 NMR signals (dimethylsulphoxide-$d_6$ as the solvent) at $\tau = 0.9$ (2 H), 2.35 (1 H), 2.6 (5 H), 4.25 (1 H), 4.55 (2 H), 5.7 (1 H), 6.0–7.0 (4 H), 8.4 (3 H) and 8.55 ppm (3 H). IR bands at 3380, 3230, 1784, 1728, 1687, 1639, 1520, 1375, 1219 and 735 $cm^{-1}$.

According to separation in a paper chromotogram and subsequent developement B. *subtilis*, the product only contains one antibiotically active component.

A further 0.45 part by weight (2.6% of theory) of the penicillin, in the form of its sodium salt, could be isolated from the ethyl acetate extract after addition of about 2 parts by volume of a 1 molar solution of sodium 2-ethyl-hexanoate in ether containing methanol.

The free acid of the penicillin can be easily converted into the chemotherapeutically usable salts by conventional processes. (See Example 150A).

B. 1-Chlorocarbonyl-imidazolidone(2)

4 parts by weight of phosgene in 10 parts by volume of absolute tetrahydrofuran were added dropwise, over the course of 15 minutes, to a vigorously stirred solution of 3.5 parts by weight of imidazolidone(2) [manufactured according to Fischer and Koch, Ann, 232, page 224 (1886)] in 50 parts by volume of absolute tetrahydrofuran. Thereafter the reaction mixture was stirred for 3 hours at 10° C and a stream of dry air was then passed through it, in order to blow out the hydrochloric acid formed, and remnants of phosgene. The mixture was now evaporated to dryness on a rotary evaporator in vacuo, and the solid residue was dried over concentrated sulphuric acid and at about 12 mm Hg.

Yield: 93% Melting point = 150° C after recrystallisation from acetone-pentane.

Calculated: C 32.3 H 3.4 N 18.8 Cl 23.9 Found: C 32.3 H(4.5) N 18.7 Cl 23.9

NMR signals at $\tau = 5.7$ to 6.1 (2 H), and 6.3 to 6.7 (2 H), (acetone-$d_6$ as the solvent), symmetrical $A_2B_2$-system. IR bands at 3230, 1790, 1700, 1270 and 1150 $cm^{-1}$.

EXAMPLE 145

If, in the procedure of Example 144, the D-α-aminobenzylpenicillin used therein is replaced by 0.04 mol of α-amino-p-methylbenzylpenicillin,
α-amino-p-chlorobenzylpenicillin,
α-amino-p-methylthiobenzylpenicillin,
α-amino-α-(2)thienylmethylpenicillin or
α-amino-α-(3)thienylmethylpenicillin,
the following penicillins are obtained:
α-(imidazolidin-2-on-1-yl-carbonylamino)-p-methylbenzylpenicillin,
α-(imidazolidin-2-on-1-yl-carbonylamino)-p-chlorobenzylpenicillin,
α-(imidazolidin-2-on-1-yl-carbonylamino)-p-methylthiobenzylpenicillin,
α-(imidazolidin-2-on-1-yl-carbonylamino)-α-(2)-thienylmethylpenicillin or
α-(imidazolidin-2-on-1-yl-carbonylamino)-α-(3)thienylmethylpenicillin.

EXAMPLE 146

If, in the procedure of Example 144, the 1 chlorocarbonylimidazolidone used therein is replaced by 0.035 mol of:
1-chlorocarbonyl-1,3-diazacylclohexan-2-one,
1-chlorocarbonyl-1,3-diazacycloheptan-2-one,
1-chlorocarbonyl-5methyl-imidazolidone 2),
1-chlorocarbonyl-4-methyl-imidazolidone(2),
1-chlorocarbonyl-5,5-dimethyl-imidazolidone(2),
1-chlorocarbonyl-4,4-dimethyl-imidazolidone(2),
1-chlorocarbonyl-4,5-cis-dimethyl-imidazolidone(2),
1-chlorocarbonyl-4,5-trans-dimethyl-imidazolidone,
1-chlorocarbonyl-benzimidazolone,
1-chlorocarbonyl-6-methyl-benzimidazolone,
1-chlorocarbonyl-5-methyl-benzimidazolone,
1-chlorocarbonyl-4-methyl-benzimidazolone,
1-chlorocarbonyl-7-methylbenzimidazolone,
1-chlorocarbonyl-5-nitrobenzimidazolone,
1-chlorocarbonyl-6-nitrobenzimidazolone,
1-chlorocarbonyl-hexahydrobenzimidazolone(2),
1-chlorocarbonyl-6-aza-benzimidazolone,
1-chlorocarbonyl-5-aza-benzimidazolone,
1-chlorocarbonyl-6-carbethoxy-benzimidazolone or
2-chlorocarbonyl-2,4-diazebicyclo[3,2,2]-noran-3-one,
the following penicillins are obtained:-
D(−)-α-(1,3-diazacylohexan-2-on-1-yl-carbonylamino)-benzylpenicillin, j
D(−)-α-(1,3-diazacycloheptan-2-on-1-yl-carbonylamino)-benzylpenicillin,
D(−)-α-(5-methyl-imidazolidin-2-on-1-yl-carbonylamino)-benzylpenicillin,
D(−)-α-(4-methylimidazolidin-2-on-1-yl-carbonylamino)benzylpenicillin,
D(−)-α(5,5-dimethylimidazolidin-2-on-1-yl-carbonylamino)-benzylpenicillin,
D(−)-α-(4,4-dimethylimidazolidin-2-on-1-yl-carbonylamino)-benzylpenicillin,
D(−)-α-(4,5-cis-dimethylimidazolidin-2-on-1-yl-carbonylamino)-benzylpenicillin,
D(−)-α-(4,5-trans-dimethylimidazolidin-2-on-l-yl-carbonylamino)benzylpenicillin,
D(−)-α-(benzimidazolin-2-on-1-yl-carbonylamino)-benzylpenicillin,
D(−)-α-(6-methylbenzimidazolin-2-on-1-yl-carbonylamino)-benzylpenicillin,
D(−)-α-(5-methylbenzimidazolin-2-on-1-yl-carbonylamino)-benzylpenicillin,
D(−)-α-(4-methylbenzimidazolin-2-on-1-yl-carbonylamino)-benzylpenicillin,
D(−)-α-(7-methylbenzimidazolin-2-on-1-yl-carbonylamino)-benzylpenicillin,
D(−)-α-(5-nitrobenzimidazolin-2-on-1-yl-carbonylamino)-benzylpenicillin,
D(−)-α-(6-nitrobenzimidazolin-2-on-1-yl-carbonylamino)-benzylpenicillin,
D(−)-α-(hexahydrobenzimidazolin-2-on-1-yl-carbonylamino)-benzylpenicillin,
D(−)-α-(6-azabenzimidazolin-2-on-1-yl-carbonylamino)-benzylpenicillin,
D(−)-α-(5-azabenzimidazolin-2-on-1-yl-carbonylamino)-benzylpenicillin,
D(−)-α-(5-carbethoxybenzimidazolin-2-on-1-yl-carbonylamino)benzylpenicillin,
D(−)-α-(6-carbethoxybenzimidazolin-2-on-1-yl-carbonylamino)benzylpencillin, D(—)-α-(2,4-diazabicyclo[3,2,2]nonan-3-on-2-yl-carbonylamino)benzylpenicillin.

EXAMPLE 147

A. Sodium D(—)-α-imidazolidine-2-thion-1-yl-carbonylaminobenzylpenicillin 8.5 parts by weight of 1-chlorocarbonyl-imidazolidine 2-thione were reacted with 17.5 parts by weight of D(—)-α-aminobenzylpenicillin in 170 parts by volume of 80% strength aqueous tetrahydrofurane, at 0° C and pH 7.5 to 8.0 (glass electrode), whilst stirring. Triethylamine were added gradually to maintain the pH value. The mixture was further stirred at room temperature until no further addition of triethylamine was necessary to maintain the pH at 7.5. Thereafter, 150 parts by volume of water were added, a pH of 6.5 was established by means of a little dilute hydrochloric acid, and the tetrahydrofurane was stripped off in a rotary evaporator at room temperature. The mixture was now extracted once with ether, the aqueous phase was covered with 300 parts by volume of ethyl acetate, the whole was cooled to 0° C, and dilute hydrochloric acid was introduced, while stirring and cooling with ice, until a pH value of 1.5 to 2.0 was reached. The organic phase was separated off, the aqueous solution was again extracted with 300 parts by volume of ethyl acetate, and the organic solutions were combined and subsequently dried with $MgSO_4$. On adding about 40 parts by volume of a 1 molar solution of sodium 2-ethylhexanoate in ether containing methanol, the sodium salt of the penicillin precipitated. The bulk of the ethyl acetate was stripped from the suspension in vacuo, the residue was dissolved in methanol and added dropwise to a mixture of 300 parts by volume of ether and 30 parts by volume of methanol. The ether methanol mixture was decanted from the precipitated product after it had stood for a short time, and the product was again repeatedly worked with ether, filtered off and dried over $P_2O_5$ in a vacuum desiccator. Effectivenss against *Psdm, aerug.* Bonn 25 units/ml. Effectiveness against *Proteus* 3400: 50 units/ml. Yield: 40% β-Lactam content: 90% (estimated on the basis of the β-lactam band of the IR spectrum). NMR signals (methanol-$d_4$ as the solvent) at $\tau = 2.3$ to 2.8 (5 H), 4.4 (1 H), 4.55 (2 H), 5.85 (1 H), 6.0 to 6.5 (4 H), 8.4 (3 H) and 8.5 ppm (3 H). IR bands at 3320, 1760, 1720, 1665, 1602, 1520, 1365, and 1255 $cm^{-1}$.

B. 1-Trimethylsilyl-imiazolidine-2-thione 30.6 parts by weight of imidazolidine-2-thione were boiled overnight with 54.4 parts by weight of trimethylchlorosilane and 51.5 parts by weight of triethylamine in absolute tetrahydrofurane. The warm suspension was freed of the precipitated triethylamine hydrochloride by filtration, and the filtrate was evaporated and dried in a vacuum desiccator. Melting point: approx. 130° C. Yield 97% Calculated: N 14.4 S 16.5 Found: N 13.8 S 16.9 Strong Si-C stretching vibration in the IR spectrum at 850 $cm^{-1}$.

C. 1-Chlorocarbonyl-imidazolidine-2-thione 50 parts by weight of 1-trimethylsilyl-imidazolidine-2-thione in 150 parts by volume of methylene chloride were treated with 35 parts by weight of phosgene in 50 parts by volume of methylene chloride over the course of 2 hours at 0° C. The mixture was stirred for 24 hours at 0° C, the methylene chloride was subsequently stripped off, and the residue was dried in a high vacuum. Semi-solid mass, incompletely soluble in acetone. Crude yield: 97% IR bands at 1830, 1590 and 1240 $cm^{-1}$.

EXAMPLE 148

If, following the procedures desired in Example 147A 17.5 parts by weight of ampicillin are reacted with 0.05 mol of:

1-chlorocarbonyl-1,3-diazacyclohexane-2-thione,
1-chlorocarbonyl-4-methylimidazolidine-2-thione,
1-chlorocarbonyl-5-methylimiazolidine-2-thione,
1-chlorocarbonyl-4,4-dimethylimidazolidine-2-thione,
1-chlorocarbonyl-5,5-dimethylimidazolidine-2-thione or
1-chlorocarbonyl-4,5-dimethylimiazolidine-2-thione,
the following penicillins are obtained in the form of their sodium salts:-
D(—)-α-(1,3-diazacyclohexane-2-thion-1-yl-carbonylamino)-benzylpenicillin,
D(—)-α-(4-methylimidazolidine-2-thion-1-yl-carbonylamino)-benzylpenicillin,
D(—)-α-(5-methylimiazolidine-2-thion-1-yl-carbonylamino)-benzylpenicillin,
D(—)-α-(4,4-dimethylimidazolidine-2-thion-1-yl-carbonylamino)benzylpenicillin,
D(—)-α-(5,5-dimethylimidazolidine-2-thion-1-yl-carbonylamino)benzylpenicillin or
D(—)-α-(4,5-dimethylimiazolidine-2-thion-1-yl-carbonylamino)benzylpenicillin.

EXAMPLE 149

If, in the procedure of Example 147-A the D-α-aminobenzylpenicillin used there is replaced by 0.05 mol of
α-amino-p-methylbenzylpenicillin,
α-amono-p-chlorobenzylpenicillin,
α-amino-p-methylthiobenzylpenicillin,
α-amino-α-(2)-thienylmethylpenicillin or
α-amino-α-(3)-thienylmethylpenicillin,
the following penicillins are obtained in the form of their sodium salts:-
α-(imidazolidine-2-thion-1-yl-carbonylamino)-p-methylbenzylpenicillin,
α-(imidazolidine-2-thion-1-yl-carbonylamino)-p-chlorobenzylpenicillin,
α-(imidazolidine-2-thion-1-yl-carbonylamino)-p-methylthiobenzylpenicillin,
α-(imidazolidine-2-thion-1-yl-carbonylamino)-α-(2)thienylmethylpenicillin or
α-(imidazolidine-2-thion-1-yl-carbonylamino)-α-(3)thienylmethylpenicillin.

EXAMPLE 150

A. Sodium D(—)-α-(imidazolidin-2-on-1yl-carbonylamino)benzylpenicillin 5.5 parts by weight of D(—)-α-(imiazolidin-2-on-1-yl-carbonylamino)-benzylpenicillin, which was obtained, moist with water, according to the instructions of Example 144, were dissolved in 13 parts by volume of dimethylacetamide while cooling with ice, and subsequently treated with 10 parts by volume of a 1 molar solution of sodium 2-ethylhexanoate in ether containing methanol. The resulting clear solution was added dropwise over the course of a few minutes to a mixture, cooled to —20° C, of 200 parts by volume of ether and 20 parts by volume of methanol, whereupon the sodium salt of the penicillin separated out as a finely granular precipitate, which was filtered off and thoroughly washed with anhydrous ether. Yield: 81% relative to 1-chlorocarbonyl-imidazolidin-2-one employed. β-Lactam content: 90% (determined on the basis of the intensity of the β-lactam carbonyl band of the IR spectrum). IR bands at 3290, 1770, 1715, 1647, 1538 and 1276 cm$^{-1}$. (IR spectrum in Nujol).

B. Crystalline sodium D(−)-α-(imidazolidin-2-on-1-ylcarbonyl-amino)-benzylpenicillin 0.4 part by weight of the product from Example 92A was dissolved in 0.5 part by volume of water to give a clear solution. 1.3 parts by volume of ethanol were added and the mixture slowly diluted with 3.0 parts by volume of ethyl acetate, while shaking. 0.2 part by weight of sodium D(−):α-(imidazolidin-2-on-1-yl-carbonylamino)-benzylpenicillin crystallised overnight from the initially clear solution, in the form of bundles of fine needles. Decomposition range: 200°–220° C. IR bands at 3370, 3325, 1775, 1728, 1688, 1640 and 1275 cm$^{-1}$. FIGS. 3, 4 and 5 show, the comparison purposes, the IR spectra of D(−)-α-(imidazolidin-2-on-1-yl-carbonylamino)benzylpenicillin as the free acid and as the amorphous and crystalline sodium salt.

What is claimed is:

1. A pharmaceutical composition for treating bacterial infections comprising an antibacterially effective amount of a penicillin of the formula:

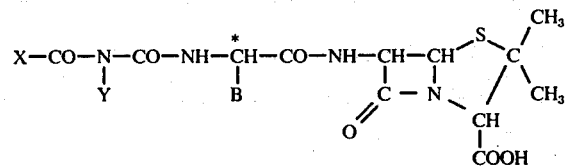

wherein
the carbon atom designated by * constitutes a center of chirality;
X is hydrogen, lower alkyl, monohalo(lower alkyl), dihalo (lower alkyl), trihalo(lower alkyl), lower alkoxy, or cyclohexyloxy;
Y is lower alkyl; and
B is phenyl or phenyl substituted by lower alkyl, lower alkoxy, monohalo, dihalo, or lower alkylthio; or a pharmaceuticaly acceptable nontoxic salt thereof, in combination with a pharmaceutically acceptable nontoxic, inert diluent or carrier.

2. A pharmaceutical composition according to claim 1 wherein each of X and Y is methyl.

3. A pharmaceutical composition according to claim 1 wherein
X is hydrogen, methyl, ethyl, propyl, chloroethyl, chloropropyl, trichloropropyl, trifluoropropyl, methoxy, ethoxy, propoxy, butoxy, or cyclohexyloxy;
Y is methyl, ethyl, or propyl; and
B is phenyl, tolyl, chlorophenyl, methoxyphenyl, methylthiophenyl, or dichlorophenyl.

4. A pharmaceutical composition according to claim 3 wherein C is in the (−)- configuration.

5. A composition according to claim 3 wherein said penicillin is a sodium salt.

6. A composition according to claim 1 wherein said penicillin is (−)-α-(3-formyl-3-methyl-ureido)-benzylpenicillin or the sodium salt thereof.

7. A composition according to claim 1 wherein said penicillin is (−)-α-(3-acetyl-3-methyl-ureido)-benzylpenicillin or the sodium salt thereof.

8. A composition according to claim 1 wherein said penicillin is (−)-α-(3-acetyl-3-ethyl-ureido)-benzylpenicillin or the sodium salt thereof.

9. A composition according to claim 1 wherein said penicillin is (−)-α-(3-acetyl-3-n-propyl-ureido)-benzylpenicillin or the sodium salt thereof.

10. A composition according to claim 1 wherein said penicillin is α-(3-acetyl-3-methyl-ureido)-4-methylbenzylpenicillin or the sodium salt thereof.

11. A composition according to claim 1 wherein said penicillin is α-(3-acetyl-3-methyl-ureido)-p-chlorobenzylpenicillin or the sodium salt thereof.

12. A composition according to claim 1 wherein said penicillin is α-(3-acetyl-3-methyl-ureido)-thien-2-ylmethylpenicillin or the sodium salt thereof.

13. A composition according to claim 1 wherein said penicillin is (−)-α-(3-propionyl-3-methyl-ureido)-benzylpenicillin or the sodium salt thereof.

14. A composition according to claim 1 wherein said penicillin is (−)-α-(3-β-chloropropionayl-3-methyl-ureido)-benzylpenicillin or the sodium salt thereof.

15. A composition according to claim 1 wherein said penicillin is (−)-α-(3-iosbutyl-3-methyl-ureido)-benzylpenicillin or the sodium salt thereof.

16. A composition according to claim 1 wherein said penicillin is (−)-α-(3-γ-chlorobutyryl-3-methyl-ureido)-benzylpenicillin or the sodium salt thereof.

17. A composition according to claim 1 wherein said penicillin is (−)-α-(3-γ-triflurobutyryl)-3-methyl-ureido)-benzylpenicillin or the sodium salt thereof.

18. A composition according to claim 1 wherein said penicillin is (−)-α-(3-γ-trichlorobutryl-3-methyl-ureido)-benzylpenicillin or the sodium salt thereof.

19. A composition according to claim 1 wherein said penicillin is (−)-α-(3-methoxycarbonyl-3-methyl-ureido)-benzylpenicillin or the sodium salt thereof.

20. A composition according to claim 1 wherein said penicillin is (−)-α-(3-ethoxycarbonyl-3-methyl-ureido)-benzylpenicillin or the sodium salt thereof.

21. A composition according to claim 1 wherein said penicillin is (−)-α-(3-i-propoxycarbonyl-3-methyl-ureido)-benzylpenicillin or the sodium salt thereof.

22. A composition according to claim 1 wherein said penicillin is (−)-α-(3-n-butoxycarbonyl-3-methyl-ureido)-benzylpenicillin or the sodium salt thereof.

23. A composition according to claim 1 wherein said penicillin is crystalline sodium (−)-α-(3-acetyl-3-methyl-ureido)benzylpenicillin or the sodium salt thereof.

24. A composition according to claim 1 wherein said penicillin is (−)-α(3-methoxycarbonyl-3-methyl-ureido)-2,6-dichlorobenzylpenicillin or the sodium salt thereof.

25. A composition according to claim 1 wherein said penicillin is (+)-α-(3-methoxycarbonyl-3-methyl-ureido)-2,6-dichlorobenzylpenicillin or the sodium salt thereof.

26. A composition according to claim 1 wherein said penicillin is α-(3-methoxycarbonyl-3-methyl-ureido)-2,6-dichlorobenzylpenicillin or the sodium salt thereof.

27. A composition according to claim 1 wherein said penicillin is α-(3-methoxycarbonyl-3-methyl-ureido)-4-methoxybenzylpenicillin or the sodium salt thereof.

28. A composition according to claim 1 wherein said penicillin is α-(3-ethoxycarbonyl-3-methyl-ureido)-4-methylthiobenzylpenicillin or the sodium salt thereof.

29. A method of treating bacterial infections in humans and animals which comprises administering to said human or animal an anti-bacterially effective amount of a penicillin of the formula:

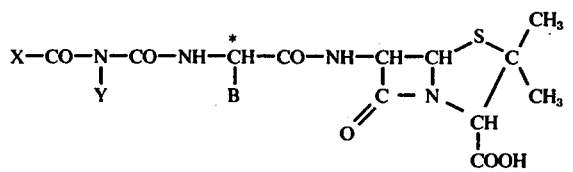

wherein
the carbon atom designated by * constitutes a center of chirality;

X is hydrogen, lower alkyl, monohalo(lower alkyl), dihalo (lower alkyl), trihalo(lower alkyl), lower alkoxy, or cyclohexyloxy;

Y is lower alkyl; and

B is phenyl, or phenyl substituted by lower alkyl, lower alkoxy, monohalo, dihalo, or lower alkylthio;

or a pharmaceutically acceptable nontoxic salt thereof.

30. The method according to claim 29 wherein said amount is from $2.5 \times 10^4$ to $10 \times 10^5$ units/kg of body weight.

31. The method according to claim 29 wherein

X is hydrogen, methyl, ethyl, propyl, chloroethyl, chloropropyl, trichloropropyl, trifluoropropyl, methoxy, ethoxy, propoxy, butoxy, or cyclohexyloxy;

Y is methyl, ethyl, or propyl; and

B is phenyl, tolyl, chlorophenyl, methoxyphenyl, methylthiophenyl, or dichlorophenyl.

* * * * *